US010851224B2

(12) United States Patent
Whitney et al.

(10) Patent No.: US 10,851,224 B2
(45) Date of Patent: Dec. 1, 2020

(54) PHENOLIC RESIN COMPOSITION AND THE USE THEREOF IN A RUBBER COMPOSITION TO REDUCE HYSTERESIS

(71) Applicant: SI GROUP, INC., Schenectady, NY (US)

(72) Inventors: John M. Whitney, Schenectady, NY (US); Darren C. Seel, Schenectady, NY (US); Alexandra Krawicz, Schenectady, NY (US); Timothy E. Banach, Glenville, NY (US)

(73) Assignee: SI GROUP, INC., Schenectady, NY (US)

( * ) Notice: Subject to any disclaimer, the term of this patent is extended or adjusted under 35 U.S.C. 154(b) by 60 days.

(21) Appl. No.: 16/353,718

(22) Filed: Mar. 14, 2019

(65) Prior Publication Data

US 2019/0284370 A1 Sep. 19, 2019

Related U.S. Application Data

(60) Provisional application No. 62/644,160, filed on Mar. 16, 2018, provisional application No. 62/643,611, filed on Mar. 15, 2018.

(51) Int. Cl.
*C08L 7/00* (2006.01)
*C08G 8/28* (2006.01)
(Continued)

(52) U.S. Cl.
CPC .............. *C08L 7/00* (2013.01); *C07C 323/25* (2013.01); *C08G 8/28* (2013.01); *C08J 3/226* (2013.01);
(Continued)

(58) Field of Classification Search
CPC ...... C08L 7/00; C08L 2310/00; C07C 323/25; C08G 8/28; C08J 3/226; C08J 3/24; C08K 5/37; B60C 1/00
(Continued)

(56) References Cited

U.S. PATENT DOCUMENTS 4,308,180 A * 12/1981 Okamura .................. C08G 8/04
524/508

FOREIGN PATENT DOCUMENTS

EP 0732362 A1 9/1996
GB 2044786 A 10/1980

OTHER PUBLICATIONS

Burlov, A.S. , et al., "Electrochemical Synthesis, Structure, Magnetic and Tribochemical Properties of Metallochelates of New Azomethine Ligands, Bis-[2[(N-tosylaminobenzylidenealkyl(aryl)]disulfides," Russian Journal of General Chemistry, vol. 79, No. 3, Mar. 1, 2009, p. 401-407.

(Continued)

*Primary Examiner* — William K Cheung
(74) *Attorney, Agent, or Firm* — Jeffrey N. Townes; Cozen O'Connor

(57) ABSTRACT

This invention relates to a phenolic resin composition comprising a phenolic resin admixed with and/or modified by one or more functionalized organosulfur compounds. This invention also relates to a rubber composition comprising (i) a natural rubber, a synthetic rubber, or a mixture thereof; (ii) one or more phenolic resins; and (iii) one or more functionalized organosulfur compounds. The interaction between the component (i) and the components (ii) and (iii) reduces the hysteresis increase compared to a rubber composition without the component (iii), upon curing the rubber composition. The invention also relates to a process for preparing the phenolic resin composition, a process for preparing the (Continued)

rubber composition, and a process for reducing the hysteresis increase caused in a rubber composition when a phenolic resin is added to a rubber composition.

26 Claims, 8 Drawing Sheets

(51) Int. Cl.

| | |
|---|---|
| *C08J 3/24* | (2006.01) |
| *C08K 5/37* | (2006.01) |
| *C07C 323/25* | (2006.01) |
| *B60C 1/00* | (2006.01) |
| *C08J 3/22* | (2006.01) |

(52) U.S. Cl.
CPC ............... *C08J 3/24* (2013.01); *C08K 5/37* (2013.01); *B60C 1/00* (2013.01); *C08L 2310/00* (2013.01)

(58) Field of Classification Search
USPC .......................................................... 525/150
See application file for complete search history.

(56) References Cited

OTHER PUBLICATIONS

Fox, Charles D., et al., Pyochelin: Novel structure of an iron-chelating growth promoter for Pseudomonas aeruginosa, Proc. Natl. Acad. Sci. USA, vol. 78, Jul. 1, 1981, pp. 4256-4260.

Prakash, Govindan, et al., "New ruthenium(II) carbonyl complexes bearing disulfide Schiff base ligands and their applications as catalyst for some organic transformations," Spectromchimica Acta. Part A: Molecular and Biomolecular Spectroscopy, vol. 129, Aug. 1, 2014, pp. 352-358.

* cited by examiner

PHENOLIC RESIN COMPOSITION AND THE USE THEREOF IN A RUBBER COMPOSITION TO REDUCE HYSTERESIS

This application claims priority to U.S. Provisional Application No. 62/643,611, filed on Mar. 15, 2018, and U.S. Provisional Application No. 62/644,160, filed on Mar. 16, 2018; all of which are herein incorporated by reference in their entirety.

FIELD OF THE INVENTION

This invention generally relates to the use of a phenolic resin and functionalized organosulfur compound in a rubber composition.

BACKGROUND

The rolling resistance of a tire on a surface accounts for much of the energy wasted by an automobile to propel itself forward. Improvements (reduction) in rolling resistance are important as the automotive industry strives for better fuel economy. Rolling resistance is affected by outside factors such as aerodynamic drag and road friction, but is also affected by properties of the tire materials themselves. It is estimated that internal friction and hysteresis of the tire accounts for the majority of the rolling resistance of the tire. For this reason, reducing hysteresis is a major area of focus for improvement. Similarly, hysteresis negatively impacts the performance of rubber articles which experience repetitive motion, such as the motion of a rubber hose or belt.

Phenolic resins are commonly used in rubber compounds to improve the properties or performances of the rubber compounds, e.g., to increase the tackiness of the rubber compound; to improve the abrasion resistance of the rubber compound with better stiffness and toughness; to increase the cross-linking matrix of the rubber compound to provide excellent heat, steam, oxidation, and aging resistance; and to improve the adhesion between the rubber matrix and the surface of the metal or textile inserts. However, one common undesirable side effect of using these resins in rubber compounds is an increase in hysteresis, the heat buildup upon dynamic stress of the rubber article.

Therefore, there remains a need to develop a phenolic resin composition with reduced hysteresis (heat buildup), when employed in a rubber article, while maintaining other desirable properties that the various types of phenolic resins introduce into the rubber composition. This disclosure addresses that need.

SUMMARY OF THE INVENTION

One aspect of the invention relates to a functionalized organosulfur compound. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is bonded to the thiol, disulfide, polysulfide, or thioester moiety through a linking moiety and at least one divalent moiety selected from the group consisting of imine, amine, amide, imide, ether, and ester moiety.

In certain embodiments, the phenolic resin composition comprises the admixture of the phenolic resin and the functionalized organosulfur compounds.

In certain embodiments, the phenolic resin composition comprises the reaction product of at least one phenolic compound, at least one aldehyde, and the one or more functionalized organosulfur compounds. In one embodiment, the at least one phenolic compound and the at least one aldehyde are reacted to form a phenolic resin, and the formed phenolic resin is reacted with the one or more functionalized organosulfur compounds to form the reaction product. In one embodiment, the at least one phenolic compound and the one or more functionalized organosulfur compounds are reacted to form a modified phenolic compound, and the formed modified phenolic compound is reacted with the at least one aldehyde to form the reaction product. In one embodiment, the at least one phenolic compound, the at least one aldehyde, and the one or more functionalized organosulfur compounds are reacted in one-step to form the reaction product.

In certain embodiments, the phenolic resin is a monohydric- or dihydric-phenolic-aldehyde resin, optionally modified by a naturally-derived organic compound containing at least one unsaturated bond. In one embodiment, the phenolic resin is a phenol-aldehyde resin, alkylphenol-aldehyde resin, resorcinol-aldehyde resin, or combinations thereof.

In one embodiment, the phenolic resin is a novolak resin.

In certain embodiments, wherein the phenolic resin is used as a bonding resin or a reinforcing resin.

In certain embodiments, the amount of the functionalized organosulfur compound ranges from about 0.1 to about 25 wt %.

In certain embodiments, the organosulfur compound is a thiol, disulfide, or thioester compound, having at least one functionalization connected to the thiol, disulfide, or thioester moiety through a linking moiety and at least an imine, amine, ether, or ester moiety.

In certain embodiments, one or more organosulfur compounds have the structure of formula (B-1) or (B-2):

$$R_5—R_3—R_1—X—R_2—R_4—R_6 \quad (B\text{-}1)$$

or $$R_5—R_3—R_1—S—H \quad (B\text{-}2),$$

wherein:

X is $S_z$ or $S—C(=O)$;

z is an integer from 2 to 10;

$R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

$R_3$ and $R_4$ each are independently absent, or a divalent form of imine (—R'''—N=C(R')—R'''—), amine (—R'''—N(R')—R'''—), amide

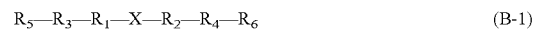

imide

ether (—R'''—O—R'''—), or ester

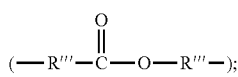

provided that at least one of $R_3$ and $R_4$ is present;

$R_5$ and $R_6$ each are independently H, alkyl, aryl, alkylaryl, arylalkyl, acetyl, benzoyl, thiol, sulfonyl, nitro, cyano, epoxide

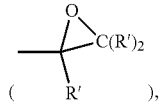

anhydride

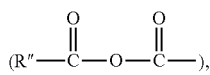

acyl halide

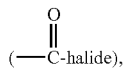

alkyl halide, alkenyl, or a phenolic moiety having one or more unsubstituted para- or ortho-positions; provided that at least one of $R_5$ and $R_6$ is a phenolic moiety having one or more unsubstituted para- or ortho-positions; and provided that when $R_3$ is —R'''—O—R'''—, $R_5$ is not H, and when $R_4$ is —R'''—O—R'''—, $R_6$ is not H; and each R' is independently H or alkyl, each R'' is independently alkyl, and each R''' is independently absent or divalent form of alkane.

In one embodiment, X is $S_z$, and z is 2. In one embodiment, $R_1$ and $R_2$ each are independently divalent form of $C_1$-$C_{12}$ alkane or divalent form of $C_3$-$C_{12}$ cycloalkane. In one embodiment, $R_3$ and $R_4$ each are independently imine (—R'''—N═C(R')—R'''—) amine (—R'''—N(R')—R'''—), ether (—R'''—O—R'''—), or ester

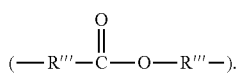

In one embodiment, $R_5$ and $R_6$ each are independently H or a phenolic moiety selected from the group consisting of phenol, alkylphenol, resorcinol, phenyl, and alkylphenyl.

In one embodiment, the organosulfur compound has the structure of formula $R_5$—$R_3$—$R_1$—$S_2$—$R_2$—$R_4$—$R_6$ or $R_5$—$R_3$—$R_1$—SH, wherein:

$R_1$ and $R_2$ each are independently divalent form of $C_1$-$C_{12}$ alkane or divalent form of $C_3$-$C_{12}$ cycloalkane;

$R_3$ and $R_4$ each are independently —N═C(R')—R'''—N(R')—R'''—, or

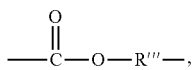

wherein each R' is independently H or $C_1$-$C_{24}$ alkyl, and each R''' is independently absent or divalent form of $C_1$-$C_{24}$ alkane; and $R_5$ and $R_6$ each are independently H or a phenolic moiety selected from the group consisting of phenol, alkylphenol, resorcinol, phenyl, and alkylphenyl.

One aspect of the invention relates to a phenolic resin composition comprising a phenolic resin admixed with and/or modified by one or more functionalized organosulfur compounds. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being bonded to the thiol, disulfide, polysulfide, or thioester moiety through a linking moiety and at least one divalent moiety selected from the group consisting of imine, amine, amide, imide, ether, and ester moiety.

In certain embodiments, the functionalized organosulfur compound has the structure of formula of (B-1) or (B-2):

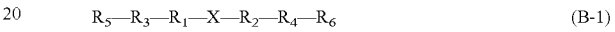

or

wherein:

X is $S_z$ or S—C(═O);

z is an integer from 2 to 10;

$R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

$R_3$ and $R_4$ each are independently absent, or a divalent form of imine (—R'''—N═C(R')R'''—), amine (—R'''—N(R')—R'''—), amide

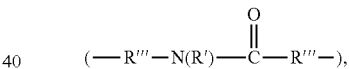

imide

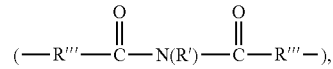

ether (—R'''—O—R'''—), or ester

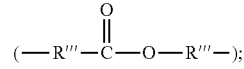

provided that at least one of $R_3$ and $R_4$ is present;

$R_5$ and $R_6$ each are independently H, alkyl, aryl, alkylaryl, arylalkyl, acetyl, benzoyl, thiol, sulfonyl, nitro, cyano, epoxide

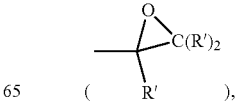

anhydride

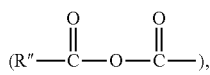

acyl halide

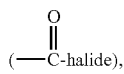

alkyl halide, alkenyl, or a phenolic moiety having one or more unsubstituted para- or ortho-positions; provided that at least one of $R_5$ and $R_6$ is a phenolic moiety having one or more unsubstituted para- or ortho-positions; and provided that when $R_3$ is —R'''—O—R'''—, $R_5$ is not H, and when $R_4$ is —R'''—O—R'''—, $R_6$ is not H; and each R' is independently H or alkyl, each R'' is independently alkyl, and each R''' is independently absent or divalent form of alkane.

Another aspect of the invention relates to a process for preparing a phenolic resin composition. The process comprises admixing a phenolic resin with one or more functionalized organosulfur compounds. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being bonded to the thiol, disulfide, polysulfide, or thioester moiety through a linking moiety and at least one divalent moiety selected from the group consisting of imine, amine, amide, imide, ether, and ester moiety.

Another aspect of the invention relates to a process for preparing a modified phenolic resin. The process comprises reacting at least one phenolic compound, at least one aldehyde, and at least one functionalized organosulfur compound to form the modified phenolic resin. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being connected to the thiol, disulfide, polysulfide, or thioester moiety through a linking moiety and at least one divalent moiety selected from the group consisting of imine, amine, amide, imide, ether, and ester moiety.

In one embodiment, the reacting step comprises: reacting the at least one phenolic compound and the at least one aldehyde to form a phenolic resin, and reacting the formed phenolic resin with the at least one functionalized organosulfur compound to form the modified phenolic resin. In one embodiment, the reacting step comprises: reacting the at least one phenolic compound and the at least one functionalized organosulfur compound to form a modified phenolic compound, and reacting the formed modified phenolic compound with the at least one aldehyde to form the modified phenolic resin. In one embodiment, the reacting step comprises: reacting the at least one phenolic compound, the at least one aldehyde, and at least one functionalized organosulfur compound in one-step to form the modified phenolic resin.

Another aspect of the invention relates to a rubber composition comprising a rubber component comprising a natural rubber, a synthetic rubber, or a mixture thereof; and a functionalized organosulfur compound component comprising one or more functionalized, organosulfur compounds. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being bonded to the thiol, disulfide, polysulfide, or thioester moiety through a linking moiety and at least one divalent moiety selected from the group consisting of imine, amine, amide, imide, ether, and ester moiety.

Another aspect of the invention relates to a rubber composition comprising: (i) a rubber component comprising a natural rubber, a synthetic rubber, or a mixture thereof; (ii) a phenolic resin component comprising one or more phenolic resins; and (iii) an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety.

In one embodiment, component (ii) is pre-admixed with component (iii). In one embodiment, component (ii) is pre-modified by component (iii).

In one embodiment, the rubber composition further comprises one or more methylene donor agents. In one embodiment, the rubber composition further comprises a sulfur curing accelerator.

In certain embodiments, the phenolic resin is a monohydric- or dihydric-phenolic-aldehyde resin, optionally modified by a naturally-derived organic compound containing at least one unsaturated bond. In one embodiment, the phenolic resin is a phenol-aldehyde resin, alkylphenol-aldehyde resin, resorcinol-aldehyde resin, or combinations thereof.

In certain embodiments, the organosulfur compound is a thiol, disulfide, or thioester compound, having at least one functionalization connected to the thiol, disulfide, or thioester moiety through a linking moiety and an imine or ester moiety.

In one embodiment, the amount of the components (ii) and (iii) in the rubber composition range from about 0.5 to about 15 parts per 100 parts rubber by weight. In one embodiment, the amount of the components (ii) and (iii) in the rubber composition range from about 5 to about 50 parts per 100 parts rubber by weight.

In one embodiment, the rubber composition is a reinforced rubber composition, wherein the reinforcing capability of the reinforced rubber composition is comparable or improved compared to a rubber composition without the components (iii).

Certain embodiments of this aspect also relate to a rubber product formed from the rubber composition of this aspect of the invention. In one embodiment, the rubber product is a tire or tire component, a hose, a power belt, a conveyor belt, or a printing roll. For instance, the rubber product is a tire or tire component.

Another aspect of the invention relates to a rubber composition having reduced hysteresis upon curing, comprising (i) a rubber component comprising a natural rubber, a synthetic rubber, or a mixture thereof; (ii) a phenolic resin component comprising one or more phenolic resins; and (iii)

an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety. The interaction between the component (i) and the components (ii) and (iii) reduces the hysteresis increase compared to a rubber composition without the component (iii).

In one embodiment, component (ii) is pre-admixed with component (iii). In one embodiment, component (ii) is pre-modified by component (iii).

In one embodiment, the rubber composition further comprises one or more methylene donor agents. In one embodiment, the rubber composition further comprises a sulfur curing accelerator.

In certain embodiments, the heat buildup, as measured by a flexometer, is reduced by at least about 1° C., compared to a rubber composition without the component (iii). In one embodiment, the heat buildup, as measured by a flexometer, is reduced by at least about 10° C., compared to a rubber composition without the component (iii).

In certain embodiments, the hysteresis increase, as measured by tan δ, is reduced by at least about 10%, compared to a rubber composition without the component (iii). In one embodiment, the hysteresis increase, as measured by tan δ, is reduced by at least about 40%, compared to a rubber composition without the component (iii).

In certain embodiments, the phenolic resin is a monohydric- or dihydric-phenolic-aldehyde resin, optionally modified by a naturally-derived organic compound containing at least one unsaturated bond. In one embodiment, the phenolic resin is a phenol-aldehyde resin, alkylphenol-aldehyde resin, resorcinol-aldehyde resin, or combinations thereof.

In certain embodiments, the organosulfur compound is a thiol, disulfide, or thioester compound, having at least one functionalization connected to the thiol, disulfide, or thioester moiety through a linking moiety and an imine or ester moiety.

In one embodiment, the amount of the components (ii) and (iii) in the rubber composition range from about 0.5 to about 15 parts per 100 parts rubber by weight. In one embodiment, the amount of the components (ii) and (iii) in the rubber composition range from about 5 to about 50 parts per 100 parts rubber by weight.

In one embodiment, the rubber composition is a reinforced rubber composition, wherein the reinforcing capability of the reinforced rubber composition is comparable or improved compared to a rubber composition without the components (iii).

Certain embodiments of this aspect also relate to a rubber product formed from the rubber composition of this aspect of the invention. In one embodiment, the rubber product is a tire or tire component, a hose, a power belt, a conveyor belt, or a printing roll. For instance, the rubber product is a tire or tire component.

Another aspect of the invention relates to a process for preparing a rubber composition. The process comprises mixing (i) a rubber component comprising a natural rubber, a synthetic rubber, or a mixture thereof, (ii) a phenolic resin component comprising one or more phenolic resins, and (iii) an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety.

In one embodiment, the mixing further comprises pre-mixing the component (ii) with component (iii). In one embodiment, the mixing further comprises pre-modifying the component (ii) with component (iii).

In one embodiment, the process further comprises adding a sulfur curing accelerator to the rubber composition in a non-productive stage. In one embodiment, the process further comprises adding a sulfur curing accelerator to the rubber composition in a productive stage.

In one embodiment, the process further comprises adding one or more methylene donor agents to the rubber composition.

In one embodiment, the process further comprises forming a rubber product from the rubber composition. The rubber product may be a tire or tire component, a hose, a power belt, a conveyor belt, a printing roll, a rubber wringer, a ball mill liner, or combinations thereof.

In certain embodiments, the phenolic resin is a monohydric- or dihydric-phenolic-aldehyde resin, optionally modified by a naturally-derived organic compound containing at least one unsaturated bond. In one embodiment, the phenolic resin is a phenol-aldehyde resin, alkylphenol-aldehyde resin, resorcinol-aldehyde resin, or combinations thereof.

In certain embodiments, the organosulfur compound is a thiol, disulfide, or thioester compound, having at least one functionalization connected to the thiol, disulfide, or thioester moiety through a linking moiety and an imine or ester moiety.

Another aspect of the invention relates to a process for reducing the hysteresis increase caused in a rubber composition when a phenolic resin is added to a rubber composition. The process comprises mixing (i) a rubber component comprising a natural rubber, a synthetic rubber, or a mixture thereof, (ii) a phenolic resin component comprising one or more phenolic resins, and (iii) an organosulfur component comprising one or more functionalized organosulfur compounds, thereby resulting in an interaction between the component (i) and the components (ii) and (iii) to reduce the hysteresis increase compared to a rubber composition without the component (iii). In the components (iii), the organosulfur compound is a thiol, disulfide, polysulfide, or thioester compound, and the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety.

In one embodiment, the mixing further comprises pre-mixing the component (ii) with component (iii). In one embodiment, the mixing further comprises pre-modifying the component (ii) with component (iii).

In one embodiment, the process further comprises adding a sulfur curing accelerator to the rubber composition in a non-productive stage. In one embodiment, the process further comprises adding a sulfur curing accelerator to the rubber composition in a productive stage.

In one embodiment, the process further comprises adding one or more methylene donor agents to the rubber composition.

In certain embodiments, the process further comprises curing (vulcanizing) the rubber composition to further reduce the hysteresis increase.

In one embodiment, the amount of the component (iii) relative to the total amount of the components (ii) and (iii) ranges from about 0.1 to about 20 wt %. In one embodiment, the total amount of the components (ii) and (iii) in the rubber composition ranges from about 0.5 to about 15 parts per 100 parts rubber by weight. In one embodiment, the total amount of the components (ii) and (iii) in the rubber composition ranges from about 5 to about 50 parts per 100 parts rubber by weight.

In certain embodiments, the phenolic resin is a monohydric- or dihydric-phenolic-aldehyde resin, optionally modified by a naturally-derived organic compound containing at least one unsaturated bond. In one embodiment, the phenolic resin is a phenol-aldehyde resin, alkylphenol-aldehyde resin, resorcinol-aldehyde resin, or combinations thereof.

In certain embodiments, the organosulfur compound is a thiol, disulfide, or thioester compound, having at least one functionalization connected to the thiol, disulfide, or thioester moiety through a linking moiety and an imine or ester moiety.

In one embodiment, the heat buildup, as measured by a flexometer, is reduced by at least about 1° C., compared to a process being carried out without the component (iii). In one embodiment, the hysteresis increase, as measured by tan δ, is reduced by at least about 10%, compared to a process being carried out without the component (iii).

Additional aspects, advantages and features of the invention are set forth in this specification, and in part will become apparent to those skilled in the art on examination of the following, or may be learned by practice of the invention. The invention disclosed in this application is not limited to any particular set of or combination of aspects, advantages and features. It is contemplated that various combinations of the stated aspects, advantages and features make up the invention disclosed in this application.

BRIEF DESCRIPTION OF THE DRAWINGS

FIG. 5A shows the elastic modulus (G') for each rubber sample. FIG. 5B shows the viscous modulus (G") for each rubber sample. FIG. 5C shows the ratio of elastic modulus over viscous modulus (Tan D) for each rubber sample. The rubber samples are described in Table 3.

FIGS. 11A-1C show the dynamic properties, measured on a rubber process analyzer (RPA) at 100-110° C. and 10 Hz after cure, for each rubber sample. FIG. 11A shows the elastic modulus (G') for each rubber sample.

DETAILED DESCRIPTION OF THE INVENTION

Functionalized Organosulfur Compound

Figure 1:
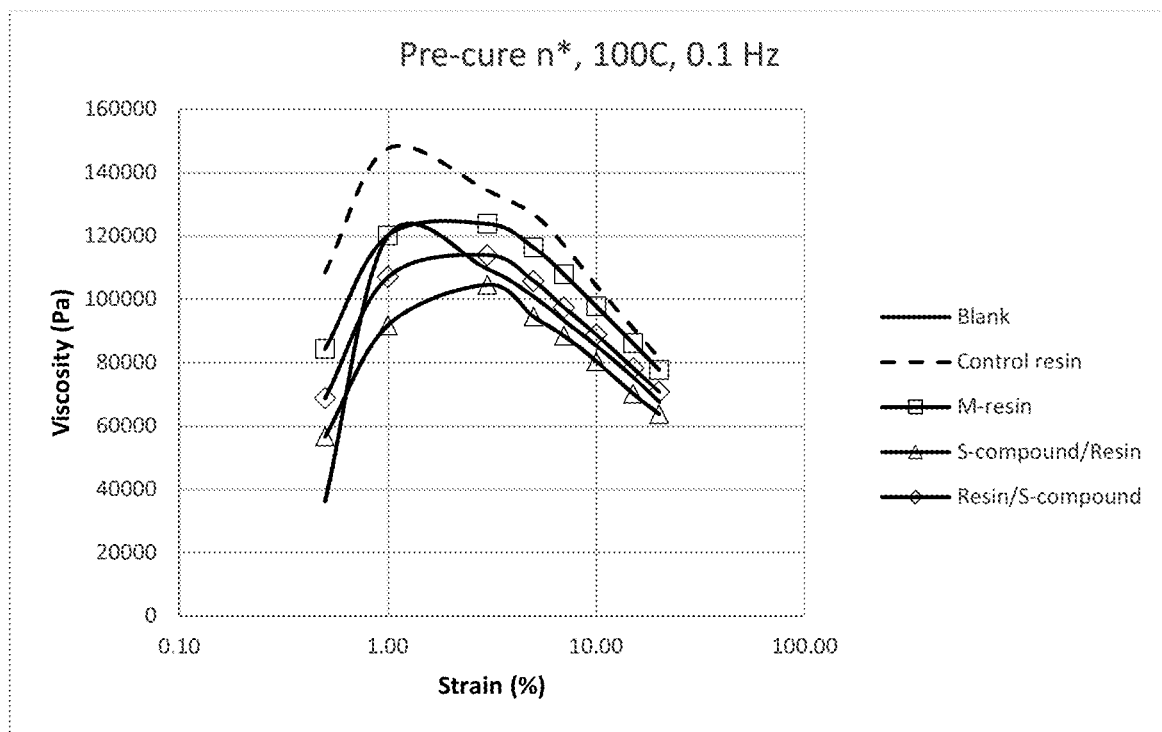
FIG. 1 shows the mixing viscosity for each rubber sample, characterized by pre-cure Strain Sweep n* at 100° C. as a function of strain angle. The rubber samples are described in Table 3.

One aspect of the invention relates to a functionalized organosulfur compound. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being bonded to the thiol, disulfide, polysulfide, or thioester moiety through a linking moiety and at least one divalent moiety selected from the group consisting of an imine, amine, amide, imide, ether, and ester moiety.

This functionalized organosulfur compound is also referred to herein as a "synergistic additive" to be used in a rubber compound that, when combined with a phenolic resin and a methylene donor agent in the rubber compound, can provide a synergistic effect in reducing the heat buildup of the rubber compound.

Suitable organosulfur compounds used in this invention include thiol, disulfide, polysulfide, and thioester compounds. These compounds contain a sulfur group, such as a thiol group (—SH), a sulfide group (including disulfide or polysulfide: —S$_z$—, wherein z is an integer from 2 to 10), or a thioester group

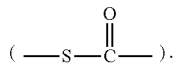

Exemplary organosulfur compounds are a thiol, disulfide, or thioester compound.

The organosulfur compound is functionalized with one or more phenolic moieties. The phenolic moiety is typically being bonded to the thiol, disulfide, polysulfide, or thioester moiety through a linking moiety. The linking moiety can include a divalent form of an aliphatic, alicyclic, heterocyclic group, or a combination thereof, and is typically a divalent form of $C_1$-$C_{30}$ alkane, divalent form of $C_3$-$C_{30}$ cycloalkane, divalent form of $C_3$-$C_{30}$ heterocycloalkane, $C_2$-$C_{30}$ divalent form of alkene, or a combination thereof; each optionally substituted by one or more alkyl, alkenyl, aryl, alkylaryl, arylalkyl, or halide groups. Exemplary linking moieties include divalent form of $C_1$-$C_{12}$ alkane (linear or branched), divalent form of $C_3$-$C_{12}$ cycloalkane, and combinations thereof.

Alternatively, the phenolic moiety can be bonded to the thiol, disulfide, polysulfide, or thioester moiety through one or more heteroatom-containing divalent moieties selected from the group consisting of imine, amine, amide, imide, ether, and ester. Exemplary divalent moieties include an imine, amine, amide, ether, and ester.

Alternatively, the phenolic moiety can also be bonded to the thiol, disulfide, polysulfide, or thioester moiety through a linking moiety and one or more heteroatom-containing divalent moieties selected from the group consisting of imine, amine, amide, imide, ether, and ester.

When the functionalized organosulfur compound contains two or more phenolic moieties, these phenolic moieties may be the same or different, and may be bonded to the thiol, disulfide, polysulfide, or thioester moiety with the same or different linking moiety and/or the same or different heteroatom-containing divalent moiety.

In some embodiments, the organosulfur compound is a thiol, disulfide, or thioester compound. In one embodiment, the organosulfur compound has at least one functionalization connected to the thiol, disulfide, or thioester moiety through a linking moiety, such as a divalent form of $C_1$-$C_{12}$ alkane (linear or branched), divalent form of $C_3$-$C_{12}$ cycloalkane, or combinations thereof, and a heteroatom-containing divalent moiety, such as an imine, amine, amide, ether, or ester.

The term "phenolic moiety" is used to refer to a radical of a monohydric, dihydric, or polyhydric phenol, or its derivative, with or without substituent(s) on the benzene ring of the phenolic moiety. Exemplary phenolic moieties include, but are not limited to: phenol; dihydric-phenols such as resorcinol, catechol, and hydroquinone; dihydroxybiphenyl such as 4,4'-biphenol, 2,2'-biphenol, and 3,3'-biphenol; alkylidenebisphenols (the alkylidene group can have 1-12 carbon atoms, linear or branched) such as 4,4'-methylenediphenol (bisphenol F), and 4,4'-isopropylidenediphenol (bisphenol A); trihydroxybiphenyl; and thiobisphenols. Exemplary monohydric, dihydric, or polyhydric phenols include phenol, resorcinol, and alkylidenebisphenol.

Suitable phenolic moieties also include the derivative of the above phenolic moieties that do not contain a hydroxyl group. For instance, suitable phenolic moieties also include phenyl, diphenyl, hydroxybiphenyl, alkylidenebisphenyls, and thiobisphenyls.

The phenolic moiety can have one or more substituents on the benzene ring of the phenolic moiety, including but not limited to, one or more linear, branched, or cyclic $C_1$-$C_{30}$ alkyl, $C_2$-$C_{30}$ alkenyl, aryl (such as phenyl), alkylaryl, arylalkyl (such as benzyl), halide (F, Cl, or Br), $C_1$-$C_{30}$ alkoxyl, acetyl, benzoyl, carboxyl, thiol, sulfonyl, nitro, amino, and cyano. For example, the benzene ring of the phenolic moiety can be substituted by $C_1$-$C_{24}$ alkyl (e.g., $C_1$-$C_{22}$ alkyl, $C_1$-$C_{20}$ alkyl, $C_1$-$C_{16}$ alkyl, $C_1$-$C_{12}$ alkyl, $C_1$-$C_8$ alkyl, or $C_1$-$C_4$ alkyl) or $C_1$-$C_{24}$ alkoxyl (e.g., $C_1$-$C_{22}$ alkoxyl, $C_1$-$C_{20}$ alkoxyl, $C_1$-$C_{16}$ alkoxyl, $C_1$-$C_{12}$ alkoxyl, alkoxyl, or $C_1$-$C_4$ alkoxyl).

Exemplary phenolic moieties are phenol, alkylphenol (such as cresol), resorcinol, alkylidenebisphenol, phenyl, and alkylphenyl.

Typically, the phenolic moiety has one or more unsubstituted para- or ortho-positions (relative to the hydroxyl group, or relative to the linking moiety or divalent moiety that the phenolic moiety is bonded to). This is to provide a reaction site for the functionalized organosulfur compound to undergo a condensation reaction in the presence of a methylene donor agent.

The functionalized organosulfur compound may have the structure of formula (B-1) or (B-2): $R_5$—$R_3$—$R_1$—X—$R_2$—$R_4$—$R_6$ (B-1) or $R_5$—$R_3$—$R_1$—S—H (B-2), wherein:

X is $S_z$ or S—C(=O);

z is an integer from 2 to 10;

$R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

$R_3$ and $R_4$ each are independently absent, or a divalent form of imine (—R'''—N=C(R')—R'''—), amine (—R'''—N(R')—R'''—), amide

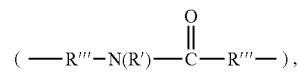

imide

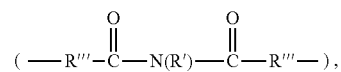

ether (—R'''—O—R'''—), or ester

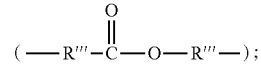

provided that at least one of $R_3$ and $R_4$ is present;

$R_5$ and $R_6$ each are independently H, alkyl, aryl, alkylaryl, arylalkyl, acetyl, benzoyl, thiol, sulfonyl, nitro, cyano, epoxide

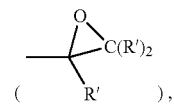

anhydride

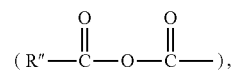

acyl halide

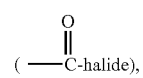

alkyl halide, alkenyl, or a phenolic moiety having one or more unsubstituted para- or ortho-positions; provided that at least one of $R_5$ and $R_6$ is a phenolic moiety having one or more unsubstituted para- or ortho-positions; and provided that when $R_3$ is —R'"—O—R'"—, $R_5$ is not H, and when $R_4$ is —R'"—O—R'"—, $R_6$ is not H; and each R' is independently H or alkyl, each R" is independently alkyl, and each R'" is independently absent or divalent form of alkane.

In formula (B-1), X is a sulfur group that can be represented by $S_z$ or S—C(=O). When X is $S_z$, the integer z can range from 2 to 10, such as 2 to 8, 2 or 5, 2 to 4, or 2 to 3. Typically, z is 2. X can also be a thioester (S—C(=O)).

In formula (B-1) or (B-2), $R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof. For instance, $R_1$ and $R_2$ each may be independently divalent form of $C_1$-$C_{12}$ alkane (linear or branched), divalent form of $C_3$-$C_{12}$ cycloalkane, or combinations thereof.

Each of $R_1$ and $R_2$ may be optionally substituted by one or more alkyl, alkenyl, aryl, alkylaryl, arylalkyl, or halide groups. The optional substituents replace the hydrogen atom(s) of the $R_1$ and $R_2$ groups. Exemplary substituents on $R_1$ and $R_2$ are $C_1$-$C_{16}$ alkyl (linear or branched), $C_2$-$C_{16}$ alkenyl, phenyl, $C_1$-$C_{16}$ alkylphenyl, benzyl, or halide groups. $R_1$ and $R_2$ may be the same or different.

$R_3$ and $R_4$ each are independently absent, or a divalent form of imine (—R'"—N=C(R')—R'"—), amine (—R'"—N(R')—R'"—), amide

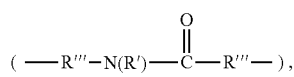, imide

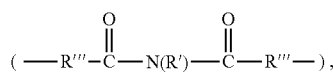, ether (—R'"—O—R'"—), or ester

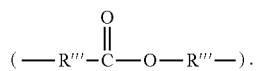.

One of $R_3$ and $R_4$ may be absent, and $R_3$ and $R_4$ may be the same or different. However, at least one of $R_3$ and $R_4$ is present. In one embodiment, $R_3$ and $R_4$ each may be independently imine. In one embodiment, $R_3$ and $R_4$ each may be independently amine. In one embodiment, $R_3$ and $R_4$ each may be independently amide. In one embodiment, $R_3$ and $R_4$ each may be independently imide. In one embodiment, $R_3$ and $R_4$ each may be independently ether. In one embodiment, $R_3$ and $R_4$ each may be independently ester.

$R_5$ and $R_6$ each are independently H, alkyl (e.g., $C_1$-$C_{16}$ alkyl), aryl (e.g., phenyl), alkylaryl (e.g., $C_1$-$C_{16}$ alkylphenyl), arylalkyl (e.g., benzyl), acetyl, benzoyl, thiol, sulfonyl, nitro, cyano, epoxide

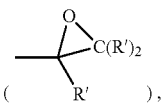, anhydride

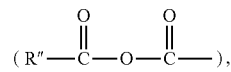, acyl halide

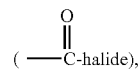, alkyl halide, alkenyl (e.g., $C_2$-$C_{16}$ alkenyl), or a phenolic moiety having one or more unsubstituted para- or ortho-positions. One of $R_5$ and $R_6$ may be absent, and $R_5$ and $R_6$ may be the same or different. However, at least one of $R_5$ and $R_6$ is a phenolic moiety having one or more unsubstituted para- or ortho-positions. When $R_3$ is —R'"—O—R'"—, $R_5$ is not H, and when $R_4$ is —R'"—O—R'"—, $R_6$ is not H. All above descriptions in the context of the "phenolic moiety" and its substituents on the benzene ring, including various exemplary embodiments, are applicable to the definition of the phenolic moiety for $R_5$ and $R_6$.

In one embodiment, one of $R_5$ and $R_6$ is H, alkyl, aryl, alkylaryl, arylalkyl, acetyl, benzoyl, thiol, sulfonyl, nitro, cyano, epoxide, anhydride, acyl halide, alkyl halide, or alkenyl; and one of $R_5$ and $R_6$ is a phenolic moiety having one or more unsubstituted para- or ortho-positions.

In one embodiment, $R_5$ and $R_6$ are each independently a phenolic moiety having one or more unsubstituted para- or ortho-positions.

In one embodiment, $R_5$ and $R_6$ each are independently H or a phenolic moiety selected from the group consisting of phenol, alkylphenol, resorcinol, alkylidenebisphenol, phenyl, and alkylphenyl.

For the R variables, each R' is independently H or alkyl (e.g., $C_1$-$C_{30}$ alkyl, linear or branched), each R" is independently alkyl (e.g., $C_1$-$C_{30}$ alkyl, linear or branched), and each R'" is independently absent or divalent form of alkane (e.g., $C_1$-$C_{30}$ alkylene, linear or branched). For instance, each R' is independently H, or $C_1$-$C_{24}$ alkyl (e.g., $C_1$-$C_6$ alkyl, $C_1$-$C_{12}$ alkyl, or $C_1$-$C_4$ alkyl); each R" is independently $C_1$-$C_{24}$ alkyl (e.g., $C_1$-$C_{16}$ alkyl, $C_1$-$C_{12}$ alkyl, or $C_1$-$C_4$ alkyl); and each R'" is independently absent or divalent form of $C_1$-$C_{24}$ alkane (e.g., $C_1$-$C_6$ alkylene, $C_1$-$C_{12}$ alkylene, or $C_1$-$C_4$ alkylene).

In some embodiments, $R_5$—$R_3$—$R_1$—, —$R_2$—$R_4$—$R_6$, or both, of the organosulfur compound have the structure of

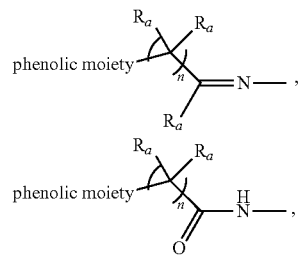

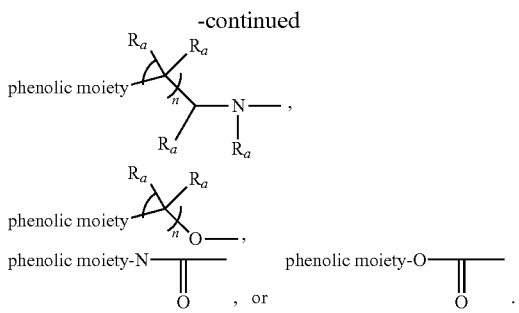

Each $R_a$ is independently H or alkyl (e.g., $C_1$-$C_{30}$ alkyl, $C_1$-$C_{24}$ alkyl, $C_1$-$C_{16}$ alkyl, $C_1$-$C_{12}$ alkyl, or $C_1$-$C_4$ alkyl). The integer n ranges from 0 to 30 (e.g., n is 0, or n is 1 to 20). All above descriptions in the context of the phenolic moiety, including various exemplary embodiments, are applicable to the definition of "phenolic moiety" in these formulas. For instance, exemplary phenolic moieties are phenol, alkylphenol (such as cresol), resorcinol, alkylidenebisphenol, phenyl, and alkylphenyl.

In some embodiments, the organosulfur compound has the structure of formula

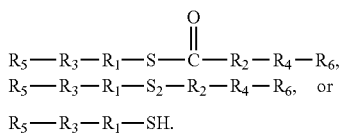

$R_1$ and $R_2$ each are independently divalent form of $C_1$-$C_{12}$ alkane (linear or branched) or divalent form of $C_3$-$C_{12}$ cycloalkane (e.g., $C_1$-$C_6$ alkylene or $C_1$-$C_3$ alkylene). $R_3$ and $R_4$ each are independently —N=C(R')—R'''—, —N(R')—R'''—, —O—R'''—, or

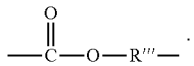

Each R' is independently H or linear or branched $C_1$-$C_{24}$ alkyl (e.g., $C_1$-$C_{17}$ alkyl), and each R''' is independently absent or linear or branched divalent form of $C_1$-$C_{24}$ alkane (e.g., $C_1$-$C_{17}$ alkylene). $R_5$ and $R_6$ each are independently H or a phenolic moiety selected from the group consisting of phenol, alkylphenol, resorcinol, alkylidenebisphenol, phenyl, and alkylphenyl.

In some embodiments, the organosulfur compound has the structure of formula $R_5$—$R_3$—$R_1$—$S_2$—$R_2$—$R_4$—$R_6$ or $R_5$—$R_3$—$R_1$—SH. $R_1$ and $R_2$ each are independently divalent form of $C_1$-$C_{12}$ alkane (linear or branched) or divalent form of $C_3$-$C_{12}$ cycloalkane (e.g., $C_1$-$C_6$ alkylene or $C_1$-$C_3$ alkylene). $R_3$ and $R_4$ each are independently —N=C(R')—R'''—, —N(R')—R'''—, or

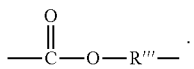

Each R' is independently H or linear or branched $C_1$-$C_{24}$ alkyl (e.g., $C_1$-$C_{17}$ alkyl, linear or branched), and each R''' is independently absent or linear or branched divalent form of $C_1$-$C_{24}$ alkane (e.g., $C_1$-$C_{17}$ alkylene). $R_5$ and $R_6$ each are independently H or a phenolic moiety selected from the group consisting of phenol, alkylphenol, resorcinol, alkylidenebisphenol, phenyl, and alkylphenyl.

In some embodiments, the organosulfur compound has the structure of formula

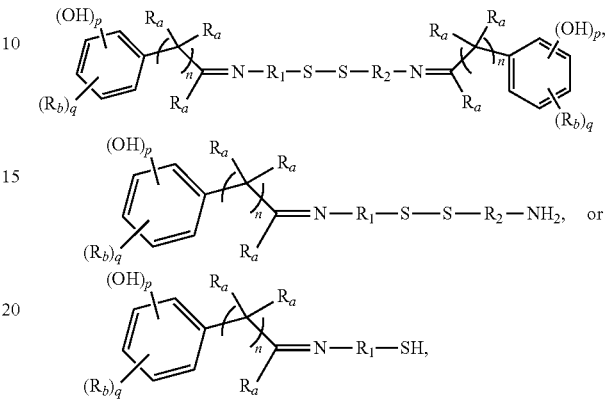

wherein:

$R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

each $R_a$ is independently H or alkyl;

each $R_b$ is independently H, $C_1$-$C_{30}$ alkyl, $C_2$-$C_{30}$ alkenyl, aryl, alkylaryl, arylalkyl, halide, $C_1$-$C_{30}$ alkoxyl, acetyl, benzoyl, carboxyl, thiol, sulfonyl, nitro, amino, or cyano;

n is an integer from 0 to 30 (e.g., n is 0, or n is 1 to 20);

p is 0, 1, or 2; and q is 1 or 2.

All above descriptions for $R_1$ and $R_2$ in formula (B-1) or (B-2), including various exemplary embodiments, are applicable to the definition of $R_1$ and $R_2$ in these formulas.

Each $R_a$ is independently H or alkyl (e.g., $C_1$-$C_{30}$ alkyl, $C_1$-$C_{24}$ alkyl, $C_1$-$C_{16}$ alkyl, $C_1$-$C_{12}$ alkyl, or $C_1$-$C_4$ alkyl).

All above descriptions in the context of the substituents on the benzene ring of the phenolic moiety, including various exemplary embodiments, are applicable to the definition of $R_b$ in these formulas.

In one embodiment, the organosulfur compound has the structure of formula

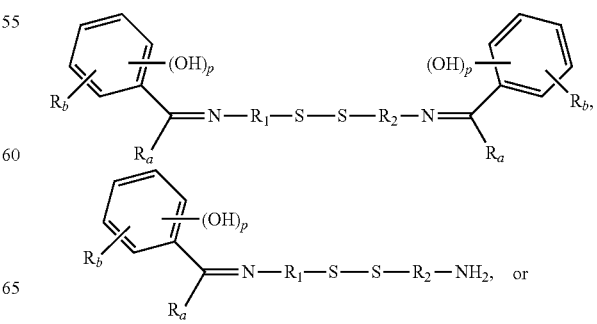

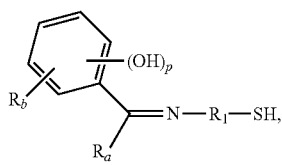

wherein $R_1$ and $R_2$ each are independently divalent form of $C_1$-$C_{12}$ alkane or divalent form of $C_3$-$C_{12}$ cycloalkane; $R_a$ and $R_b$ each are independently H or $C_1$-$C_{24}$ alkyl; and p is 0, 1, or 2. For instance, p is 1 or 2.

One way to prepare these organosulfur compounds is reacting $H_2N$—R—S—S—$R_2$—$NH_2$(2HCl) with

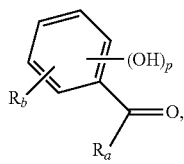

in the absence or presence of an acid catalyst (such as hydrochloric acid), and in the absence or presence of an organic solvent (e.g., an alcohol such as methanol, ethanol, isopropyl alcohol, or 1-butanol). The reaction condition may include heating and optionally reacting under a reflux condition for a period of time.

In one embodiment, the organosulfur compound has the structure of formula

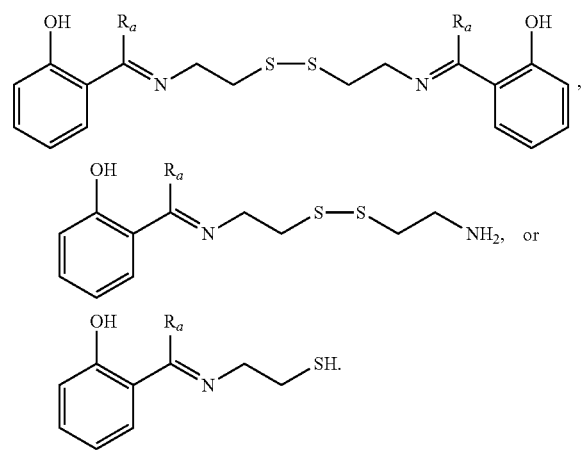

$R_a$ is independently H or $CH_3$.

In one embodiment, the organosulfur compound has the structure of formula

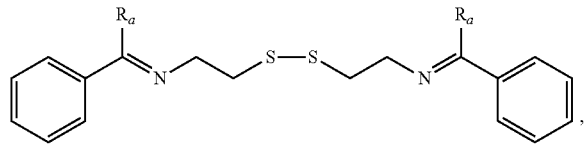

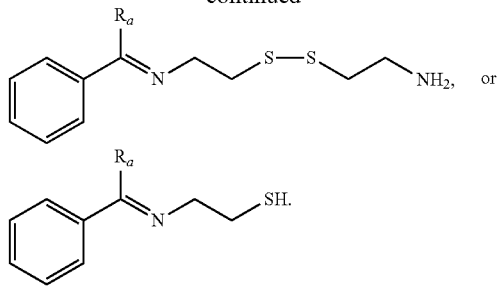

$R_a$ is independently H or $CH_3$.

In some embodiments, the organosulfur compound has the structure of formula

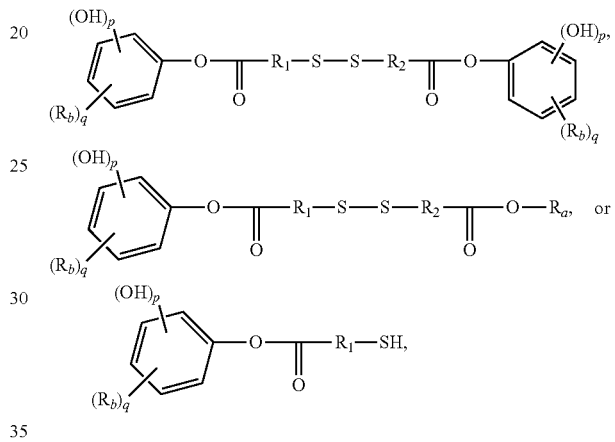

wherein:

$R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

each $R_b$, is independently H, $C_1$-$C_{30}$ alkyl, $C_2$-$C_{30}$ alkenyl, aryl, alkylaryl, arylalkyl, halide, $C_1$-$C_{30}$ alkoxyl, acetyl, benzoyl, carboxyl, thiol, sulfonyl, nitro, amino, or cyano;

p is 0, 1, or 2; and q is 1 or 2.

All above descriptions for $R_1$ and $R_2$ in formula (B-1) or (B-2), including various exemplary embodiments, are applicable to the definition of $R_1$ and $R_2$ in these formulas.

All above descriptions in the context of the substituents on the benzene ring of the phenolic moiety, including various exemplary embodiments, are applicable to the definition of $R_b$ in these formulas.

In one embodiment, the organosulfur compound has the structure of formula

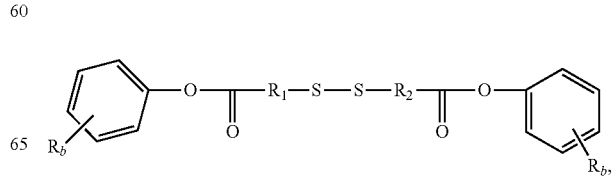

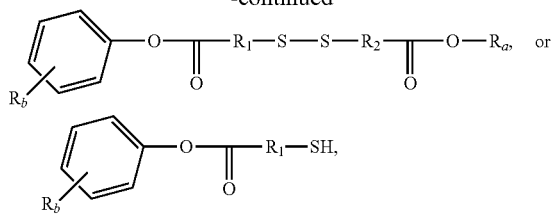

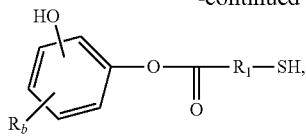

wherein $R_1$ and $R_2$ each are independently divalent form of $C_1$-$C_{12}$ alkane or divalent form of $C_3$-$C_{12}$ cycloalkane; and $R_a$ and $R_b$ each are independently H or $C_1$-$C_{24}$ alkyl. In one embodiment, $R_1$ and $R_2$ each are independently divalent form of $C_2$ alkane, and $R_b$ is H.

In some embodiments, the organosulfur compound has the structure of formula

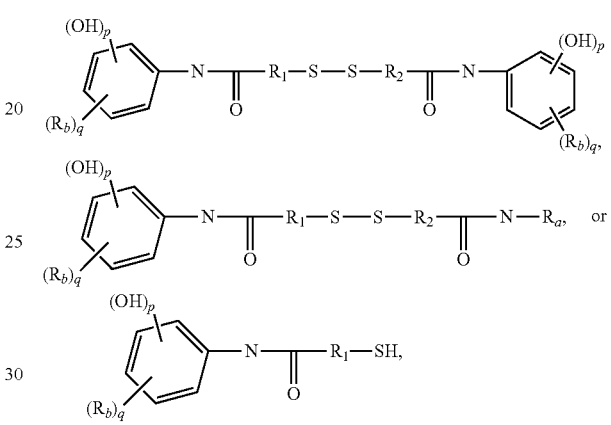

wherein:
$R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

each $R_b$ is independently H, $C_1$-$C_{30}$ alkyl, $C_2$-$C_{30}$ alkenyl, aryl, alkylaryl, arylalkyl, halide, $C_1$-$C_{30}$ alkoxyl, acetyl, benzoyl, carboxyl, thiol, sulfonyl, nitro, amino, or cyano;

p is 1 or 2; and q is 1 or 2.

All above descriptions for $R_1$ and $R_2$ in formula (B-1) or (B-2), including various exemplary embodiments, are applicable to the definition of $R_1$ and $R_2$ in these formulas.

All above descriptions in the context of the substituents on the benzene ring of the phenolic moiety, including various exemplary embodiments, are applicable to the definition of $R_b$ in these formulas.

In one embodiment, the organosulfur compound has the structure of formula

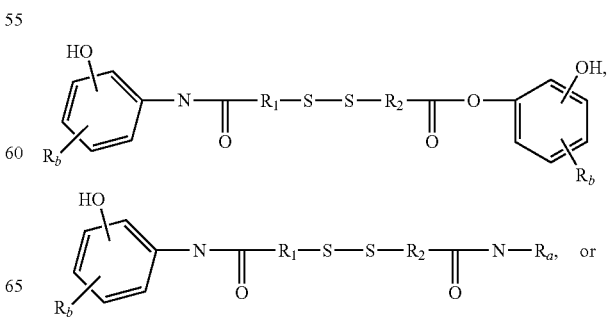

wherein $R_1$ and $R_2$ each are independently divalent form of $C_1$-$C_{12}$ alkane or divalent form of $C_3$-$C_{12}$ cycloalkane; and $R_a$ and $R_b$ each are independently H or $C_1$-$C_{24}$ alkyl.

One way to prepare these organosulfur compounds is reacting

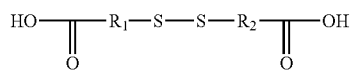

with thionyl chloride in the absence or presence of a base catalyst (such as pyridine), and then reacted with

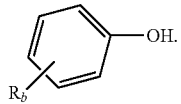

In one embodiment, the organosulfur compound has the structure of formula

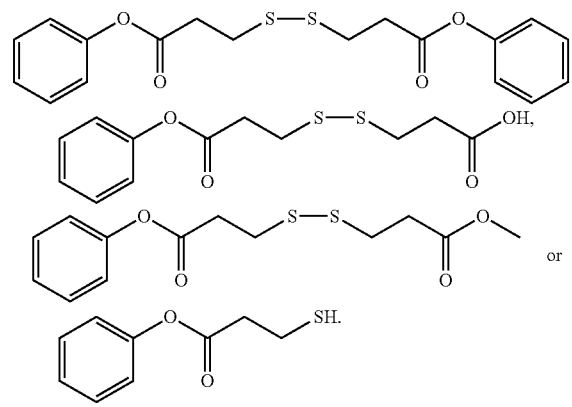

In one embodiment, the organosulfur compound has the structure of formula

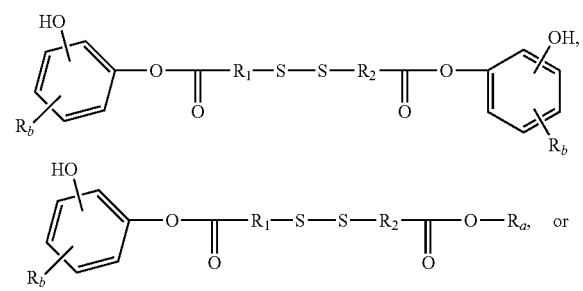

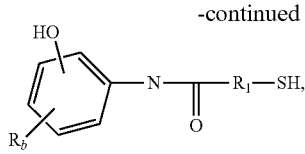

wherein $R_1$ and $R_2$ each are independently divalent form of $C_1$-$C_{12}$ alkane or divalent form of $C_3$-$C_{12}$ cycloalkane; and $R_a$ and $R_b$ each are independently H or $C_1$-$C_{24}$ alkyl. In one embodiment, $R_1$ and $R_2$ each are independently divalent form of $C_2$ alkane, and $R_b$ is H.

In some embodiments, the organosulfur compound has the structure of formula

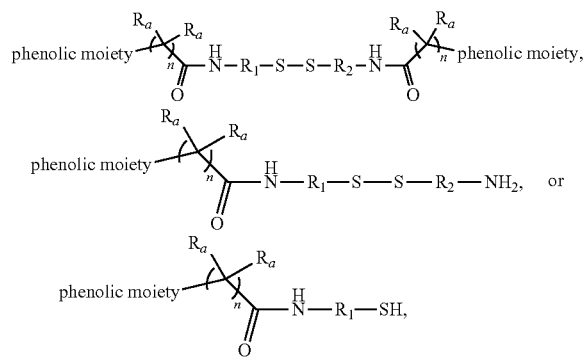

wherein:

$R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

each $R_a$ is independently H or alkyl; and n is an integer from 0 to 30 (e.g., n is 0, or n is 1 to 20).

All above descriptions in the context of the phenolic moiety, including various exemplary embodiments, are applicable to the definition of "phenolic moiety" in these formulas. For instance, exemplary phenolic moieties are phenol, alkylphenol (such as cresol), resorcinol, alkylidenebisphenol, phenyl, and alkylphenyl.

All above descriptions for $R_1$ and $R_2$ in formula (B-1) or (B-2), including various exemplary embodiments, are applicable to the definition of $R_1$ and $R_2$ in these formulas.

Each $R_a$ is independently H or alkyl (e.g., $C_1$-$C_{30}$ alkyl, $C_1$-$C_{24}$ alkyl, $C_1$-$C_{16}$ alkyl, $C_1$-$C_{12}$ alkyl, or $C_1$-$C_4$ alkyl).

One way to prepare these organosulfur compounds is reacting $H_2N$—$R_1$—S—S—$R_2$—$NH_2$ with

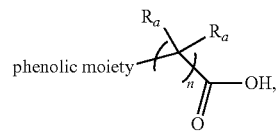

in the absence or presence of an acid catalyst (such as boric acid) or an imide catalyst (such as N,N'-dicyclohexylcarbodiimide), and in the absence or presence of an organic solvent (e.g., xylene, toluene, or other aromatic solvent or an ester solvent). The reaction conditions may include heating and optionally reacting under a reflux condition for a period of time, as appreciated by one skilled in the art.

In certain embodiments, the organosulfur compound has the structure of formula

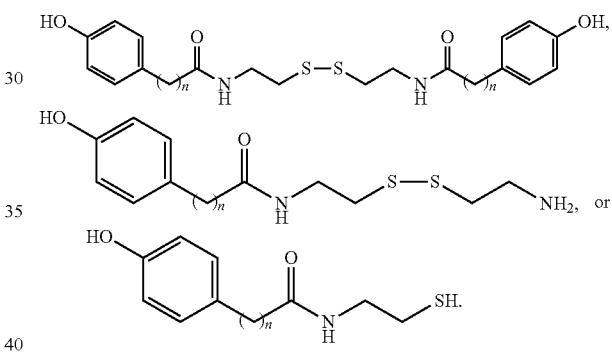

The integer n is independently from 0 to 17. In one embodiment, n is 1. In one embodiment, n is 17.

In certain embodiments, the organosulfur compound has the structure of formula

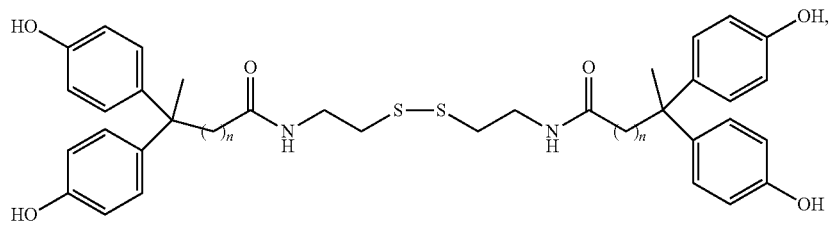

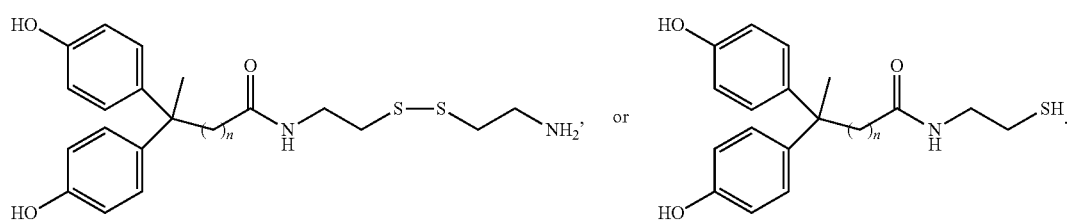

The integer n is independently from 0 to 17. In one embodiment, n is 2. In one embodiment, n is 17.

The term "halide" or "halogen" as used herein refers to a monovalent halogen radical or atom selected from F, Cl, Br, and I. Exemplary groups are F, Cl, and Br.

The terms "divalent form of alkane," "divalent form of cycloalkane," "divalent form of heterocycloalkane," and "divalent form of alkene" as used herein are interchangeable with the terms "alkylene," "alkenylene," "cycloalkylene," and "heterocycloalkylene," respectively, and refer to a divalent radical that is formed by removal of a hydrogen atom from an alkyl, alkenyl, cycloalkyl, or heterocycloalkyl radical, respectively (or by removal of two hydrogen atoms from an alkane, alkene, cycloalkane, or heterocycloalkane, respectively). For instance, in the case of divalent form of alkane (alkylene) or divalent form of alkene (alkenylene), the terms refer to a divalent radical that is formed by removal of a hydrogen atom from each of the two terminal carbon atoms of the alkane or alkene chain, respectively. By way of an example, divalent form of butane (butylene) is formed by removal of a hydrogen atom from each of the two terminal carbon atoms of the butane chain, and has a structure of —$CH_2$—$CH_2$—$CH_2$—$CH_2$—. For instance, in the case of divalent form of cycloalkane (cycloalkylene) or divalent form of heterocycloalkane (heterocycloalkylene), the terms refer to a divalent radical that is formed by removal of a hydrogen atom from each of two different carbon atoms of the cycloalkane or heterocycloalkane ring, respectively. By way of an example, divalent form of cyclopentane (cyclopentylene) is formed by removal of a hydrogen atom from each of two different carbon atoms of the cyclopentane ring, and may have a structure of

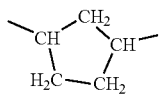

(e.g., 1,3-cyclopentylene).

Phenolic Resin Composition

One aspect of the invention relates to a phenolic resin composition comprising a phenolic resin admixed with and/or modified by one or more functionalized organosulfur compounds. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being bonded to the thiol, disulfide, polysulfide, or thioester moiety through a linking moiety and at least one divalent moiety selected from the group consisting of imine, amine, amide, imide, ether, and ester moiety.

The phenolic resin can be prepared by any phenolic compound known in the art suitable for the condensation reaction with one or more aldehydes.

The phenolic compound may be a monohydric, dihydric, or polyhydric phenol. Suitable monohydric, dihydric, or polyhydric phenols include, but are not limited to: phenol; dihydricphenols such as resorcinol, catechol, hydroquinone; dihydroxybiphenyl such as 4,4'-biphenol, 2,2'-biphenol, and 3,3'-biphenol; alkylidenebisphenols (the alkylidene group can have 1-12 carbon atoms, linear or branched), such as 4,4'-methylenediphenol (bisphenol F), and 4,4'-isopropylidenediphenol (bisphenol A); trihydroxybiphenyls; and thiobisphenols. Exemplary phenolic compounds include phenol or resorcinol.

The benzene ring of the monohydric, dihydric, or polyhydric phenols can be substituted in the ortho, meta, and/or para positions by one or more linear, branched, or cyclic $C_1$-$C_{30}$ alkyl, aryl, alkylaryl, arylalkyl, or halogen (F, Cl, or Br). For example, the benzene ring of the phenolic compound can be substituted by $C_1$-$C_{24}$ alkyl, $C_1$-$C_{16}$ alkyl, $C_4$-$C_{16}$ alkyl, or $C_4$-$C_{12}$ alkyl (such as tert-$C_4$-$C_{12}$ alkyl). Suitable substituents on the benzene ring also include aryl, such as phenyl; $C_1$-$C_{30}$ arylalkyl; or $C_1$-$C_{30}$ alkylaryl.

In certain embodiments, the phenolic compound is phenol, resorcinol, alkylphenol, or a mixture thereof. The alkyl group of the alkylphenol or alkylresorcinol can contain 1 to 30 carbon atoms, 1 to 24 carbon atoms, 1 to 22 carbon atoms, 1 to 20 carbon atoms, 1 to 16 carbon atoms, 1 to 12 carbon atoms, 1 to 10 carbon atoms, 1 to 8 carbon atoms, 4 to 8 carbon atoms, 1 to 6 carbon atoms, or 1 to 4 carbon atoms. Typical alkylphenols include those having one alkyl group, e.g., at the para position of the phenol; and those having two alkyl groups. Exemplary alkylphenols include para-methylphenol, para-tert-butylphenol (PTBP), para-sec-butylphenol, para-tert-hexylphenol, para-cyclohexylphenol, para-heptylphenol, para-tert-octylphenol (PTOP), para-isooctylphenol, para-decylphenol, para-dodecylphenol (PDDP), para-tetradecyl phenol, para-octadecylphenol, para-nonylphenol, para-pentadecylphenol, and para-cetylphenol.

The phenolic resin can be prepared by a condensation reaction of the phenolic compound with one or more aldehydes using any suitable methods known to one skilled in the art. Any aldehyde known in the art suitable for phenol-aldehyde condensation reaction may be used to form the phenolic resins. Exemplary aldehydes include formaldehyde, methylformcel (i.e., formaldehyde in methanol), butylformcel, acetaldehyde, propionaldehyde, butyraldehyde, crotonaldehyde, valeraldehyde, caproaldehyde, heptaldehyde, benzaldehyde, as well as compounds that decompose to aldehyde such as paraformaldehyde, trioxane, furfural (e.g., furfural or hydroxymethylfurfural), hexamethylenetriamine, aldol, β-hydroxybutyraldehyde, and acetals, and mixtures thereof. A typical aldehyde used is formaldehyde or paraformaldehyde.

The resulting phenolic resin can be a monohydric, dihydric, or polyhydric phenol-aldehyde resin known to one skilled in the art. In certain embodiments, the monohydric, dihydric, or polyhydric phenol of the phenol-aldehyde resin is unsubstituted, or substituted with one or more linear, branched, or cyclic $C_1$-$C_{30}$ alkyl, or halogen (F, Cl, or Br). For instance, the phenolic resin may be phenol-aldehyde resin, alkylphenol-aldehyde resin (e.g., cresol-aldehyde resin), resorcinol-aldehyde resin, or combinations thereof.

The phenolic resin may be a novolak resin.

Suitable phenolic resins also include those modified by a naturally-derived organic compound containing at least one unsaturated bond. Non-limiting examples of the naturally-derived organic compounds containing at least one unsaturated bond include naturally derived oils, such as tall oils, linseed oil, cashew nut shell liquid, twig oil, unsaturated vegetable oil (such as soybean oil), epoxidized vegetable oil (such as epoxidized soybean oil); cardol, cardanol, rosins, fatty acids, terpenes, and the like.

The phenolic resin composition can comprise an admixture of one or more phenolic resins described supra and one or more functionalized organosulfur compounds described supra.

Alternatively, the phenolic resin composition can comprise one or more phenolic resins that are modified by one or more functionalized organosulfur compounds described supra. The term "modified," "modify," or "pre-modify" is used herein to include any physical or chemical modification of the phenolic resin by one or more functionalized organosulfur compounds. Therefore, the modification not only includes the scenario where a covalent bond forms between the phenolic resin and the functionalized organosulfur compound resulted from a chemical reaction between the two, but also include interactions such as van der Waals, electrostatic attractions, polar-polar interactions, dispersion forces, or intermolecular hydrogen bonds that may form between the phenolic resin and the functionalized organosulfur compound when the two are mixed together.

In certain embodiments, one or more phenolic resins in the phenolic resin composition are chemically modified by one or more functionalized organosulfur compounds described supra, whereas one or more phenolic resins in the phenolic resin composition are admixed with one or more functionalized organosulfur compounds described supra.

In certain embodiments, the phenolic resin composition comprises the reaction product of at least one phenolic compound, at least one aldehyde, and one or more functionalized organosulfur compounds.

The at least one phenolic compound and the at least one aldehyde may first react to form a phenolic resin, and then the formed phenolic resin may react with the one or more functionalized organosulfur compounds to form the reaction product.

Alternatively, the at least one phenolic compound and the one or more functionalized organosulfur compounds may first react to form a modified phenolic compound, and then the formed modified phenolic compound may react with the at least one aldehyde to form the reaction product. Optionally, one or more additional phenolic compounds, which are not modified by the functionalized organosulfur compounds, may be added to the formed modified phenolic compound, and react with the at least one aldehyde to form the reaction product.

Alternatively, the at least one aldehyde and the one or more functionalized organosulfur compounds may react first to hydroxyalkylate the one or more functionalized organosulfur compounds, and then the hydroxyalkylated functionalized organosulfur compounds may react with the at least one phenolic compound to form the reaction product. For instance, when formaldehyde is used, formaldehyde may react with the functionalized organosulfur compound to methylolate the phenolic moiety of the functionalized organosulfur compound, and then the methylolated functionalized organosulfur compound may react with the at least one phenolic compound to form the reaction product.

Alternatively, the at least one phenolic compound, the at least one aldehyde, and the one or more functionalized organosulfur compounds may react in one-step to form the reaction product.

The phenolic resin composition may further comprise one or more phenolic resins, which are not modified by the functionalized organosulfur compounds.

In certain embodiments, the phenolic resin composition comprises the reaction product of at least one aldehyde, one or more functionalized organosulfur compounds, and one or more phenolic resins (which may be un-modified or modified by a functionalized organosulfur compound). The at least one aldehyde and the one or more functionalized organosulfur compounds may react first to hydroxyalkylate the one or more functionalized organosulfur compounds, and then the hydroxyalkylated functionalized organosulfur compounds may react with the one or more phenolic resins to form the reaction product. For instance, when formaldehyde is used, formaldehyde may react with the functionalized organosulfur compound to methylolate the phenolic moiety of the functionalized organosulfur compound, and then the methylolated functionalized organosulfur compound may react with the one or more phenolic resins to form the reaction product.

Also applicable to this aspect of the invention are all the descriptions and all embodiments regarding the functionalized organosulfur compounds discussed above, relating to the functionalized organosulfur compounds.

The functionalized organosulfur compounds used in the phenolic resin composition can be one or more different functionalized organosulfur compounds. For instance, different functionalized organosulfur compounds with different types of sulfur groups may be used in the phenolic resin composition; different functionalized organosulfur compounds with different types of linking moieties may be used in the phenolic resin composition; and different functionalized organosulfur compounds with different type of heteroatom-containing divalent moieties may be used in the phenolic resin composition. This also includes the scenario where different functionalized organosulfur compounds are produced during the process of making a functionalized organosulfur compound, by, for instance, an incomplete reaction or a side reaction, and the reaction product mixture is used directly to mix and/or react with the phenolic resin to form the phenolic resin composition.

The phenolic resin composition can be used in the form of viscous solutions or, when dehydrated, brittle resins with varying softening points capable of liquefying upon heating. The phenolic resin solution can be an aqueous solution, or the phenolic resin can be dissolved in an organic solvent such as alcohols, ketones, esters, or aromatic solvents. Suitable organic solvents include, but are not limited to, n-butanol, acetone, 2-butoxy-ethanol-1, xylene, propylene glycol, N-butyl cellosolve, diethylene glycol monoethyl ether, and other aromatic solvents or ester solvents, and mixtures thereof.

The phenolic resin composition can be used in the rubber composition as a bonding (adhesive) resin or a reinforcing resin.

A phenolic reinforcing resin is used to increase the dynamic stiffness, surface hardness, toughness, the abrasion resistance, and dynamic modulus of a rubber article. Typically, reinforcing resins are phenol-aldehyde based resins, alkylphenol-aldehyde (e.g., cresol-aldehyde) based resins, or a mixture thereof. These phenolic resins may be modified with a naturally-derived organic compound containing at least one unsaturated bond, as discussed supra, such as a fatty acid, tall oil, or cashew nut shell liquid, and are subjected to a heat treatment.

A phenolic bonding (adhesive) resin is used as an adhesive promotor that can form permanent bonds between the rubber matrix and a non-rubber component in a rubber composition to improve adhesion between the rubber matrix and a non-rubber component such as a mechanical reinforcement (e.g., fabrics, wires, metals, or fibers such as glass fiber inserts), to impart load-bearing properties. Typically, bonding resins are phenol-aldehyde based resins, resorcinol-aldehyde based resins, alkylphenol-aldehyde (e.g., cresol-aldehyde) based resins, or a mixture thereof.

The amount of the functionalized organosulfur compounds in the phenolic resin composition depends on the type of the phenolic resins being used as, and can range from about 0.1 to about 25 wt %. For a bonding resin, the amount of the functionalized organosulfur compound typically ranges from about 0.1 to about 10 wt %, for instance, from about 0.5 to about 10 wt %, from about 1 to about 10 wt %, or from about 5 to about 10 wt %. For a reinforcing resin, the amount of the functionalized organosulfur compound typically ranges from about 1 to about 25 wt %, for instance, from about 1 to about 20 wt %, from about 2 to about 15 wt %, or from about 5 to about 10 wt %.

Another aspect of the invention relates to a process for preparing a phenolic resin composition. The process comprises admixing a phenolic resin with one or more functionalized organosulfur compounds. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being bonded to the thiol, disulfide, polysulfide, or thioester moiety through a linking moiety and at least one divalent moiety selected from the group consisting of imine, amine, amide, imide, ether, and ester moiety.

All above descriptions and all embodiments regarding the phenolic resin and the functionalized organosulfur compounds discussed above in the aspect of the invention relating to the functionalized organosulfur compounds and in the aspect of the invention relating to the phenolic resin composition are applicable to this aspect of the invention.

Another aspect of the invention relates to a process for preparing a modified phenolic resin. The process comprises reacting at least one phenolic compound, at least one aldehyde, and at least one functionalized organosulfur compound to form the modified phenolic resin. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being connected to the thiol, disulfide, polysulfide, or thioester moiety through a linking moiety and at least one divalent moiety selected from the group consisting of imine, amine, amide, imide, ether, and ester moiety.

All above descriptions and all embodiments regarding the phenolic compound, the aldehyde, the phenolic resin, and the functionalized organosulfur compounds discussed above in the aspect of the invention relating to the functionalized organosulfur compounds and in the aspect of the invention relating to the phenolic resin composition are applicable to this aspect of the invention.

The reaction may be carried out by reacting the at least one phenolic compound and the at least one aldehyde to form a phenolic resin, and reacting the formed phenolic resin with the at least one functionalized organosulfur compound to form the modified phenolic resin.

Alternatively, the reaction may be carried out by reacting the at least one phenolic compound and the at least one functionalized organosulfur compound to form a modified phenolic compound, and reacting the formed modified phenolic compound with the at least one aldehyde to form the modified phenolic resin. In the step of reacting the formed modified phenolic compound with the at least one aldehyde, the reaction may further comprise adding one or more additional phenolic compounds, which are not modified by the functionalized organosulfur compounds, to the formed modified phenolic compound, and reacting this mixture with the at least one aldehyde to form the reaction product. Suitable additional phenolic compounds include those discussed above in the aspect of the invention relating to the phenolic resin composition.

Alternatively, the reaction may be carried out by reacting the at least one aldehyde and the one or more functionalized organosulfur compounds to hydroxyalkylate the one or more functionalized organosulfur compounds, and then reacting the hydroxyalkylated functionalized organosulfur compounds with the at least one phenolic compound to form the modified phenolic resin.

Alternatively, the reaction may be carried out by reacting the at least one phenolic compound, the at least one aldehyde, and at least one functionalized organosulfur compound in one-step to form the modified phenolic resin.

In certain embodiments, the process for preparing a modified phenolic resin comprises reacting at least one aldehyde, one or more functionalized organosulfur compounds, and one or more phenolic resins (which may be un-modified or modified by a functionalized organosulfur compound). The reaction may be carried out by reacting the at least one aldehyde with the one or more functionalized organosulfur compounds to hydroxyalkylate the one or more functionalized organosulfur compounds, and then reacting the hydroxyalkylated functionalized organosulfur compounds with the one or more phenolic resins to form the modified phenolic resin.

The reactions are typically carried out at an elevated temperature ranging from about 30° C. to about 200° C., from about 50° C. to about 170° C., or from about 110° C. to about 160° C. When the reaction is carried out to form a phenolic resin first, the phenolic resin may be pre-melted before reacting with the functionalized organosulfur compound.

The process for preparing a phenolic resin composition may further comprise adding one or more additional phenolic resins, which are not modified by the functionalized organosulfur compounds, to the modified phenolic resin prepared by the above reactions. Suitable additional phenolic resins include those discussed above in the aspect of the invention relating to the phenolic resin composition.

Rubber Composition and Rubber Product

Tires, tire components, and other rubber articles are employed in many applications that undergo dynamic deformations. The amount of energy stored or lost as heat during these deformations is known as "hysteresis" (or heat buildup). Hysteresis is often monitored and assessed, as too much hysteresis can affect the performance of certain rubber products.

Phenolic resins are commonly used in rubber compounds to improve the properties or performance of the rubber compounds. However, using these resins typically increases in heat buildup upon dynamic stress of the rubber article.

The inventors have unexpectedly discovered that the use of a particular type of functionalized organosulfur compound, alone or in combination with a phenolic resin (by mixing with the phenolic resin and/or reacting with the phenolic resin), in the presence of a methylene donor agent, in a rubber composition, reduces the heat buildup upon dynamic stress of the rubber article, as compared to a rubber composition that does not contain the functionalized organosulfur compound. Reducing heat buildup in a rubber article, such as a tire, can bring desirable effects such as improving the wear for longevity of the rubber article as well as improving rolling resistance for better fuel economy.

Accordingly, one aspect of the invention relates to a rubber composition comprising a rubber component comprising a natural rubber, a synthetic rubber, or a mixture thereof; and a functionalized organosulfur compound component comprising one or more functionalized, organosulfur compounds. The organosulfur compound is a thiol, disulfide, polysulfide, or thioester compound, and the functionalization of the organosulfur compound comprises one or more phenolic moieties having one or more unsubstituted para- or ortho-positions. At least one of the phenolic moieties is being bonded to the thiol, disulfide, polysulfide, or thioester moiety through a linking moiety and at least one divalent moiety selected from the group consisting of imine, amine, amide, imide, ether, and ester moiety.

Another aspect of the invention relates to a rubber composition comprising: (i) a rubber component comprising a natural rubber, a synthetic rubber, or a mixture thereof; (ii) a phenolic resin component comprising one or more phenolic resins; and (iii) an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety.

Another aspect of the invention relates to a rubber composition having reduced hysteresis upon curing, comprising (i) a rubber component comprising a natural rubber, a synthetic rubber, or a mixture thereof, (ii) a phenolic resin component comprising one or more phenolic resins; and (iii) an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety. The interaction between the component (i) and the components (ii) and (iii) reduces the hysteresis increase compared to a rubber composition without the component (iii).

All above descriptions and all embodiments regarding the phenolic resin and the functionalized organosulfur compounds discussed above in the aspect of the invention relating to the functionalized organosulfur compounds and in the aspect of the invention relating to the phenolic resin composition are applicable to these aspects of the invention relating to a rubber composition or a rubber composition having reduced hysteresis upon curing.

When the rubber composition comprises both the phenolic resin component (ii) and the organosulfur component (iii), the component (ii) can be pre-admixed with the component (iii). Alternatively, the component (ii) can be pre-modified by the component (iii). Alternatively, the component (ii) can be added to the rubber composition separately from the component (iii). All above descriptions and all embodiments regarding the modification of the phenolic resin by the functionalized organosulfur compounds, including various types of reactions starting from various types of reactants and resulting in various types of reaction products, discussed above in the aspect of the invention relating to the phenolic resin composition and in the aspect of the invention relating to the process for preparing a modified phenolic resin are applicable to these aspects of the invention relating to a rubber composition or a rubber composition having reduced hysteresis upon curing.

Additionally, the organosulfur component (iii) may be further modified before mixing with the phenolic resin component (ii), before modifying the phenolic resin component (ii), or before being separately added to the rubber component (i). The one or more functionalized organosulfur compounds may be reacted with at least one aldehyde and to hydroxyalkylate the one or more functionalized organosulfur compounds. Then, the hydroxyalkylated functionalized organosulfur compound can be mixed with or react with the phenolic resin component (ii), and the resulting reaction product can be added to the rubber composition. Alternatively, the hydroxyalkylated functionalized organosulfur compound can be directly added to the rubber component (i), in which the hydroxyalkylated functionalized organosulfur compound and the separately added phenolic resin component (ii) can react during rubber mixing, compounding, or curing process.

The amount of organosulfur compound component (iii) contained in the rubber composition, can range from about 0.5 to about 15 parts per 100 parts rubber by weight, from about 1 to about 10 parts per 100 parts rubber by weight, or from about 1 to about 5 parts per 100 parts rubber by weight.

The amount of the phenolic resin component (ii) and the organosulfur component (iii) contained in the rubber composition typically ranges from about 0.5 to about 50 parts per 100 parts rubber by weight, from about 5 to about 50 parts per 100 parts rubber by weight, from about 0.5 to about 15 parts per 100 parts rubber by weight, or from about 0.5 to about 10 parts per 100 parts rubber by weight. These amount ranges are also applicable to the functionalized organosulfur compounds used alone in the rubber composition.

The amount of the organosulfur component (iii) relative to the total amount of the phenolic resin component (ii) and the organosulfur component (iii) depends on the type of the phenolic resins being used as, and can range from about 0.1 to about 25 wt %. For a bonding resin, the amount of the organosulfur component (iii) relative to the total amount of the components (ii) and (iii) typically ranges from about 0.1 to about 10 wt %, for instance, from about 0.5 to about 10 wt %, from about 1 to about 10 wt %, or from about 5 to about 10 wt %. For a reinforcing resin, the amount of the organosulfur component (iii) relative to the total amount of the components (ii) and (iii) typically ranges from about 1 to about 25 wt %, for instance, from about 1 to about 20 wt %, from about 2 to about 15 wt %, or from about 5 to about 10 wt %.

These rubber compositions include a rubber component, such as a natural rubber, a synthetic rubber, or a mixture thereof. For instance, the rubber composition may be a natural rubber composition. Alternatively, the rubber composition can be a synthetic rubber composition. Representative synthetic rubbery polymers include diene-based synthetic rubbers, such as homopolymers of conjugated diene monomers, and copolymers and terpolymers of the conjugated diene monomers with monovinyl aromatic monomers and trienes. Exemplary diene-based compounds include, but are not limited to, polyisoprene such as 1,4-cis-polyisoprene and 3,4-polyisoprene; neoprene; polystyrene; polybutadiene; 1,2-vinyl-polybutadiene; butadiene-isoprene copolymer; butadiene-isoprene-styrene terpolymer; isoprene-styrene copolymer; styrene/isoprene/butadiene copolymers; styrene/isoprene copolymers; emulsion styrene-butadiene copolymer; solution styrene/butadiene copolymers; butyl rubber such as isobutylene rubber; ethylene/propylene copolymers such as ethylene propylene diene monomer (EPDM); and blends thereof. A rubber component, having a branched structure formed by use of a polyfunctional modifier such as tin tetrachloride, or a multifunctional monomer such as divinyl benzene, may also be used. Additional suitable rubber compounds include nitrile rubber, acrylonitrile-butadiene rubber (NBR), silicone rubber, the fluoroelastomers, ethylene acrylic rubber, ethylene vinyl acetate copolymer (EVA), epichlorohydrin rubbers, chlorinated polyethylene rubbers such as chloroprene rubbers, chlorosulfonated polyethylene rubbers, hydrogenated nitrile rubber, hydrogenated isoprene-isobutylene rubbers, tetrafluoroethylene-propylene rubbers, and blends thereof.

The rubber composition can also be a blend of natural rubber with a synthetic rubber, a blend of different synthetic rubbers, or a blend of natural rubber with different synthetic rubbers. For instance, the rubber composition can be a natural rubber/polybutadiene rubber blend, a styrene butadiene rubber-based blend, such as a styrene butadiene rubber/natural rubber blend, or a styrene butadiene rubber/butadiene rubber blend. When using a blend of rubber compounds, the blend ratio between different natural or synthetic rubbers can be flexible, depending on the properties desired for the rubber blend composition.

The rubber composition may comprise additional materials, such as one or more methylene donor agents, one or more sulfur curing (vulcanizing) agents, one or more sulfur curing (vulcanizing) accelerators, one or more other rubber additives, one or more reinforcing materials, and one or more oils. As known to one skilled in the art, these additional materials are selected and commonly used in conventional amounts.

In one embodiment, the rubber composition contains one or more methylene donor agents. As discussed above, the presence of methylene donor and a phenolic resin in the rubber compound, together with the presence of the synergistic additive, the functionalized organosulfur compound, produce a synergistic effect in reducing the heat buildup of the rubber compound.

Methylene donor agents in a rubber composition are capable of generating methylene radical by heating upon cure (vulcanization). Suitable methylene donor agents include, for instance, hexamethylenetetramine (HMTA), di-, tri-, tetra-, penta-, or hexa-N-methylol-melamine or their partially or completely etherified or esterified derivatives, for example hexa(methoxymethyl)melamine (HMMM), oxazolidine or N-methyl-1,3,5-dioxazine, and mixtures thereof. Suitable methylene donor agents also include lauryloxymethylpyridinium chloride, ethyloxymethylpyridinium chloride, trioxan hexamethylolmelamine, the hydroxyl groups of which may be esterified or partly etherified, polymers of formaldehyde such as paraformaldehyde, and mixtures thereof. Additional examples for suitable methylene donor agents may be found in U.S. Pat. Nos. 3,751,331 and 4,605,696, which are incorporated herein by reference in their entirety, to the extent not inconsistent with the subject matter of this disclosure. The methylene donor agents can be used in an amount ranging from about 0.1 to about 50 phr (parts per hundred rubber), for instance, from about 0.5 to about 25 phr, from about 0.5 to about 10 phr, from about 1.5 to about 7.5 phr, or from about 1.5 to about 5 phr.

Suitable sulfur curing (vulcanizing) agents include, but are not limited to, Rubbermakers's soluble sulfur; sulfur donating vulcanizing agents, such as an amine disulfide, polymeric polysulfide or sulfur olefin adducts; and insoluble polymeric sulfur. For instance, the sulfur curing agent may be soluble sulfur or a mixture of soluble and insoluble polymeric sulfur. The sulfur curing agents can be used in an amount ranging from about 0.1 to about 15 phr, alternatively from about 1.0 to about 10 phr, from about 1.5 to about 7.5 phr, or from about 1.5 to about 5 phr.

Suitable sulfur curing (vulcanizing) accelerators include, but are not limited to, a thiazole such as 2-mercaptobenzothiazole (MBT), 2-2'-dithiobis(benzothiazole) (MBTS), zinc-2-mercaptobenzothiazole (ZMBT); a thiophosphate such as zinc-O,O-di-N-phosphorodithioate (ZBDP); a sulfenamide such as N-cyclohexyl-2-benzothiazole sulfenamide (CBS), N-tert-butyl-2-benzothiazole sulfenamide (TBBS), 2-(4-morpholinothio)-benzothiazole (MBS), N,N'-dicyclohexyl-2-benzothiazole sulfenamide (DCBS); a thiourea such as ethylene thiourea (ETU), di-pentamethylene thiourea (DPTU), dibutyl thiourea (DBTU); a thiuram such as tetramethylthiuram monosulfide (TMTM), tetramethylthiuram disulfide (TMTD), dipentamethylenethiuram tetrasulfide (DPTT), tetrabenzylthiuram disulfide (TBzTD); a dithiocarbamate such as zinc dimethyldithiocarbamate (ZDMC), zinc diethyldithiocarbamate (ZDEC), zinc dibutyldithiocarbamate (ZDBC), zinc dibenzyldithiocarbamate (ZBEC); and a xanthate such as zinc-isopropyl (ZIX). Additional examples for suitable sulfur curing accelerators may be found in U.S. Pat. No. 4,861,842, which is incorporated herein by reference in its entirety, to the extent not inconsistent with the subject matter of this disclosure. The sulfur curing accelerators can be used in an amount ranging from about 0.1 to about 25 phr, alternatively from about 1.0 to about 10 phr, from about 1.5 to about 7.5 phr, or from about 1.5 to about 5 phr.

Suitable other rubber additives include, for instance, zinc oxides, silica, waxes, antioxidant, antiozonants, peptizing agents, fatty acids, stearates, curing agents, activators, retarders (e.g., scorch retarders), a cobalt source, adhesion promoters, plasticizers, pigments, additional fillers, and mixtures thereof.

Suitable reinforcing materials include, for instance, nylon, rayon, polyester, aramid, glass, steel (brass, zinc or bronze plated), or other organic and inorganic compositions. These reinforcing materials may be in the form of, for instance, filaments, fibers, cords or fabrics.

Suitable oils include, for instance, mineral oils and naturally derived oils. Examples of naturally derived oils include tall oil, linseed oil, cashew nut shell liquid, soybean oil, and/or twig oil. Commercial examples of tall oil include, e.g., SYLFAT® FA-1 (Arizona Chemicals) and PAMAK 4® (Hercules Inc.). The oils may be contained in the rubber composition, relative to the total weight of rubber component, in amounts less than about 5 wt %, for instance, less than about 2 wt %, less than about 1 wt %, less than about 0.6 wt %, less than about 0.4 wt %, less than about 0.3 wt %, or less than about 0.2 wt %. The presence of an oil in the rubber composition may aid in providing improved flexibility of the rubber composition after vulcanization.

The rubber composition, discussed supra, has reduced hysteresis (heat buildup) or dynamic heat buildup upon curing. The heat buildup (reflecting hysteresis increase) of the cured rubber article can typically be measured using a flexometer (such as a BF Goodrich flexometer). The flexometer measures the heat generation of a cured rubber compound, and, because the stretch/compression applies to the whole sample, is a more direct measure of the heat buildup of the rubber article. A rubber formula with a lower value measured by the flexometer has a decreased amount of energy loss by the rubber and, thus, has a lower heat buildup.

Employing the functionalized organosulfur compound in the rubber composition, alone or in combination with a phenolic resin (by mixing with the phenolic resin and/or reacting with the phenolic resin), in the presence of a methylene donor agent, reduces the heat buildup (reflecting hysteresis increase) by at least about 1° C., at least about 2° C., at least about 5° C., at least about 10° C., at least about 15° C.; or can virtually reduce the maximum amount of heat buildup (reflecting hysteresis increase) caused by adding a phenolic resin (without being mixed with or modified by the functionalized organosulfur compound) into a rubber compound, compared to a rubber composition without the functionalized organosulfur compound (or the organosulfur component (iii)), as measured by a flexometer (such as a BF Goodrich flexometer).

The dynamic heat buildup of the final rubber article can be measured by its "tan δ" value. Tan δ (or Tan D) is the ratio of the energy lost to the energy transmitted under dynamic stress, generally characterized by the equation:

$$\tan \delta = \frac{G''}{G'} = \frac{\text{measure of viscous response (energy dissipated as heat)}}{\text{measure of elastic respose (stored energy)}} = \frac{\text{Loss Modulus}}{\text{Storage Modulus}}.$$

A rubber formula with a lower tan δ value has a decreased amount of energy loss to the internal absorption by the rubber and, thus, has a lower dynamic heat buildup.

Employing the functionalized organosulfur compound in the rubber composition, alone or in combination with a phenolic resin (by mixing with the phenolic resin and/or reacting with the phenolic resin), in the presence of a methylene donor agent, reduces the hysteresis increase by at least about 1%, at least about 2%, at least about 5%, at least about 10%, at least about 15%, at least about 20%, at least about 25%, at least about 30%, at least about 35%, or at least about 40%, compared to a rubber composition without the functionalized organosulfur compound (or the organosulfur component (iii)), as measured by tan δ.

In the rubber composition, the interactions between the rubber component (i) and the phenolic resin component (ii) and the organosulfur component (iii) reduce the hysteresis increase compared to a rubber composition without the organosulfur component (iii).

Typically, a phenolic resin does not react with the rubber matrix. An interaction between the rubber and the resin can occur where an interpenetrating network is formed between the two components. For instance, a rubber-to-rubber crosslink network typically forms through the vulcanization process, and a methylene donor agent such as HMMM used in standard rubber formulations can crosslink the resin to supply a resin-to-resin crosslink network. These two crosslink network can interpenetrate each other to provide a reinforcing capability for the rubber composition.

By using the organosulfur component (iii), additional interactions can occur in the rubber composition between the rubber component and the phenolic resin composition (including the phenolic resin component (ii) and the organosulfur component (iii)). This interaction can include, but not limited to, a covalent bonding of the phenolic resin to the rubber unsaturation sites through sulfur crosslinking chemistry, thus "locking" a phenolic resin in place along a rubber backbone to result in improved hysteretic effects for the rubber composition, while retaining the phenolic resin's reinforcing attributes. The interaction between the rubber component and the phenolic resin composition can also include van der Waals, electrostatic attractions, polar-polar interactions, dispersion forces, and/or intermolecular hydrogen bonds that may form between the functionalized organosulfur compound in the phenolic resin composition (including the phenolic resin component (ii) and the organosulfur component (iii)) with the rubber component when the phenolic resin component (ii) and the organosulfur component (iii) are mixed into the rubber composition.

In certain embodiments, the rubber composition is a reinforced rubber composition. The phenolic resin composition (including the phenolic resin component (ii) and the organosulfur component (iii)) is used in the rubber composition as a reinforcing resin. The reinforcing capability of the reinforced rubber composition is maintained or improved compared to a rubber composition without the functionalized organosulfur compound (or the organosulfur component (iii)).

In certain embodiments, the phenolic resin composition (including the phenolic resin component (ii) and the organosulfur component (iii)) is used in the rubber composition as a bonding (adhesive) resin. The bonding (adhesive) properties of the rubber composition are maintained or improved compared to a rubber composition without the functionalized organosulfur compound (or the organosulfur component (iii)).

The rubber compositions according to the invention are curable (vulcanizable) rubber composition and can be cured (vulcanized) by using mixing equipment and procedures known in the art, such as mixing the various curable (vulcanizable) polymer(s) with the phenolic resin compositions, and commonly used additive materials such as, but not limited to, curing agents, activators, retarders and accelerators; processing additives, such as oils; plasticizers; pigments; additional fillers; fatty acid; stearates; adhesive promoters; zinc oxide; waxes; antioxidants; antiozonants; peptizing agents; and the like. As known to those skilled in the art, the additives mentioned above are selected and commonly used in conventional amounts.

The rubber composition discussed above according to this invention exhibits superior properties, including reduced hysteresis. Accordingly, one aspect of the invention also relates to a wide variety of rubber products formed from the rubber composition described supra. Such rubber product can be built, shaped, molded and cured by various methods known to one skilled in the art. All above descriptions and all embodiments in the context of the rubber composition are applicable to this aspect of the invention relating to a rubber product.

Suitable rubber products include those rubber parts or articles that are subject to dynamic motion, for instance, tires or tire components, which include but are not limited to, sidewall, shoulder, tread (or treadstock, subtread), bead, ply, belt, rim strip, inner liner, chafer, carcass ply, body ply skim, wire skim coat, bead filler, overlay compound for tire, or any tire part that can be made of rubber. A more extensive discussion of various tire parts/components can be found in U.S. Pat. Nos. 3,542,108; 3,648,748; and 5,580,919, which are incorporated herein by reference in their entirety, to the extent not inconsistent with the subject matter of this disclosure. Suitable rubber products also include hoses, power belts, conveyor belts, and printing rolls.

One embodiment of the invention relates to a tire or tire component containing the rubber component, the phenolic resin component (ii), and the organosulfur component (iii).

Another aspect of the invention relates to a process for preparing a rubber composition. The process comprises mixing (i) a rubber component comprising a natural rubber, a synthetic rubber, or a mixture thereof, (ii) a phenolic resin component comprising one or more phenolic resins, and (iii) an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety.

Another aspect of the invention relates to a process for reducing the hysteresis increase caused in a rubber composition when a phenolic resin is added to a rubber composition. The process comprises mixing (i) a rubber component comprising a natural rubber, a synthetic rubber, or a mixture thereof, (ii) a phenolic resin component comprising one or more phenolic resins, and (iii) an organosulfur component comprising one or more functionalized organosulfur compounds, thereby resulting in an interaction between the component (i) and the components (ii) and (iii) to reduce the hysteresis increase compared to a rubber composition without the component (iii). In the components (iii), the organosulfur compound is a thiol, disulfide, polysulfide, or thioester compound, and the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one divalent moiety selected from the group consisting of imine, amine, amide, imide, ether, and ester moiety.

All above descriptions and all embodiments regarding the rubber component, the phenolic resin, and the functionalized organosulfur compounds discussed above in the aspect of the invention relating to the functionalized organosulfur compounds, in the aspect of the invention relating to the phenolic resin composition, and in the aspect of the invention relating to the rubber composition are applicable to these aspects of the invention relating to a process for preparing a rubber composition or a process for reducing the hysteresis increase caused in a rubber composition.

The mixing step can further comprise pre-mixing the phenolic resin component (ii) and the organosulfur component (iii) before mixing these two components with the rubber component (i).

The mixing step can further comprise pre-modifying the phenolic resin component (ii) by the organosulfur component (iii) before mixing these two components with the rubber component (i).

Alternatively, the mixing step can further comprise adding the phenolic resin component (ii) and the organosulfur component (iii) separately to the rubber component (i). Then, optionally, the phenolic resin component (ii) can be modified by the organosulfur component (iii) during mixing with the rubber component (i), or during curing (vulcanizing) stage.

All above descriptions and all embodiments regarding the modification of the phenolic resin by the functionalized organosulfur compounds, including various types of reactions starting from various types of reactants and resulting in various types of reaction products, discussed above in the aspect of the invention relating to the phenolic resin composition and in the aspect of the invention relating to the process for preparing a modified phenolic resin are applicable to these aspects of the invention relating to a process for preparing a rubber composition or a process for reducing the hysteresis increase caused in a rubber composition.

Additionally, all above descriptions and all embodiments regarding further modifying the organosulfur component (iii) with at least one aldehyde before mixing with/modifying the phenolic resin component (ii) or before being separately added to the rubber component (i) in the aspect of the invention relating to the rubber composition are applicable to these aspects of the invention relating to a process for preparing a rubber composition or a process for reducing the hysteresis increase caused in a rubber composition.

The mixing of the phenolic resin component (ii) and/or the organosulfur component (iii) with the rubber component (i) can be performed by various techniques known in the rubber industry. For instance, the phenolic resin can be used in the form of viscous solutions or, when dehydrated, brittle resins with varying softening points capable of liquefying upon heating. When used as a solution, liquid, or molten, the phenolic resin component (ii) may be mixed or react with the organosulfur component (iii), and the mixture or reaction product may then be mixed into the rubber composition. Alternatively, the phenolic resin component (ii) and the organosulfur component (iii) may be separately mixed into the rubber composition. When used as a solid, the phenolic resin component (ii) and the organosulfur component (iii) may be mixed with the rubber component (i) using conventional mixing techniques such as internal batch or banbury mixers. Other types of mixing techniques and systems known to those of skill in the art may also be used.

All above descriptions and all embodiments regarding the amounts of the phenolic resin component (ii) and the organosulfur component (iii) contained in the rubber composition and the amount of the organosulfur component (iii) relative to the total amount of the phenolic resin component (ii) and the organosulfur component (iii) discussed above in the aspect of the invention relating to the rubber composition are applicable to these aspects of the invention relating to a process for preparing a rubber composition or a process for reducing the hysteresis increase caused in a rubber composition.

The process may further comprise adding additional materials, such as one or more methylene donor agents, one or more sulfur curing (vulcanizing) agents, one or more sulfur curing (vulcanizing) accelerators, one or more other rubber additives, one or more reinforcing materials, and one or more oils to the rubber composition. All above descriptions and all embodiments regarding these additional materials used in the rubber composition discussed above in the aspect of the invention relating to the rubber composition are applicable to these aspects of the invention relating to a process for preparing a rubber composition or a process for reducing the hysteresis increase caused in a rubber composition.

In certain embodiments, the process further comprises adding a sulfur curing (vulcanizing) accelerator to the rubber composition. Suitable sulfur curing accelerators and the amounts used are the same as described supra in the context of the rubber composition. The sulfur curing accelerator can be added to the rubber composition in a non-productive stage or in a productive stage.

In certain embodiments, the process further comprises adding a sulfur curing (vulcanizing) agent to the rubber composition. Suitable sulfur curing (vulcanizing) agents and the amounts used are the same as described supra in the context of the rubber composition.

In certain embodiments, the process further comprises adding one or more methylene donor agents to the rubber composition. Suitable methylene donor agents and the amounts used are the same as described supra in the context of the rubber composition.

In certain embodiments, the process further comprises adding one or more reinforcing materials to the rubber composition. Suitable reinforcing materials and the amounts used are the same as described supra in the context of the rubber composition.

The process may further comprise curing (vulcanizing) the rubber composition in the absence or presence of a curing agent such as a sulfur curing (vulcanizing) agent. Curing the rubber composition can further reduce the hysteresis increase of the rubber composition. A general disclosure of suitable vulcanizing agents, such as sulfur or peroxide-based curing agents, can be found in *Kirk-Othmer, Encyclopedia of Chemical Technology* (3rd ed., Wiley Interscience, N.Y. 1982), vol. 20, pp. 365-468, particularly *Vulcanization Agents and Auxiliary Materials*, pp. 390-402, or *Vulcanization* by A. Y. Coran, *Encyclopedia of Polymer Science and Engineering* (2$^{nd}$ ed., John Wiley & Sons, Inc., 1989), both of which are incorporated herein by reference, to the extent not inconsistent with the subject matter of this disclosure. Curing agents can be used alone or in combination. Suitable sulfur curing agents and the amounts used also include those discussed supra in the context of the rubber composition.

The process can further comprise forming a rubber product from the rubber composition according to ordinary rubber manufacturing techniques. The final rubber products can also be fabricated by using standard rubber curing techniques. For further explanation of rubber compounding and the additives conventionally employed, one can refer to The Compounding and Vulcanization of Rubber, by Stevens in Rubber Technology, Second Edition (1973 Van Nostrand Reibold Company), which is incorporated herein by reference in their entirety, to the extent not inconsistent with the subject matter of this disclosure.

The final rubber product resulted from the process include those discussed supra in the context of the rubber product.

As discussed above, the process according to this invention can reduce hysteresis of the rubber composition. In certain embodiments, the process reduces the heat buildup (reflecting hysteresis increase) by at least about 1° C., at least about 2° C., at least about 5° C., at least about 10° C., at least about 15° C.; or can virtually reduce the maximum amount of heat buildup (reflecting hysteresis increase) caused by adding a phenolic resin (without being mixed with or modified by the functionalized organosulfur compound) into a rubber compound, compared to a process being carried out without the functionalized organosulfur compound (or the organosulfur component (iii)), as measured by a flexometer (such as a BF Goodrich flexometer).

In certain embodiments, the process reduces the hysteresis increase by at least about 1%, at least about 2%, at least about 5%, at least about 10%, at least about 15%, at least about 20%, at least about 25%, at least about 30%, at least about 35%, or at least about 40%, compared to a process being carried out without the functionalized organosulfur compound (or the organosulfur component (iii)), as measured by tan δ.

EXAMPLES

The following examples are given as particular embodiments of the invention and to demonstrate the practice and advantages thereof. It is to be understood that the examples are given by way of illustration and are not intended to limit the specification or the claims that follow in any manner.

Example 1A: Synthesis of an Exemplary Functionalized Organosulfur Compound—2,2'-[dithiobis(2,1-ethanediylnitriloethylidyne)]bis-phenol

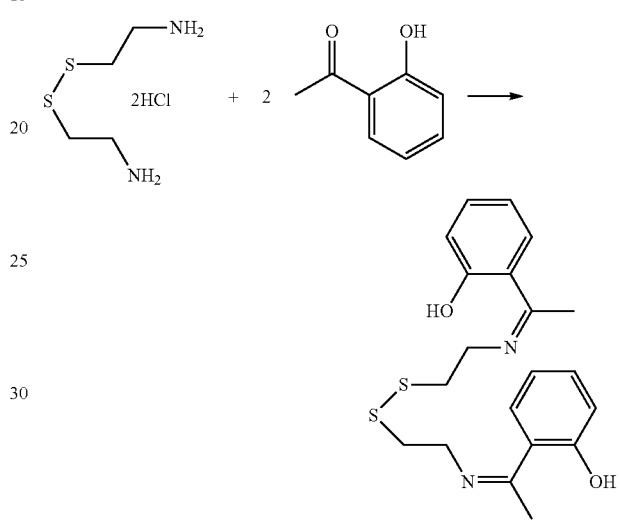

Cystamine dihydrochloride (90.1 g) and 2'-hydroxyacetophenone (108.9 g) were added to a round-bottom flask along with 1-butanol (600.1 g). The contents formed a suspension upon stirring. The reactants were heated to 120° C. and refluxed for a total of 10 hours. The reaction mixture was cooled to 40° C. and sodium hydroxide (32 g) was added. The reaction mixture was stirred for a total of 1 hour during which the temperature was ramped from about 40° C. to about 73.4° C. over a 30-minute period. The reaction mixture was cooled to room temperature and vacuum filtered through a fritted Büchner funnel. Additional 1-butanol (100 g) was used to wash the product and the product isolated in the filter was dried overnight. The solid product was dissolved in dichloromethane (703.7 g) and transferred to a separatory funnel. More dichloromethane (90 g) was used to wash all the product out of the filter and into the separatory funnel. DI (deionized) water (983.5 g) was added to the separatory funnel and used for the first extraction. The phases were allowed to separate and the aqueous layer (1001.0 g) was removed. There was an emulsion layer present between the organic and aqueous phases (114.9 g) which was removed. The organic phase was washed one more time with DI water (621.2 g). The phases were allowed to separate and the organic phase was placed into a 1 L round-bottom flask and rotoevaporated at a reduced pressure. The final product was a yellow powder, with a weight of 138.0 g and a yield of 89%.

The product was analyzed and the structure was verified by $^{13}$C NMR, $^{1}$H NMR, and ESI-MS.

Example 1A': Synthesis of an Exemplary Functionalized Organosulfur Compound—2,2'-[dithiobis(2,1-ethanediylnitriloethylidyne)]bis-phenol

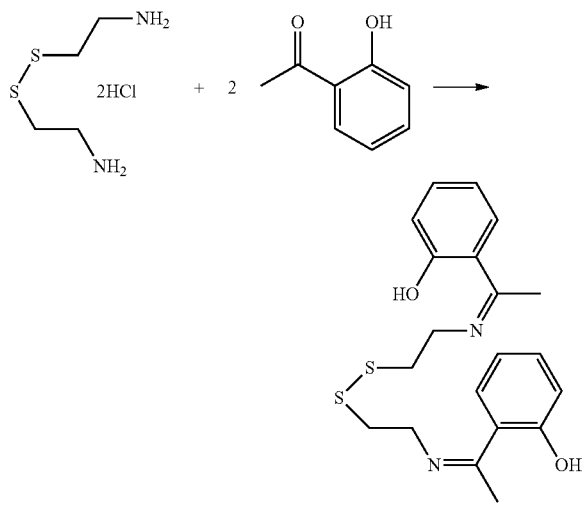

Dissolve cystamine dihydrochloride (40.5 g) in DI water (242.5 g). Load the aqueous cystamine dihydrochloride solution to the kettle. Load 2'-hydroxyacetophenone (49.0 g) to the kettle, followed by addition of isopropyl alcohol (60.1 g). Turn on kettle agitation and upheat the batch to 32° C. Once at temperature load 50% sodium hydroxide (29.0 g) over a period of 20 minutes. Rinse the caustic addition lines with DI water (15.5 g) and hold the batch at temperature with stirring for 2 hours. After the two-hour hold, vacuum filter the batch to remove mother liquors and wash the product once with water (210 g) and twice with isopropyl alcohol (210 g total). Dry the solid under vacuum at 50° C. overnight to afford the disulfide product (63.9 g, 90% yield). The product was analyzed and the structure was verified by $^{13}$C NMR, $^{1}$H NMR, and ESI-MS.

Example 1B: Synthesis of a Modified Phenolic Novolac Resin

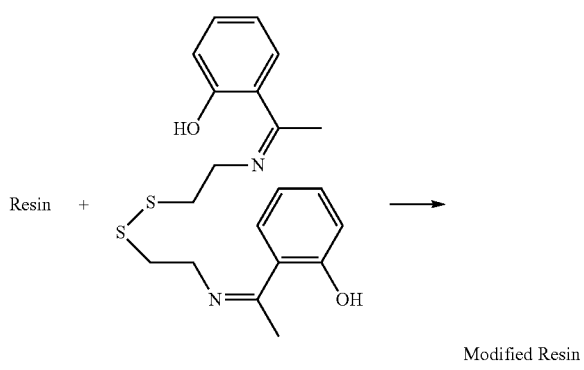

A phenol novolac resin (SI Group HRJ-12952, 400.0 g) was loaded into a round-bottom flask along with 40.0 g 2,2'-[dithiobis(2,1-ethanediylnitriloethylidyne)]bis-phenol (10 wt % of the resin), the functionalized organosulfur compound prepared in Example 1A (or 1A'). The contents of the flask were mixed using a mechanical stirrer quipped with a metal agitator paddle. The reaction mixture was then heated to 160° C. After about 1 hour, the temperature reached 160° C., and the temperature set point was lowered to 120° C. After a total of 2 hours of heating, the reaction mixture were poured into a pan and allowed to cool down forming a solid. The final weight of the recovered product was 438.5 g, with a yield of 99.6%.

Example 2A: Synthesis of an Exemplary Functionalized Organosulfur Compound—diphenyl 3,3'-dithiodipropionate (DPE)

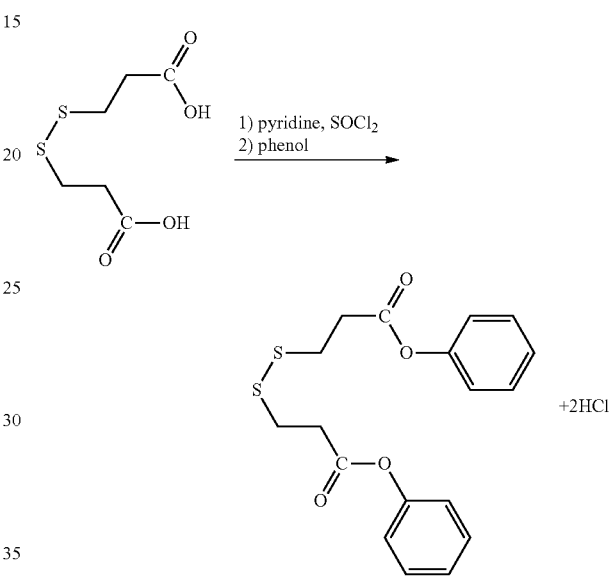

Dithiodipropionic acid (80.2 grams) and pyridine (0.1 g) were charged via syringe to a 500-mL round-bottom flask equipped with thermocouple, addition funnel, drying tube, septum, and nitrogen blanket. Thionyl chloride (92.3 g) was charged to an addition funnel and loaded into the reaction flask dropwise at room temperature (24° C.) over approximately 30 minutes. During this addition period and for the next 2 hours the batch endothermed to a temperature of approximately 8° C. and then slowly returned to room temperature. During the approximately 18 hour reaction period, the batch was stirred and produced gas as evident by bubbles forming in solution. Once the gas evolution stopped, the yellow colored solution was warmed to between 60-85° C. and vacuum was applied to between 55-60 mmHg to remove excess thionyl chloride. Total distillate collected overhead was 14.8 g. The solution was then cooled to 30-40° C.

To make the diphenyl ester, phenol (75.0 g) was charged dropwise on top of the acid chloride over a period of 30 minutes and the solution was stirred overnight. The reaction solution was then vacuum distilled to a temperature of 160° C. and a pressure of 25 mmHg to aid in removal of gaseous hydrochloric acid. At completion, the pH of the reaction product was 6. The resulting reaction mixture was comprised of 87% of the target compound, 5% phenol, and the 7% remainder as byproducts.

Example 2B: Synthesis of a Modified Phenolic Novolac Resin

A phenol novolac resin (SI Group HRJ-12952, 100 g) was pre-melted at a temperature of 110-120° C. in a round-bottom flask equipped with a mechanical stir blade and setup for vacuum distillation to a secondary receiver. Once the resin was fully molten, 10 g diphenyl 3,3'-dithiodipropionate (10 wt % of the resin), the functionalized organosulfur compound prepared in Example 2A, was stirred into the resin and the batch temperature was ramped to 160° C. for 60 minutes. After the initial reaction period, the batch was cooled to 100-125° C. and 25 g xylene was mixed into the batch for 60 minutes. The xylene and free phenol in the batch were removed via vacuum distillation up to a temperature of 160° C. and pressure was slowly drawn to 50 mmHg. The functionalized resin was then dropped to a pan.

Example 3: Preparation of a Rubber Compound

A master batch rubber compound formulated for the shoulder of a tire was used for application testing of the phenolic novolac resin modified by the functionalized organosulfur compounds. The tire shoulder, located between the tread and sidewall, requires reinforcement for stiffness and a lowered hysteresis would aid in improving the wear on the tire and rolling resistance of the vehicle.

The master batch was specially formulated at Valley Rubber Mixing and supplied in 55 lb bales. The master batch was mixed according to the following formula:

| Ingredient | Loading (phr) |
| --- | --- |
| SMR 20 (Smoked Malaysian Rubber) | 100.00 |
| Zinc Oxide | 3.50 |
| Stearic acid | 3.00 |
| Carbon black, N375 | 22.50 |
| Carbon black, N660 | 22.50 |
| Antiozonant 6PPD | 1.20 |
| Antioxidant TMQ(RD) | 0.50 |
| Total master batch | 153.20 |

For individual shoulder formulation samples, the phenolic novolac resin modified by the functionalized organosulfur compounds, as prepared in Examples 1B and 2B, were mixed into the master batch at 10.00 phr, followed by addition of the cure package which includes insoluble sulfur (1.70 phr), N-tert-butyl-benzothiazole sulfonamide (TBBS) sulfur accelerator (1.40 phr), and hexakis(methoxymethyl)-melamine (HMMM) crosslinker (1.30 phr).

Sample Preparation

Compounding of the master batch, the phenolic resin composition, TBBS, and HMMM, was completed in a BR1600HF internal mixer (Farrel Pomini, CT) with automated mixing functionality having a 1.5 L volume capacity and a fill factor of 65% generated to produce 975 g weight of master batch. The rubber was cut into squares approximately 75 mm×75 mm until the fill factor weight of 975 g was obtained. By multiplying 65% fill factor by 10 phr of phenolic resin composition, 1.70 phr sulfur, 1.40 phr TBBS, and 1.30 phr HMMM, the gram weight of the additives being compounded was obtained. Once the total amount of rubber samples were cut and weighed (including the cure package and resin additives), samples were ready to be compounded.

Compounding

For compounding, the rotor speed was 50 rpm and the initial temperature was 60° C. The master batch that was cut and weighed approximately 975 g was added and the ram was dropped. The mixing was carried out for 30 seconds from the drop of the ram. The ram was raised to add the cure package, and was dropped again. The rpms are held constant at 55, and the batch temperature increased from the friction of the master batch, curatives, and resin in the mixer. The mixing time was 2 minutes. After this 2-minute cycle, the batch was expelled into the collection bin. The rubber was then put on the mill to be calendared.

Roll Mill

After the rubber was mixed, each batch that was dropped was immediately milled. The Reliable two roll mill was preheated to approximately 43-45° C., and the dials that control thickness were set to 0 mm for the initial cross-blending. The rubber was banded, and then each side of the rubber was cut, pulled, and allowed to bind with the adjacent side. Each side was cut 3 times for a total of 6 cut and pulls. This process was done for a total of 4 minutes. The sample was then removed from the mill, and cut into two separate sheets.

RPA Sample Prep

To obtain cure data, square samples (approximately 5 g and 50 mm×50 mm) were run on the RPA 2000 (Alpha Technologies). No pre-cure testing was required.

RPA: MDR 160 C Test Procedure

Samples were placed between two mylar film sheets, and then placed on the bottom RPA 2000 die. 160 C test process was followed to determine cure time and torque. The sample was run for 30 minutes and was heated to 160° C. at 1.07 Hz, 6.98% strain to yield cure data, such as T90, which was used to cure samples for other tests.

RPA Passenger Tire Test

Samples were subjected to pre-cure viscosity sweep composed of three strains: Strain 1-100° C., 0.1 Hz for 17 minutes. Strain 2-100° C., 20 Hz for 0.008 minute, and Strain 3-100° C., 1.0 Hz, for 0.167 minute to obtain the pre cure viscosity data. Samples were then cured at 160° C. for 30 minutes at 1.07 Hz, 6.98% strain. After the cure, the samples were subjected to 4 strain sweeps. The $1^{st}$ strain sweep: 0.5-25% strain, 60° C., and 1.0 Hz; the $2^{nd}$ strain sweep: 0.5-25% strain, 60° C., and 1.0 Hz; and the $3^{rd}$ strain sweep: 0.5-25% strain, 60° C., and 1.0 Hz. Another strain sweep at 100° C., 1.0 Hz, and 1.00% strain angle occurred before test sweeps at 60° C. and 10.0 Hz. Samples produced G' elastic response modulus, G" viscous response modulus, and the ratio of elastic modulus over viscous modulus to arrive at the Tan D values.

RPA Mullins Test Procedure

Samples were subjected to pre-cure viscosity sweep composed of three strains: Strain 1-100° C., 0.1 Hz for 17 minutes. Strain 2-100° C., 20 Hz for 0.008 minute, and Strain 3-100° C., 1.0 Hz, for 0.167 minute to obtain the pre cure viscosity data. The sample was then cured for 30 minutes, at 160° C., 1.7 Hz, and 6.98% strain. The sample underwent a post-cure strain at 60° C. and 1.0 Hz, a second strain at 60° C. and 1.0 Hz. The sample finally underwent a temperature sweep from 30-80° C. for 15 minutes, to collect the data: G", G', G*, and Tan D at 30-80° C.

Flexometer Heat Build and Permanent Set Sample Prep

The second of two rubber sheets were remilled and a rectangular sheet was used to make flexometer ASTM D623 samples. Samples for testing were made using a CCSI die approximately 25 mm in height and a CCSI triplate 8 cavity mold with cavities 25 mm in height, 17 mm in diameter. The samples were pressed in a heated hydraulic press according to T90+10 min specifications. Before placing samples in the mold, the heated press was heated to 160° C., and the CCSI mold was preheated to 160° C. After coming off the mill the sample rubber sheet was approximately 300 mm in width and 350 mm in length. The sheet was folded in half four times, and the die was then used to punch three separate punches from the folded rubber sheet to fill the 25 mm cavity in the tri plate mold. Each of the three individual punches were packed into the mold cavity, a piece of foil was placed on top, and the top of the triplate was assembled to the mold. The samples were then cured for a time of T90+10 minutes. The mold was then removed from the press, and the samples were removed from the mold cavities and allowed to cool to room temperature.

Flexometer Heat Buildup and Permanent Set Testing

Samples for heat generation were tested based on ASTM D623 with some slight modifications, as noted below. The test was run on EKT-2002GF (Ektron). The weight of 160N and a frequency of 33 Hz were used. The permanent (flex fatigue) set calculations were also based on ASTM D623 specifications, using a micrometer.

Tensile Strength Properties of Rubber Sample Prep

The first of the two sheets was remilled to make ASTM D412 tensile bars, with the dials rotated 40 degrees counter clockwise to 60 mm. The sample was run back through and milled into a 2 mm rectangular sheet. An ASTM D412 die was used to cut the plaque that eventually became tensile bars. The cut samples were placed in 150 mm×150 mm square cavities. Samples were cured based on T90+4 minutes. After samples were removed, the tensile bars were cut using a die.

Tensile Strength Properties of Rubber

Samples were tested using ASTM D412 method A and an Instron model 5965 universal tensile testing machine (Instron). The video extensimeter (AVE model 2663-901) for recording stress/strain data from the marked cross sectional was calibrated prior to testing. The specimen were marked with two white dots 5 mm apart using a jig. These two small dots represent the test cross section area tested. Samples were then placed in 1 kN pneumatic grips, using a 5 kN load cell to displace the samples for stress/strain calculations.

Durometer Hardness

Hardness of cured rubber samples was determined by using a Rex durometer (Rex Gauge Company Inc.). To determine the hardness of the flexometer samples, the sample was placed flat side down and the anvil was dropped on the top, flat side. To determine the hardness of the Tensile samples, two samples were placed on top of each other and the anvil was dropped on the middle of the cross sectional area.

Property Comparisons Between the Rubber Samples

The rubber samples prepared according to the above procedures were tested according to the above testing protocols, and the results are summarized in Table 1.

TABLE 1

The property comparisons between the rubber samples

| Sample[a] | Stress @ 25% Strain (MPa) | Elongation @ break (%) | dG' (S1-S2)[b] (%) | Permanent Set[c] | Tan-D[d] | Heat Rise[e] (° C.) |
|---|---|---|---|---|---|---|
| Blank | 0.992 | 468 | 15.2 | 0.94 | 0.160 | 17.35 |
| Control (a commercial phenol novolac resin) | 1.000 | 432 | 53.5 | 0.80 | 0.321 | 36.5 |
| Modified phenol novolac resin prepared in Example 1B | 0.999 | 425 | 41.5 | 0.86 | 0.274 | 22.2 |
| Modified phenol novolac resin prepared in Example 2B | 1.000 | 415 | 50.7 | 0.74 | 0.294 | 39.05 |

[a]Samples were mixed into a rubber shoulder master batch compound at 10 phr for application testing.
[b]dG' was measured by RPA as the percentage difference between strain sweep 1 and strain sweep 2 at 3% strain, 60° C., and 1 Hz.
[c]Permanent set was a ratio of final sample height divided by initial sample height measured before and after flexometer testing.
[d]Tan D was measured by RPA for strain sweep 3 at 3% strain, 60° C., 1 Hz.
[e]Heat rise was measured by flexometry.

The blank rubber compound sample consisted of the master batch rubber but contained neither resin nor crosslinker (HMMM). The blank sample exhibited the highest height retention after flexometry as noted by its permanent set value of 0.94. The blank sample also had the lowest Tan D and dynamic heat build-up, because it did not contain any phenolic resin which would contribute to the hysteresis of the rubber compound. The blank sample also displayed the lowest change in elastic response (G') between the first two strain sweeps during RPA testing of the material, providing the lowest Mullins Effect response as compared to the other samples.

The control sample used for comparison to the phenolic resin modified by the functionalized organosulfur compounds was a commercial reinforcing resin (SI Group HRJ-12952). Like the modified phenolic resin samples, the control sample included the use of the HMMM crosslinker during rubber compounding. HMMM provided crosslinking between phenolic moieties, resulting in the formation of a resin-HMMM network that interpenetrates the rubber network and a reinforcing capability to that rubber compound. The control sample exhibited lower permanent sets (0.80) than the blank samples due to the break-down of the interpenetrating network during the cyclical strain of the material during flexometer testing. Addition of a reinforcing resin to the rubber compound also resulted in a much higher Tan D and dynamic heat build-up. This result was caused by the ability of the resin and resin-HMMM crosslinked network to move and flow within the rubber matrix and was illustrated by the approximately doubled Tan D value (0.321 v. 0.160) and heat rise (36.5° C. v. 17.35° C.) when compared to the blank sample. The control sample also exhibited a much higher Mullins Effect (53.5%) than the blank sample, indicating a higher loss of storage modulus than the blank sample.

Pre-synthesized 2,2'-[dithiobis(2,1-ethanediylnitriloethylidyne)]bis-phenol (referred to in this example as "imine") pre-mixed with the phenol novolac resin at 10 wt %, prepared according to Example 1B, showed enhanced improvement in hysteretic drop for a tire shoulder compound compared to the control sample. The imine sample showed a nearly 40% drop in dynamic heat buildup while retaining the reinforcing capabilities as compared to the control sample. The imine sample also exhibited a higher permanent set after flexometry compared to the control sample, indicating a higher degree of the original sample dimensions were retained after flexometry cycling. Mullins effect for the imine-containing sample was also lower (dG'=41.5%) than the control sample, indicating a more stable interpenetrating network and was likely due to the formation of sulfur crosslinks between the functionalized organosulfur compound in the phenolic resin composition and the rubber matrix formed during the rubber compound vulcanization process.

Example 4: Synthesis of an Exemplary Functionalized Organosulfur Compound—2,2'-[dithiobis(2,1-ethanediylnitrilomethylidyne)]bis-phenol

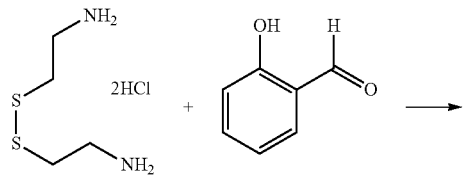

Cystamine dihydrochloride (40.0 g), salicylaldehyde (43.4 g), and sodium acetate were added to a round-bottom flask along with methanol (223 g). The contents formed a suspension upon stirring. The reactants were heated to reflux (67.4-68.4° C.) and held for a total of 1 hour. The reaction mixture was cooled to room temperature and vacuum filtered through a fritted Büchner funnel. Additional methanol (120 ml) was used to wash the product and the product isolated in the filter was dried. The solid product was dissolved in dichloromethane (179.6 g) and transferred to a separatory funnel. DI water (284.6 g) was added to the separatory funnel and used for the first extraction. The phases were allowed to separate and the aqueous layer was removed. The organic phase was washed one more time with DI water (92.0 g). The phases were allowed to separate and the organic phase was placed into a round-bottom flask and rotoevaporated at a reduced pressure. The final product (44.1 g) was a yellow powder coating the round bottom flask walls.

The methanolic filtrate contained a lot of the powder product that passed through the filter. To improve the yield, the filtrate was passed through the Buchner funnel again and vacuum filtered to collect a second crop of the product. After drying the product, it was dissolved in dichloromethane (128.4 g), transferred to a separatory funnel, and extracted with 126.8 g DI water. Extra dichloromethane (25.2 g) was added to the separatory funnel and the organic layer was washed a second time with DI water (100.0 g). The phases were allowed to separate and the organic phase was rotoevaporated in a round-bottom flask to yield additional 11.3 g of product. The total final product has a weight of 55.4 g and a yield of 86.6%. The procedure is similar to Burlov et al., "Electrochemical synthesis, structure, magnetic and tribochemical properties of metallochelates of new azomethine ligands, bis-[2-(N-tosylaminobenzylidenealkyl(aryl)]disulfides," Russian Journal of General Chemistry 79(3): 401-407 (2009), which is incorporated herein by reference in its entirety, to the extent not inconsistent with the subject matter of this disclosure, but with modifications.

The product was analyzed and the structure was verified by $^{13}$C NMR, $^1$H NMR, and ESI-MS.

Example 5: Synthesis of an Exemplary Functionalized Organosulfur Compound—2,2'-dithiobis[N-(phenylmethylene)]-Ethanamine

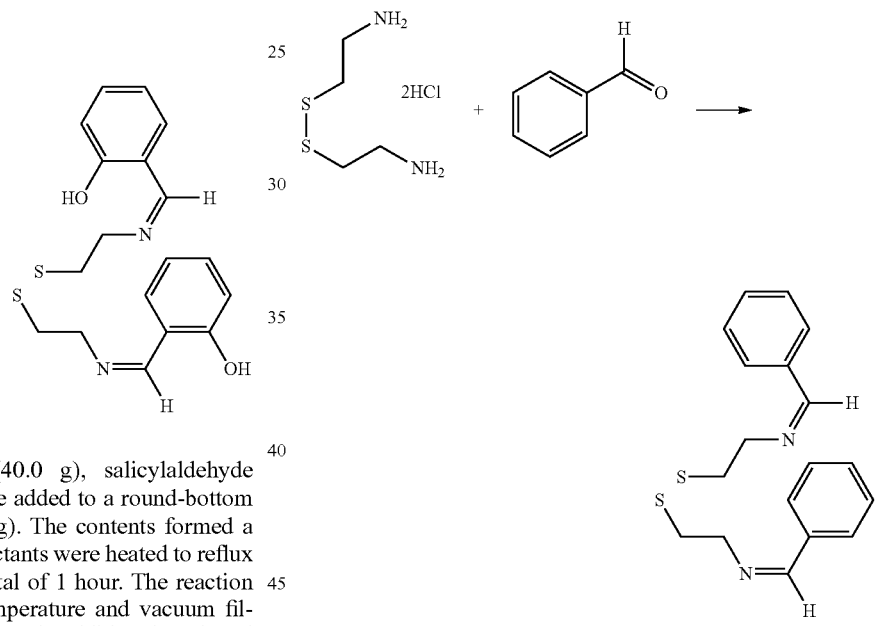

Cystamine dihydrochloride (22.52 g) and benzaldehyde (21.22 g) were added to a 250 ml round-bottom flask. The mixture was stirred with a magnetic stir bar and refluxed for 1.5 hours with a Dean-Stark trap. The reaction mixture was cooled and isopropyl alcohol was added (30 g) to ensure uniform stirring. The reaction mixture was again refluxed for another 3.5 hours. The reaction mixture was then cooled to room temperature and sodium hydroxide (8 g), DI water (36 g), and additional isopropyl alcohol (16 g) were added. The reaction contents were transferred to a separatory funnel. The phases were allowed to separate and the top organic phase was rotoevaporated to yield a dark brown oil. The oil was diluted with dichloromethane (85 g) and extracted with DI water (85 g). After separating the phases and rotoevaporating the organic phase, the resulting product was an oil, with a weight of 26.2 g and a yield of 79.8%.

The product was analyzed and the structure was verified by $^{13}$C NMR and $^1$H NMR.

Example 6: Synthesis of an Exemplary Functionalized Organosulfur Compound—2,2'-dithiobis[N-(4-hydroxy)] benzeneacetamide

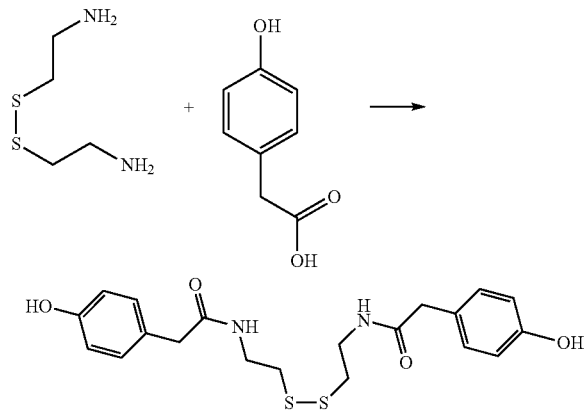

2,2'-diaminodiethyl disulfide dihydrochloride (cystamine dihydrochloride) (210 g) was dissolved in 0.5 L of DI water in a 2 L Erlenmeyer flask. The contents were stirred with a magnetic stir bar, and methanol (1 L) was added during stirring. Sodium hydroxide pellets (76 g) was added and the solution became milky white and exothermed. The contents were stirred for another 2 hours and the resulting NaCl was allowed to settle on the flask bottom. The reaction mixture was filtered through a Buchner funnel. A cake formed on the filter, but a large amount of NaCl still passed through the filter. The filtrate was rotoevaporated and as the solvent was removed, more NaCl continued to precipitate. The contents were filtered again through the same Buchner funnel with the NaCl cake from the first filtration still in it. The NaCl cake was rinsed with cold methanol (20 ml), and the filtrate was rotoevaporated, resulting in a yellow liquid. As more solvent was removed, the color darkened, but there was still a small amount of NaCl in the bottom of the flask. The product was filtered the third time, and the final product, 2,2'-diaminodiethyl disulfide (cystamine), was an oil with a weight of 141.8 g and a yield of 100%.

2,2'-diaminodiethyl disulfide (cystamine) from the above reaction was used to react with 4-hydroxyphenyl acetic acid in the following manner. A 500 ml round-bottom flask was charged with 9.9 g 2,2'-diaminodiethyl disulfide (cystamine), 19.8 g 4-hydroxyphenyl acetic acid, 1.6 g boric acid, and 119.8 g toluene. The reaction mixture was set up for reflux with a Dean Stark trap pre-filled with toluene (19.9 g). The mixture was stirred and heated to reflux (110° C.) and held for 12 hours. The product was a waxy off-white solid insoluble in toluene. The reaction mixture was cooled to room temperature. The toluene was decanted and DI water (75 g) was added to the flask to purify the product. The mixture was filtered through a fritted Buchner funnel and was washed with n-heptane (127 g). The solid product on the filter was dissolved in a minimal volume of methanol, while the white insoluble powder was filtered off. After rotoevaporating the methanol and drying, the product weighed 16.7 g with a yield of 61.1%.

The formation of the amide bond was confirmed by FT-IR.

Example 7A: Synthesis of an Exemplary Functionalized Organosulfur Compound—2,2'-dithiobis[N-(4-hydroxy)]phenylstearylacetamide

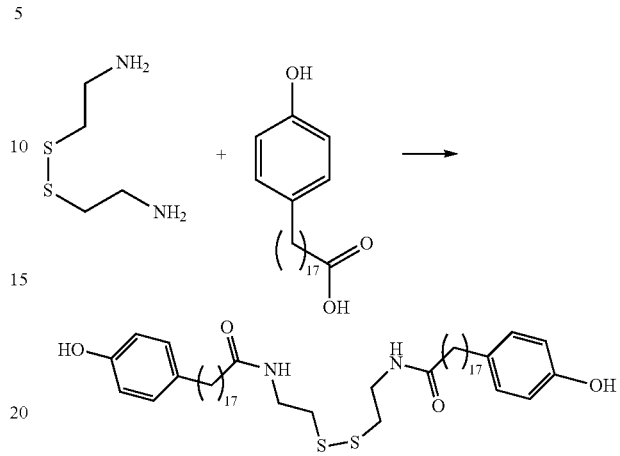

2,2'-diaminodiethyl disulfide (cystamine) (17.4 g) was added to a 500 ml round-bottom flask along with phenol stearic acid (manufactured by SI Group) (198.9 g), boric acid (1.4 g), and xylene (10 g). The reaction was set up for reflux and heated to 115° C. for 2 hours and then to 145° C. over the next 1.5 hours or until the reaction was complete, while stirring. The contents were cooled to room temperature, dissolved in xylene (296.4 g), and transferred to a separatory funnel. The crude product was extracted with DI water (100 g). The phases were allowed to separate and the organic phase was washed again with DI water (122 g). The product was rotoevaporated to yield a viscous liquid product, containing residual xylene. After correction for residual solvent, the product weighed 200.9 g with a yield of 94.7%.

The product formation was confirmed by FT-IR.

Example 7B: Synthesis of a Modified Phenolic Novolac Resin 2,2'-dithiobis[N-(4-hydroxy)]phenylstearylacetamide, the functionalized organosulfur compound prepared in Example 7A, can be coupled with the phenolic resin in two different methods.

Method I.

In this method type, the phenolic moiety of the compound is methylolayted with formaldehyde. Then, the methylolated compound is added to the rubber composition and can be coupled to the phenolic moiety of the phenolic resin during rubber mixing.

The reagent 2,2'-dithiobis[N-(4-hydroxy)]phenylstearylacetamide (13.0 g), the functionalized organosulfur compound prepared in Example 7A, was added to a round-bottom flask along with a base catalyst (triethylamine, 3.0 g) and heated to 55-60° C. Then, a 50 wt % formaldehyde solution was added dropwise (3.6 g) to the flask and allowed to react for 2.5 hours.

The methylolated reagent was then isolated by vacuum distillation at 60° C. and added directly to the rubber mixer.

Method II.

In this method type, the phenolic moiety of the compound is methylolayted with formaldehyde. Then, the methylolated compound is added to the phenolic resin and condensed with the phenolic resin.

The reagent 2,2'-dithiobis[N-(4-hydroxy)]phenylstearylacetamide (13.0 g), the functionalized organosulfur compound prepared in Example 7A, was added to a round-bottom flask along with a base catalyst (triethylamine, 3.0 g) and heated to 55-60° C. Then, a 50 wt % formaldehyde solution was added dropwise (3.6 g) to the flask and allowed to react for 2.5 hours.

A phenol novolac resin pellets (SI Group HRJ-12952, 130 g) was then added to the flask. The resin pellets were melted by heating to 137° C. The reaction mixture was vacuum distilled to remove water by heating to 180° C. The modified resin was isolated by pouring it into a metal pan. After allowing the resin to cool down to form a solid material, the product weighed 141.3 g with a yield of 98.3%.

Example 8: Synthesis of an Exemplary Functionalized Organosulfur Compound—2,2'-dithiobis[N(4-hydroxy-γ-(4-hydroxyphenyl)-γ-methyl)] Benzenebutanamide

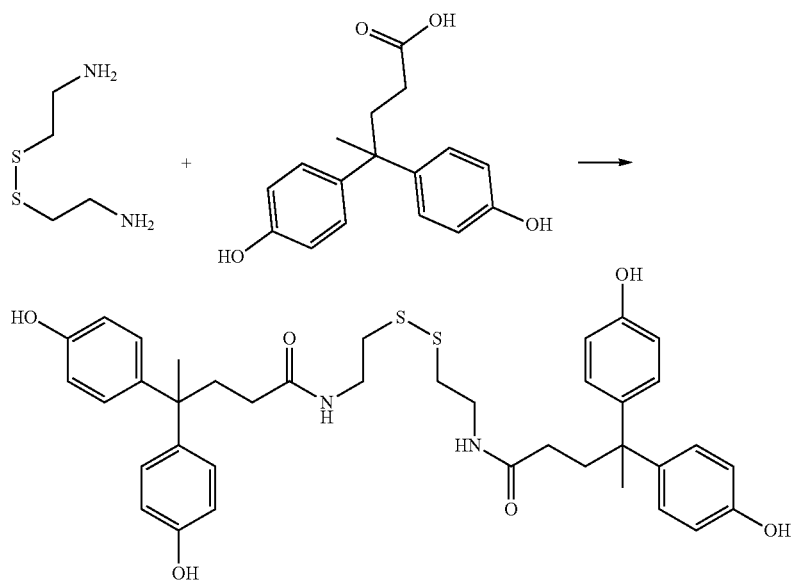

A 500 ml round-bottom flask was charged with 2,2'-diaminodiethyl disulfide (cystamine, 11.4 g), 4,4-bis-(4-hydroxyphenyl) valeric acid (42.9 g), N,N'-dicyclohexylcarbodiimide catalyst (3.9 g), xylene (60.4 g) and DI water (10.2 g). The reaction was set up for reflux with a Dean-Stark trap. The contents were stirred and heated to reflux for 2 hours at 98° C. The reaction was cooled to room temperature and methanol (40.2 g) was added. The contents of the flask were heated to 71-76° C. at mild reflux for another 1 hour. After cooling the reaction mixture to room temperature, the reaction product formed a cake on the bottom of the flask. After decanting the solvent, the product was dissolved in a minimal amount of acetone. There was a small amount of insoluble white powder in the acetone solution and was filtered off. After rotoevaporating the acetone, the final product weighed 50.5 g, with a yield of 97.7%.

Thin layer chromatography on silica gel showed no unreacted 4,4-bis-(4-hydroxyphenyl) valeric acid in the purified material, which was further confirmed by FT-IR. The formation of the amide product was confirmed by GC-MS and LC-MS.

Example 9: Pilot Process for Preparing an Exemplary Functionalized Organosulfur Compound—2,2'-[dithiobis(2,1-ethanediylnitriloethylidyne)]bisphenol

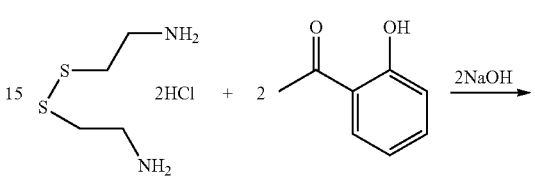

-continued

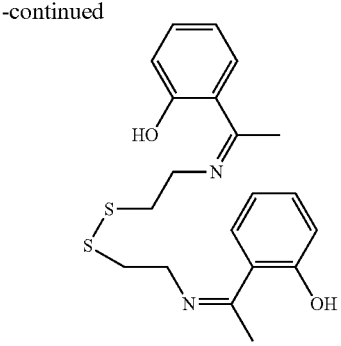

Cystamine dihydrochloride (18.2 lbs) was pre-mixed with distilled water (43.9 lbs) and the resulting solution was loaded to a kettle. Isopropyl alcohol (113.3 lbs) and 2'-hydroxyacetophenone (22.0 lbs) were loaded to the kettle, and the addition lines were rinsed with distilled water (10.0 lbs). The kettle was agitated with an agitation at 175 rpm. The batch was heated to 34-36° C., and 50% sodium hydroxide (4.45 lbs) was loaded at a rate of 1 lb/minute. Then, immediately after, a diluted sodium hydroxide solution (pre-mixing 50% sodium hydroxide (8.58 lbs) with distilled water (55.0 lbs)) was loaded at a rate of 6 lbs/minute. Distilled water (7.0 lbs) was then loaded to rinse the addition lines. The batch was agitated for 120 minutes at a batch temperature of 34-36° C. After that, a sample was obtained to determine the 2'-hydroxyacetophenone (HAP) content in the batch.

When the HAP content in the batch was less than 1.5 wt %, the reaction mixture was transferred to a Nutsche filter and filtered to remove mother liquor. Once the mother liquor was removed, the resulting cake was washed for 1 hour with distilled water (93.1 lbs). The water was removed by filtration. Isopropyl alcohol (47.0 lbs) was added to the water-washed cake and the cake was washed via displacement. Isopropyl alcohol and residuals were drained. The steps of isopropyl alcohol-washing and filtration were repeated.

The resulting cake was dried by heating the Nutsche rake and jacket to 50° C. and placing the batch under vacuum while the rake span. The product was dried until the solid content of the product reaches >98 wt %.

Example 10: Pilot Process for Preparing a Modified Phenolic Novolac Resin

A phenol novolac resin (SI Group HRJ-12952, a reinforcing resin, 385 lbs) was melted until molten and stirrable. The content was stirred at 80 rpm and the resin was heated to 155-160° C. The functionalized organosulfur compound, 2,2'-[dithiobis(2,1-ethanediylnitriloethylidyne)]bis-phenol, prepared in Example 9, was added to the batch at 155-160° C. over the course of 20 minutes. After the compound was loaded, the temperature was maintained and the batch was stirred for 30 minutes. The resulting modified resin was then dropped to a pan and allowed to cool.

Example 11: Rubber Formulations

Sample Preparation for the Application Test

A master batch rubber compound formulated for the apex of a tire was used for performance application testing of the rubber containing the functionalized organosulfur compounds. The tire shoulder, located between the tread and sidewall, requires reinforcement for stiffness and a lowered hysteresis would aid in improving the wear on the tire and rolling resistance of the vehicle.

The master batch rubber was made according to the formula shown in Table 2.

TABLE 2

Master batch rubber formulation

| Ingredient: | Loading (phr): |
| --- | --- |
| SMR 20 (Smoked Malaysian Rubber) | 100.00 |
| Zinc Oxide | 3.50 |
| Stearic Acid | 3.00 |
| Carbon Black, N375 | 22.50 |
| Carbon Black, N660 | 22.50 |
| Antiozonant 6PPD | 1.20 |
| Antioxidant TMQ (RD) | 0.50 |
| Total master batch | 153.20 |

For individual shoulder formulation samples, the master batch was mixed with other components (which varies by each sample, see Table 3 below) in a Banbury mixer, followed by addition of the cure package which includes insoluble sulfur (1.70 phr) and N-tert-butyl-benzothiazole sulfonamide (TBBS) sulfur accelerator (1.40 phr). For the samples containing a phenolic novolac resin, the resin was mixed into the master batch at 10.00 phr, and hexakis (methoxymethyl)-melamine (HMMM) crosslinker was mixed into the master batch at 1.30 phr.

The following five samples listed in Table 3 were tested for the performance application testing. A reinforcing resin (SI Group HRJ-12952) was used for the phenol novolac resin in Table 3. Compound 2,2'-[dithiobis(2,1-ethanediyl-nitriloethylidyne)]bis-phenol, prepared according to Example 1A (or 1A'), was used for the functionalized organosulfur compound in Table 3. A phenol novolac resin pre-mixed with and modified by a functionalized organosulfur compound, prepared according to Example 1B, was used for the modified phenol novolac resin in Table 3.

TABLE 3

Shoulder formulation samples

| Sample | Description |
| --- | --- |
| Blank | Master batch rubber prepared according to Table 2, plus a cure package including sulfur and sulfur accelerator (but without a phenol novolac resin, without a functionalized organosulfur compound, and without a crosslinker) |
| Control resin | Master batch rubber prepared according to Table 2, plus a cure package including sulfur and sulfur accelerator and a HMMM crosslinker, and plus a phenol novolac resin. |
| Modified phenol novolac resin (M-resin) | Master batch rubber prepared according to Table 2, plus a cure package including sulfur and sulfur accelerator and a HMMM crosslinker, and plus a modified phenol novolac resin. |
| Mixing a functionalized organosulfur compound followed by a resin (S-compound/resin) | Master batch rubber prepared according to Table 2, plus a cure package including sulfur and sulfur accelerator and a HMMM crosslinker, plus a functionalized organosulfur compound added first during Banbury mixing followed by a phenol novolac resin. |
| Mixing a resin followed by a functionalized organosulfur compound (Resin/S-compound) | Master batch rubber prepared according to Table 2, plus a cure package including sulfur and sulfur accelerator and a HMMM crosslinker, plus a phenol novolac resin added first during Banbury mixing followed by a functionalized organosulfur compound. |

Rubber Sample Preparation Via Banbury Mixing

For each sample shown in Table 3, the procedure below was followed to prepare the five individual rubber compound samples. First, the rotors and mixing chamber were set to 60° C. The rotors were turned on to 50 rpm and the ram was moved to upper position. The master batch rubber (153.20 phr) was loaded and mixed for 30 seconds. Then a resin or a combination of resin and functionalized organosulfur compound, depending on the individual sample (as shown in Table 3), was loaded. The cure package was then loaded and the ram was dropped and mixed for 240 seconds. The rubber sample was then automatically dropped to the collection bin. As shown in Table 3, in the case of the Blank sample, no phenolic resin, functionalized organosulfur compound, or a crosslinker was used.

For each sample, the cure package contained insoluble sulfur (1.7 phr) and TBBS sulfur accelerator (1.4 phr). For the samples containing the resin, the cure package also contained HMMM crosslinker (1.3 phr) (see Table 3). For the modified phenol novolac resin, the resin was loaded in the rubber at 10 phr. For the samples where the functionalized organosulfur compound and the phenol novolac resin were loaded separately into Banbury mixer, 1 phr of functionalized organosulfur compound was used and 9 phr of phenol novolac resin was used.

Following Banbury mixing, each rubber sample was then further mixed on a two-roller mill according to the following procedure. A two-roller mill was pre-heated to 100-110° F. (approximately 43° C.) the adjustment knobs for sheet thickness were set to 0 degrees. The mill rollers were started at 13.7 rpm. The rubber sample was then placed between the two rollers and the rubber passed through the mill and banded the front roller. The rubber on the front roller was cut multiple times: a first cut was made right-to-left and the rubber was stretched off of the roller and then fed back in; a second cut was made left-to-right followed by stretching and re-feeding the material back onto the mill. This cutting process was repeated three times for a total of six cuts over a 4 minute period. The rubber was then sheeted and the appropriate test specimens were produced from the rubber sheet.

RPA Sample Preparation

To obtain cure data, square samples (approximately 5 g and 50 mm×50 mm) were run on the RPA 2000 (Alpha Technologies).

RPA: MDR 160 C Test Procedure

Samples were placed between two mylar film sheets, and then placed on the bottom RPA 2000 die. 160 C test process was followed to determine cure time and torque. The sample was run for 30 minutes and was heated to 160° C. at 1.7 Hz, 6.98% strain to yield cure data, such as T90, which was used to cure samples for other tests.

Mixing Viscosity

The results of the mixing viscosity of each sample are shown in FIG. 1. The mixing viscosity was characterized by pre-cure Strain Sweep n* at 100° C., 1.0 Hz, and was plotted as a function of strain angle.

FIG. 1 shows that the mixing viscosity for the rubber sample prepared with the modified phenol novolac resin (M-resin) was very similar to the mixing viscosity for the rubber sample prepared with the unmodified phenol novolac resin (Control resin). The pre-cure viscosities of the two rubber samples where a functionalized organosulfur compound and a resin were separately mixed in Banbury mixer (S-compound/resin and Resin/S-compound) were lower than the viscosity of the rubber sample where the functionalized organosulfur compound and resin were pre-mixed. The rubber sample prepared with the functionalized organosulfur compound added to the Banbury mixer first followed by the resin (S-compound/resin) appeared to have a lower mixing viscosity than all other rubber samples, except the Blank, indicating that the order of adding various additives (e.g., the order of adding the functionalized organosulfur compound and the resin) could affect the mixing viscosity of the rubber formulation.

Cure Characteristics

Figure 2:
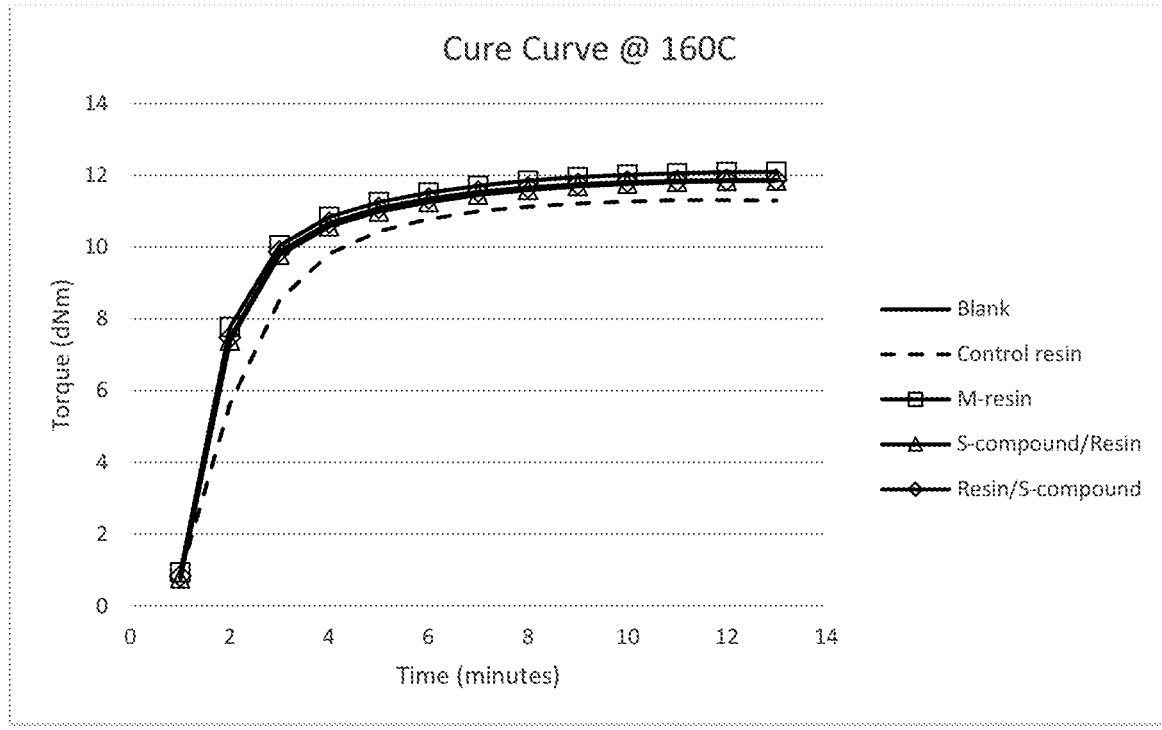
FIG. 2 shows the curing property for each rubber sample, characterized by torque at 160° C. as a function of time. The rubber samples are described in Table 3.

The curing properties of each sample are shown in FIG. 2. The samples were cured at 160° C. for 30 minutes at 1.7 Hz, 6.98% strain, and the curing curve was plotted as a function of time.

FIG. 2 shows that each rubber sample exhibited similar cure properties. The rubber samples containing the resin and the functionalized organosulfur compound, including the one having the modified phenol novolac resin (M-resin) and those where the functionalized organosulfur compound and the resin were separately mixed in Banbury mixer (S-compound/resin and Resin/S-compound), exhibited a higher crosslink density than the rubber sample containing only the unmodified phenol novolac resin (Control resin).

Tensile Properties

The rubber sheet was remilled to make ASTM D412 tensile bars, with the dials rotated 40 degrees counter clockwise to 60 mm. The sample was run back through and milled into a 2 mm rectangular sheet. An ASTM D412 die was used to cut the plaque that eventually became tensile bars. The cut samples were placed in 150 mm×150 mm square cavities. Samples were cured based on T90+4 minutes. After samples were removed, the tensile bars were cut using a die.

Samples were tested using ASTM D412 method A and an Instron model 5965 universal tensile testing machine (Instron). The video extensimeter (AVE model 2663-901) for recording stress/strain data from the marked cross sectional was calibrated prior to testing. The specimen were marked with two white dots 5 mm apart using a jig. These two small dots represent the test cross section area tested. Samples were then placed in 1 kN pneumatic grips, using a 5 kN load cell to displace the samples for stress/strain calculations.

Figure 3:
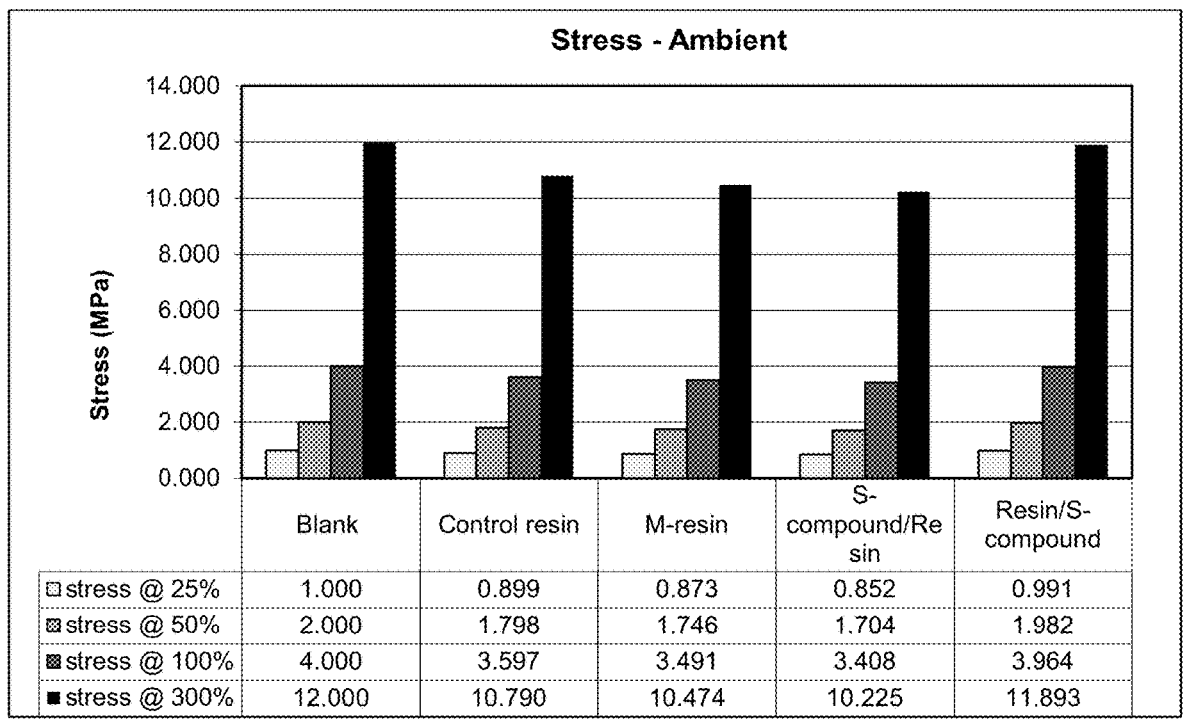
FIG. 3 shows the tensile stress at given strains for each rubber sample. The rubber samples are described in Table 3.

The results of the tensile stresses at given strains for the rubber samples are shown in FIG. 3. The tensile stresses of the various rubber samples were comparable at the test temperature, albeit minor differences between the samples.

Figure 4:
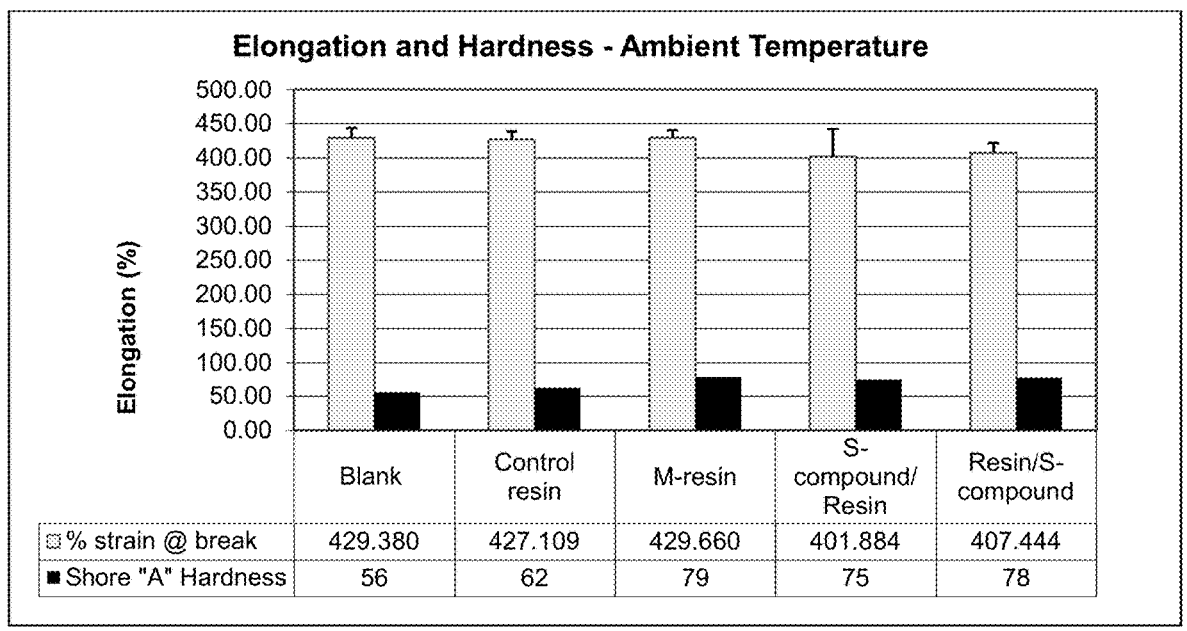
FIG. 4 shows the tensile elongation for each rubber sample. The rubber samples are described in Table 3.

The results of the tensile elongations for the rubber samples are shown in FIG. 4. The elongations of the various rubber samples were comparable at the test temperature, albeit slightly reduced elongations for the rubber samples where the functionalized organosulfur compound and the resin were separately mixed in Banbury mixer (S-compound/resin and Resin/S-compound).

Dynamic Properties

Testing for dynamic properties of the rubber samples was performed on a rubber process analyzer (RPA) at 100-110° C. and 10 Hz after cure. The samples were subjected to 4 strain sweeps. Samples produced G' elastic response modulus, G" viscous response modulus, and the ratio of elastic modulus over viscous modulus to arrive at the Tan D values. The results summarized in FIGS. 5A-5C were produced from the $3^{rd}$ strain.

Figure 5A:
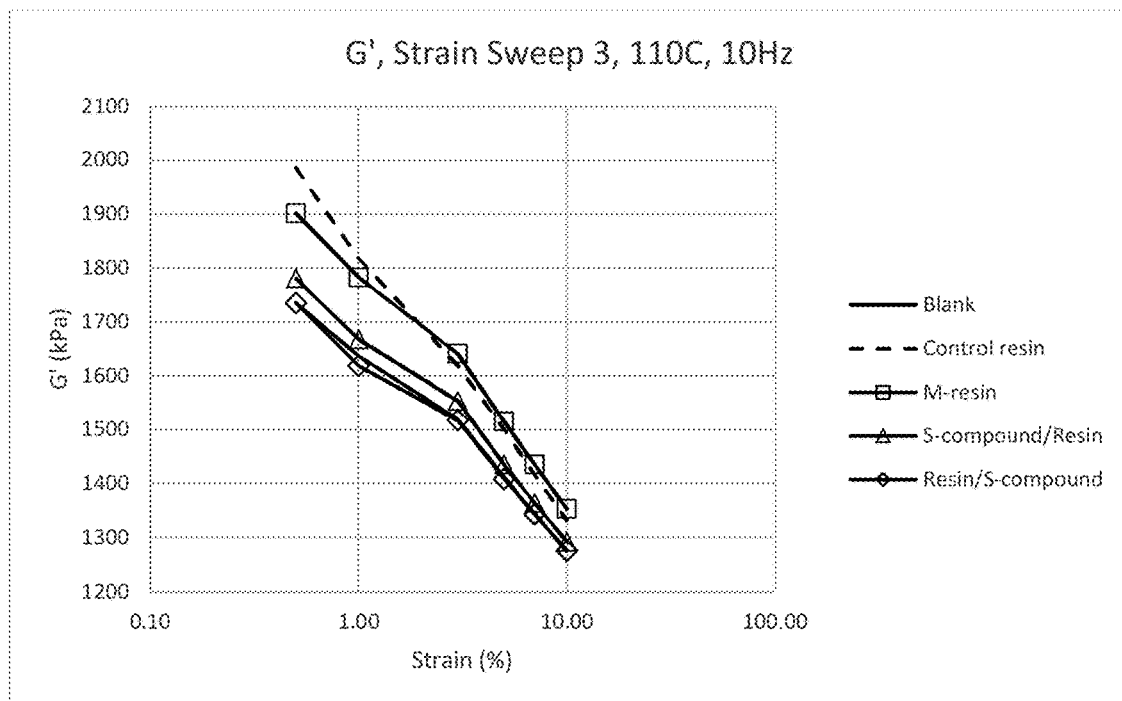
FIGS. 5A-5C show the dynamic properties, measured on a rubber process analyzer (RPA) at 100-110° C. and 10 Hz after cure, for each rubber sample.
Figure 5B:
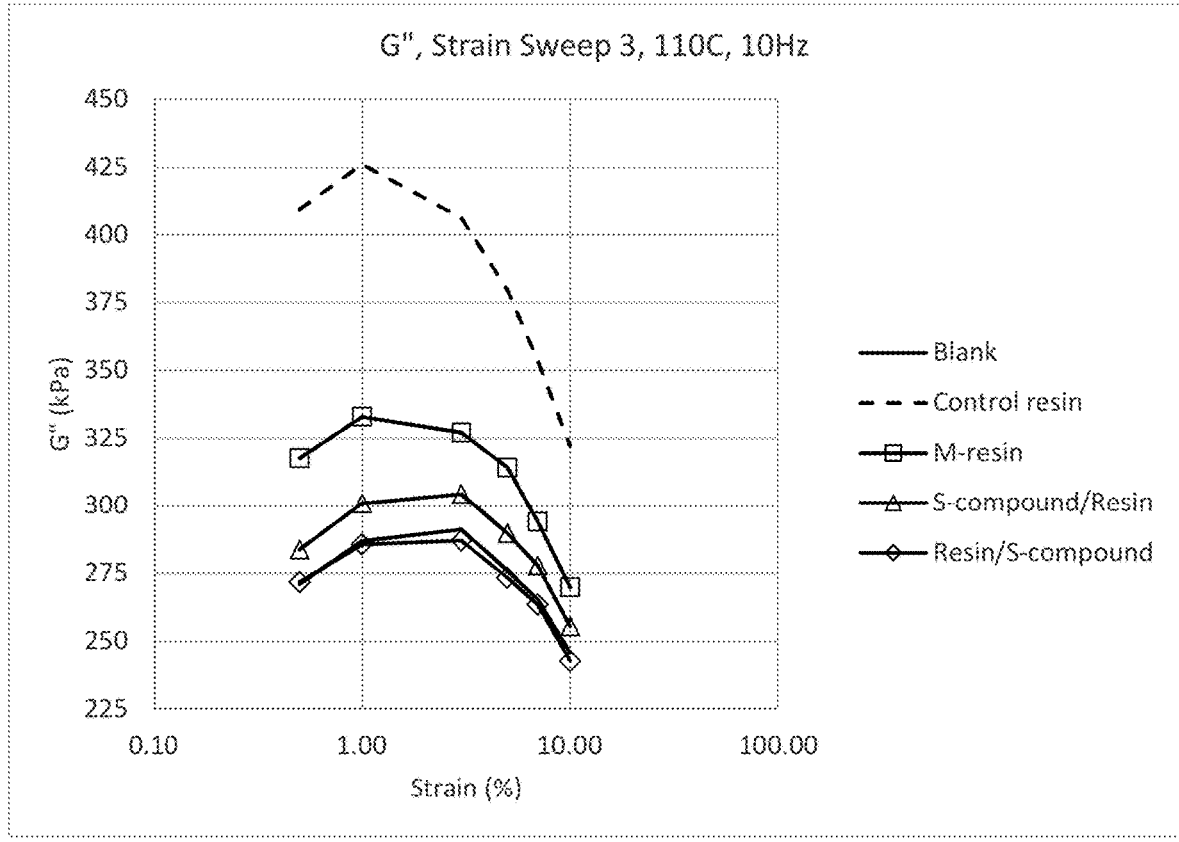
Figure 5C:
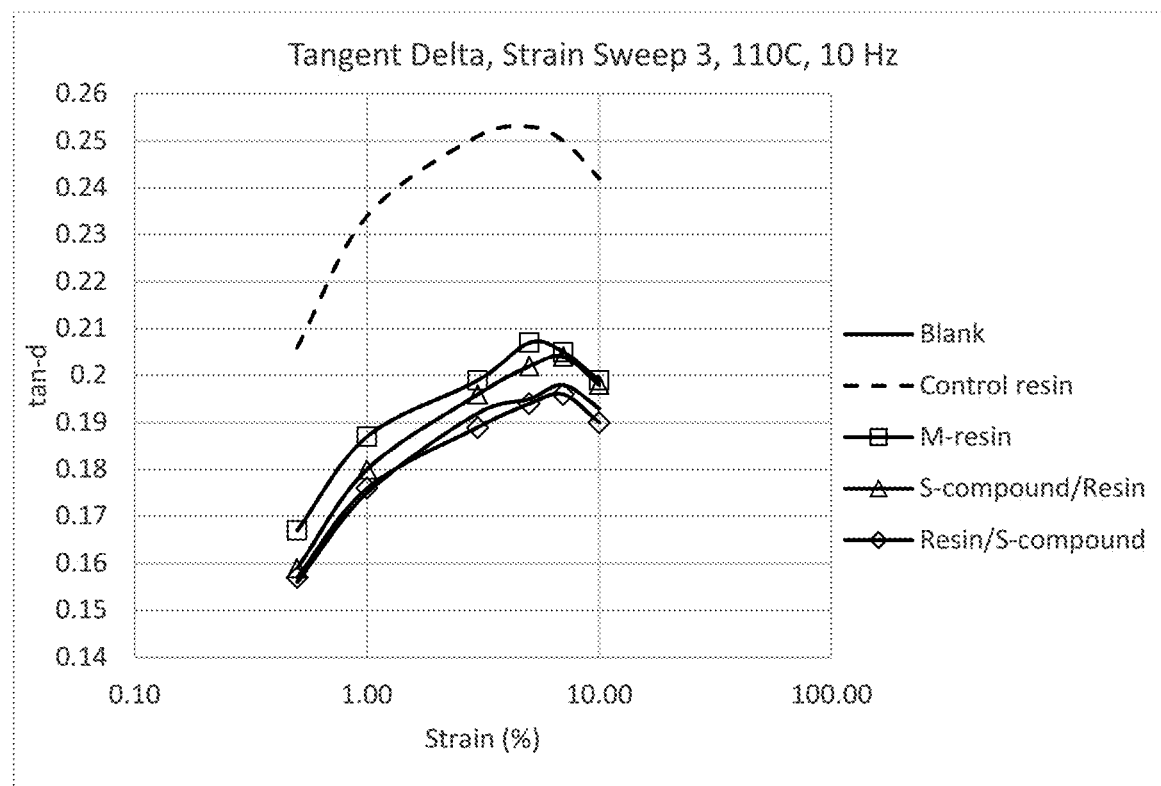

As shown in FIG. 5C, the dynamic properties of the rubber samples containing the functionalized organosulfur compound, including the one having the modified phenol novolac resin (M-resin) and those where the functionalized organosulfur compound and the resin were separately mixed in Banbury mixer (S-compound/resin and Resin/S-compound), all showed a significant improvement over the rubber sample containing only the unmodified phenol novolac resin (Control resin), and started to resemble the dynamic properties of the Blank rubber sample containing no functionalized organosulfur compound. This is an improved performance for rubber articles, because the Blank rubber sample had the lowest Tan D and the lowest heat build-up of among the rubber samples tested.

As shown in FIG. 5A, the elastic modulus, G', of the rubber sample containing the modified phenol novolac resin (M-resin) showed little change over all strain angles, as compared to that of the rubber sample containing the unmodified phenol novolac resin (Control resin). The rubber samples where the functionalized organosulfur compound and the resin were separately mixed in Banbury mixer (S-compound/resin and Resin/S-compound) showed a decrease in G' of approximately 3-13%, as compared to that of the rubber sample containing only the phenol novolac resin (Control resin).

As shown in FIG. 5B, the rubber samples containing the functionalized organosulfur compound, including the one having the modified phenol novolac resin (M-resin) and those where the functionalized organosulfur compound and the resin were separately mixed in Banbury mixer (S-compound/resin and Resin/S-compound), all showed a drop in the viscous modulus, G", of approximately 20-30%, as compared to that of the rubber sample containing only the phenol novolac resin (Control resin).

Additionally, the rubber samples where the functionalized organosulfur compound and the resin were separately mixed in during Banbury mixing (S-compound/resin and Resin/S-compound) showed a larger drop in G" than the rubber sample where the resin was pre-mixed with the functionalized organosulfur compound (M-resin). The drop in G" had a direct correlation to the reduction in Tan D for each rubber sample and a direct correlation to a lower hysteresis for the rubber samples. This indicates that separately mixing in the functionalized organosulfur compound and the resin during Banbury mixer would produce a rubber sample with a better performance in this regard than pre-mixing the molten resin with the functionalized organosulfur compound.

The results of the dynamic (RPA) tests in this example (FIGS. 5A-5C), particularly Tan D values shown in FIG. 5C, correlated well with the heat build-up (HBU) values determined by flexometry (FIG. 6), as discussed in the section below.

Heat Build-Up Measured by a Flexometer

The rubber sheet was remilled and a rectangular sheet was used to make flexometer ASTM D623 samples. Samples for testing were made using a CCSI die approximately 25 mm in height and a CCSI triplate 8 cavity mold with cavities 25 mm in height, 17 mm in diameter. The samples were pressed in a heated hydraulic press according to T90+10 min specifications. Before placing samples in the mold, the heated press was heated to 160° C., and the CCSI mold was preheated to 160° C. After coming off the mill the sample rubber sheet was approximately 300 mm in width and 350 mm in length. The sheet was folded in half four times, and the die was then used to punch three separate punches from the folded rubber sheet to fill the 25 mm cavity in the triplate mold. Each of the three individual punches were packed into the mold cavity, a piece of foil was placed on top, and the top of the triplate was assembled to the mold. The samples were then cured for a time of T90+10 minutes. The mold was then removed from the press, and the samples were removed from the mold cavities and allowed to cool to room temperature.

Samples for heat generation were tested based on ASTM D623 with some slight modifications, as noted below. The test was run on EKT-2002GF (Ektron). The weight of 160N and a frequency of 33 Hz were used. The permanent (flex fatigue) set calculations were also based on ASTM D623 specifications, using a micrometer.

Figure 6:
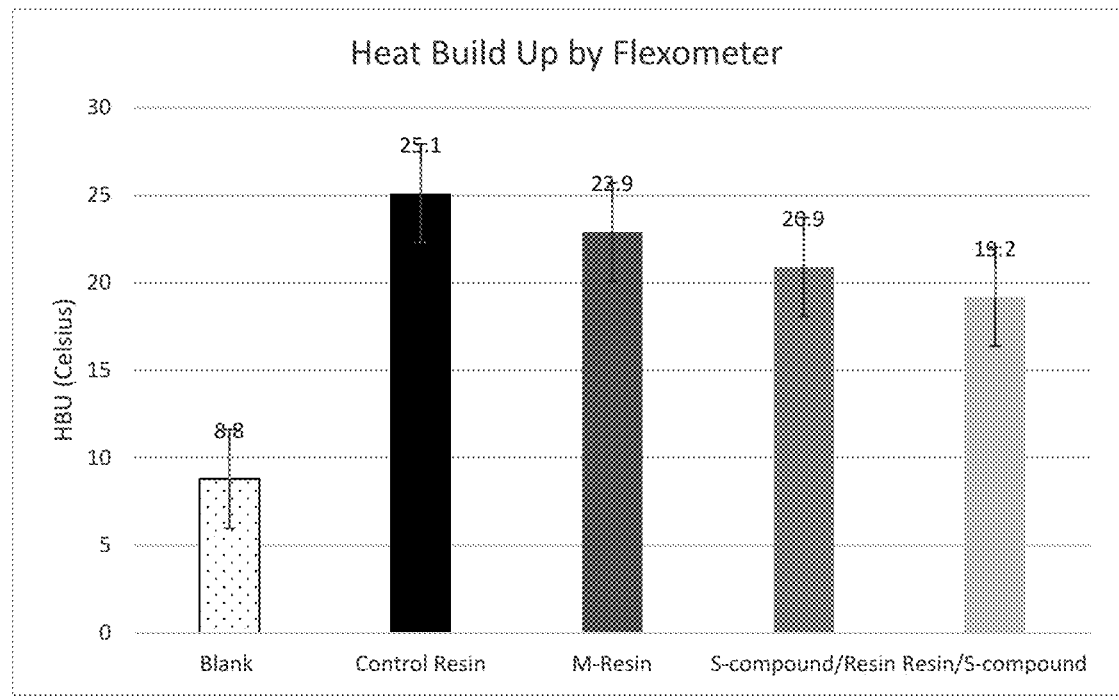
FIG. 6 shows the heat build-up, measured by a flexometer, for each rubber sample. The rubber samples are described in Table 3.

The results of heat build-up (HBU) from a series of 3 runs were averaged and summarized in FIG. 6.

As shown in FIG. 6, the rubber samples containing the functionalized organosulfur compound, including the one having the modified phenol novolac resin (M-resin) and those where the functionalized organosulfur compound and the resin were separately mixed in Banbury mixer (S-compound/resin and Resin/S-compound), all showed a significant improvement in the HBU, as compared to that of the rubber sample containing only the phenol novolac resin (Control resin). Additionally, the rubber samples where the functionalized organosulfur compound and the resin were separately mixed in during Banbury mixing (S-compound/resin and Resin/S-compound) showed a lower HBU than the rubber sample where the resin was pre-mixed with the functionalized organosulfur compound (M-resin).

Example 12: Rubber Formulations

Sample Preparation for the Application Test

A scratch-mixed rubber compound formulated for the apex of a tire was used for performance application testing of the rubber containing the functionalized organosulfur compounds. The tire apex, also known as the bead, requires reinforcement for stiffness and a lowered hysteresis would aid in improving the wear on the tire and rolling resistance of the vehicle.

The scratch-mixed rubber compound containing a phenolic resin or a modified phenolic resin (Samples 2, 3, 10, 11 in Table 5) was made according to the formula shown in Table 4a.

TABLE 4a

Scratch-mixed rubber formulation for an apex compound containing a phenolic resin (or a modified phenolic resin)

| Ingredient | Loading (phr) |
|---|---|
| Natural rubber (SMR20) | 100.00 |
| Carbon black (N330) | 68.00 |
| Stearic acid | 2.00 |
| Zinc oxide | 4.00 |
| Aromatic oil | 2.00 |
| Antioxidant 6PPD (4020) | 3.00 |
| Phenolic resin | 10.00 |
| TBBS | 1.40 |
| Insoluble sulfur | 4.00 |
| HMMM | 1.30 |
| TOTAL: | 195.70 |

The scratch-mixed rubber compound containing a phenolic resin and a functionalized organosulfur compound, added separately (Samples 4-9 in Table 5), was made according to the formula shown in Table 4b.

TABLE 4b

Scratch-mixed rubber formulation for an apex compound containing a phenolic resin and a functionalized organosulfur compound, added separately during mixing

| Ingredient: | Loading (phr): |
|---|---|
| Natural rubber (SMR20) | 100.00 |
| Carbon Black (N330) | 68.00 |
| Stearic Acid | 2.00 |
| Zinc Oxide | 4.00 |
| Aromatic Oil | 2.00 |
| Antioxidant 6PPD (4020) | 3.00 |
| Phenolic resin | 9.00 |
| Functionalized organosulfur compound | 1.00 |
| Insoluble sulfur | 4.00 |
| TBBS | 1.40 |
| HMMM | 1.30 |
| TOTAL: | 195.70 |

For individual apex formulation samples, a two-pass mixing procedure was followed. During the first (hot) pass, a master batch was prepared and consisted of natural rubber, carbon black, stearic acid, zinc oxide, aromatic oil, and antioxidant in the amounts listed in Table 4a or Table 4b. For some of the samples, a phenol novolac resin (or a modified phenolic novolac resin, M-resin) and/or a functionalized organosulfur compound (S-compound) was mixed into the masterbatch during hot pass mixing. The master batch compound was allowed to cool and sit overnight. During the second (cold) pass, insoluble sulfur, N-tert-butyl-benzothiazole sulfonamide (TBBS), and hexakis(methoxymethyl)-melamine (HMMM) were added to the sample. For some of the samples, M-resin and/or S-compound were mixed into the rubber compound during the second pass. See Table 5 for individual sample recipes. A Banbury mixer was used to prepare all samples. For the samples containing a phenolic novolac resin, the resin was mixed into the compound at 10.00 phr. For the samples containing the S-compound, the additive was mixed into the compound at 1.0 phr.

The following eleven samples listed in Table 5 were tested for the performance application testing. A reinforcing resin (SI Group HRJ-12952) was used for the phenol novolac resin in Table 5. Compound 2,2'-[dithiobis(2,1-ethanediyl-nitriloethylidyne)]bis-phenol, prepared according to Example 1A (or 1A'), was used for the functionalized organosulfur compound (S-compound) in Table 5. A phenol novolac resin pre-mixed with and modified by a functionalized organosulfur compound, prepared according to Example 1B, was used for the modified phenol novolac resin (M-resin) in Table 5.

TABLE 5

Scratch-mixed apex compound descriptions.

| Sample Number | Sample Name | Description |
|---|---|---|
| 1 | Blank | Rubber compound prepared according to Table 4a, (but without a phenol novolac resin, without a functionalized organosulfur compound, and without a crosslinker) |
| 2 | Control resin (Hot Pass) | Rubber compound prepared according to Table 4a, having a phenol novolac resin added during the hot pass. |
| 3 | Control resin (Cold Pass) | Rubber compound prepared according to Table 4a, having a phenol novolac resin added during the cold pass. |
| 4 | Mixing a functionalized organosulfur compound during hot pass followed by a resin in the hot pass (S-compound H/Resin H) | Rubber compound prepared according to Table 4b, having a functionalized organosulfur compound added first during hot pass Banbury mixing followed by a phenol novolac resin added during hot pass Banbury mixing. |
| 5 | Mixing a functionalized organosulfur compound during cold pass followed by a resin in the cold pass (S-compound C/Resin C) | Rubber compound prepared according to Table 4b, having a functionalized organosulfur compound added first during cold pass Banbury mixing followed by a phenol novolac resin added during cold pass Banbury mixing. |
| 6 | Mixing a resin in the hot pass followed by a functionalized organosulfur compound during hot pass (Resin H/S-compound H) | Rubber compound prepared according to Table 4b, having a phenol novolac resin added first during hot pass Banbury mixing followed by a functionalized organosulfur compound added during hot pass Banbury mixing. |
| 7 | Mixing a resin in the cold pass followed by a functionalized organosulfur compound during cold pass (Resin C/S-compound C) | Rubber compound prepared according to Table 4b, having a phenol novolac resin added first during cold pass Banbury mixing followed by a functionalized organosulfur compound added during cold pass Banbury mixing. |
| 8 | Mixing a functionalized organosulfur compound in the hot pass followed by a resin during cold pass (S-compound H/Resin C) | Rubber compound prepared according to Table 4b, having a functionalized organosulfur compound added during hot pass Banbury mixing, followed by a phenol novolac resin added during cold pass Banbury mixing. |
| 9 | Mixing a resin in the hot pass followed by a functionalized organosulfur compound during cold pass (Resin H/S-compound C) | Rubber compound prepared according to Table 4b, having a phenol novolac resin added during hot pass Banbury mixing, followed by a functionalized organosulfur compound added during cold pass Banbury mixing. |
| 10 | Modified phenol novolac resin in the hot pass (M-resin H) | Rubber compound prepared according to Table 4a, having a modified phenol novolac resin added during hot pass Banbury mixing. |
| 11 | Modified phenol novolac resin in the cold pass (M-resin C) | Rubber compound prepared according to Table 4a, having a modified phenol novolac resin added during cold pass Banbury mixing. |

Rubber Sample Preparation Via Banbury Mixing

The rotors and mixing chamber were set to 60° C. The rotors were turned on to 50 rpm and the ram was moved to upper position. The natural rubber 644 g grams, 100 phr) was loaded and mixed for 30 seconds. For each rubber sample, the stearic acid, zinc oxide, and antioxidant, carbon black, and aromatic oil were each added, along with the S-compound and/or phenol novolac resin (or modified phenol novolac resin) if included during this mixing step (see Table 5), were loaded. The ram was dropped and mixed for 240 seconds.

The hot pass rubber compound was then moved to a two-roller mill pre-heated to 100° C. and the adjustment knobs for sheet thickness were set to 0 degrees. The mill rollers were started at 13.7 rpm. The rubber sample was then placed between the two rollers and the rubber passed through the mill and banded the front roller. The rubber on the front roller was cut multiple times: a first cut was made right-to-left and the rubber was stretched off of the roller and then fed back in; a second cut was made left-to-right followed by stretching and re-feeding the material back onto the mill. This cutting process was repeated three times for a total of six cuts over a 4 minute period. The rubber was then sheeted and allowed to sit overnight.

During the second pass of a mixing the sample prepared the day before was loaded to the Banbury mixer and allowed to mix at 60° C. for 30 seconds and 50 rpm. The cure package, or the cure package with modified phenolic novolac resin, or the cure package with a combination of a S-compound and/or phenol novolac resin, are added to the rubber in the Banbury mixer and mixed at 100 rpm for two minutes and twenty seconds. See Table 5 for sample descriptions.

For each sample, the cure package contained insoluble sulfur (4.0 phr) and TBBS sulfur accelerator (1.8 phr). For the samples containing the modified resin, the S-compound, or the phenol novolac resin, the cure package also contained HMMM crosslinker (1.3 phr) (see Tables 4a and 4b). For the samples where the functionalized organosulfur compound and the phenol novolac resin were loaded separately into Banbury mixer, 1.0 phr of functionalized organosulfur compound was used and 9.0 phr of phenol novolac resin was used. For the samples containing the modified novolac resin (M-resin, Table 5), 10 phr of modified novolac resin was used.

Following the second pass of Banbury mixing, each rubber sample was then further mixed on a two-roller mill according to the following procedure. A two-roller mill was pre-heated to 100-110° F. ° C. and the adjustment knobs for sheet thickness were set to 0 degrees. The mill rollers were started at 13.7 rpm. The rubber sample was then placed between the two rollers and the rubber passed through the mill and banded the front roller. The rubber on the front roller was cut multiple times: a first cut was made right-to-left and the rubber was stretched off of the roller and then fed back in; a second cut was made left-to-right followed by stretching and re-feeding the material back onto the mill. This cutting process was repeated three times for a total of six cuts over a 4 minute period. The rubber was then sheeted and the appropriate test specimens were produced from the rubber sheet.

1. Sample Preparation for RPA Testing

Samples for Rubber Process Analyzer, RPA 2000 (Alpha Technologies) were prepared in the following manner: square samples (approximately 5 g and 50 mm×50 mm) were cut out from rubber sheets prepared from the rubber compound (see the above rubber mixing procedure) and rolled out on a two-roller mill (see the above two-roll miller procedure).

2. RPA Method in the MDR Mode at 160 C Test Procedure to Obtain Time to 90% Cure Samples prepared as described above were placed between two Mylar film sheets, and then placed on the bottom RPA 2000 die. The samples were tested at 160° C. to determine the cure time and torque. The samples were run for 30 minutes at 160° C., 1.7 Hz and 6.98% strain to measure the cure properties, such as time to 90% cure, T90, which was obtained and used in other procedures to cure the samples.

3. RPA Method Test Procedure to Obtain Cure Properties 3.1 After obtaining the T90 from (2) a new uncured sample was placed in the RPA (as prepared in (1)) and evaluated by sweeping the strain to measure the pre-cure viscosity. The % strain was swept at the following temperature and frequency:
 3.1.1 Strain 1—100° C., 0.1 Hz,
 3.1.2 Strain 2—100° C., 20 Hz,
 3.1.3 Strain 3—100° C., 1.0 Hz 3.2 Sample was then cured at 160° C. for 30 minutes at 1.7 Hz, 6.98% strain.

3.3 After curing, the sample was subjected to 4 strain sweeps in the % strain range of 0.5% to 10%, and a hold between the last two sweeps to obtain the dynamic properties G' elastic modulus, G" viscous modulus, and the G'/G" ratio known as tan D:
 3.3.1 Strain 1—100° C., 1.0 Hz;
 3.3.2 Strain 2—100° C., 1.0 Hz;
 3.3.3 Strain 3—110° C., 10 Hz;
 3.3.4 Hold: 10 minutes at 110° C. at 10 Hz, and 1.0% strain;
 3.3.5 Strain 4—110° C., 10 Hz.

The instrument software produces the dynamic properties G' (elastic modulus), G" (viscous modulus), and the G'/G" ratio which is called tan D.

The Mullins effect was obtained from $1^{st}$ and $2^{nd}$ strains on the cured sample (3.3.1 and 3.3.2 respectively). A % change between the $2^{nd}$ and the $1^{st}$ G' values at a given frequency is the Mullins effect.

Cure Properties

Figure 7:
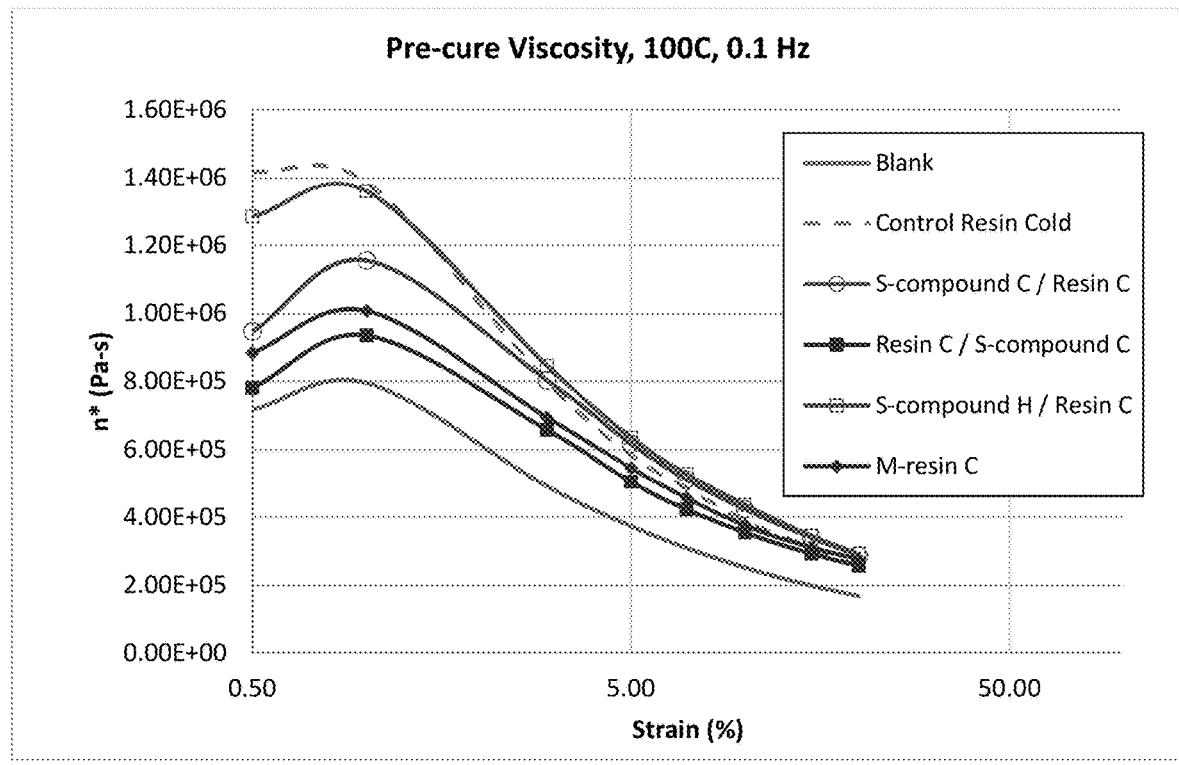
FIG. 7 shows the mixing viscosity for each rubber sample, characterized by pre-cure Strain Sweep n* at 100° C. as a function of strain angle. The rubber samples are described in Table 5.
Figure 8:
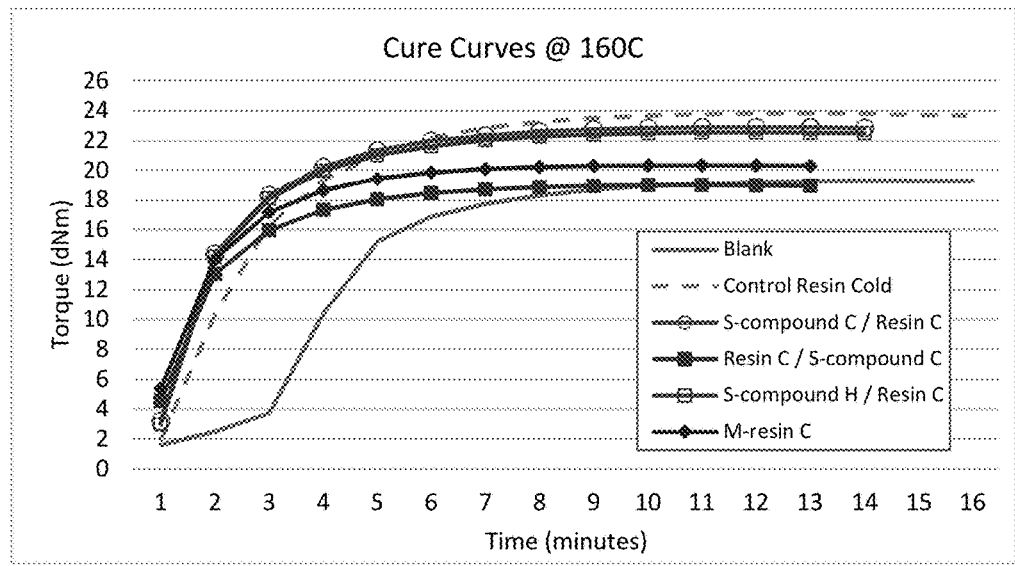
FIG. 8 shows the curing property for each rubber sample, characterized by torque at 160° C. as a function of time. The rubber samples are described in Table 5.

The cure properties of each sample are shown in FIGS. 7 and 8. The curing property was characterized by an RPA 2000 at 160° C., and the curing curves were plotted as a function of time. See section 3.2 above for cure parameters.

FIG. 7 shows that each rubber sample exhibited pre-cure viscosities no higher than the phenol novoloc resin control sample mixed in the cold pass. Accordingly, there are no concerns regarding compounding and handling of these materials. The cure curves shown in FIG. 8 illustrate a wide range in crosslink density depending on how the individual samples were prepared. A torque range of approximately 5 dNm was observed, wherein the Blank, Resin C/S-compound C, and M-resin C rubber samples have the three lowest crosslink densities. All other rubber samples have similar crosslink densities.

Tensile Properties

The rubber sheet was remilled to make ASTM D412 tensile bars, with the dials rotated 40 degrees counter clockwise to 60 mm. The sample was run back through and milled into a 2 mm-thick rectangular sheet. An ASTM D412 die was used to cut the plaque that eventually became tensile bars. The cut samples were placed in 150 mm×150 mm square cavities. Samples were cured based on T90+4 minutes. After samples were removed, the tensile bars were cut using a die.

Samples were tested using ASTM D412 method A and an Instron model 5965 universal tensile testing machine (Instron). The video extensimeter (AVE model 2663-901) for recording stress/strain data from the marked cross sectional was calibrated prior to testing. The specimen were marked with two white dots 5 mm apart using a jig. These two small dots represent the test cross section area tested. Samples were then placed in 1 kN pneumatic grips, using a 5 kN load cell to displace the samples for stress/strain calculations.

Figure 9:
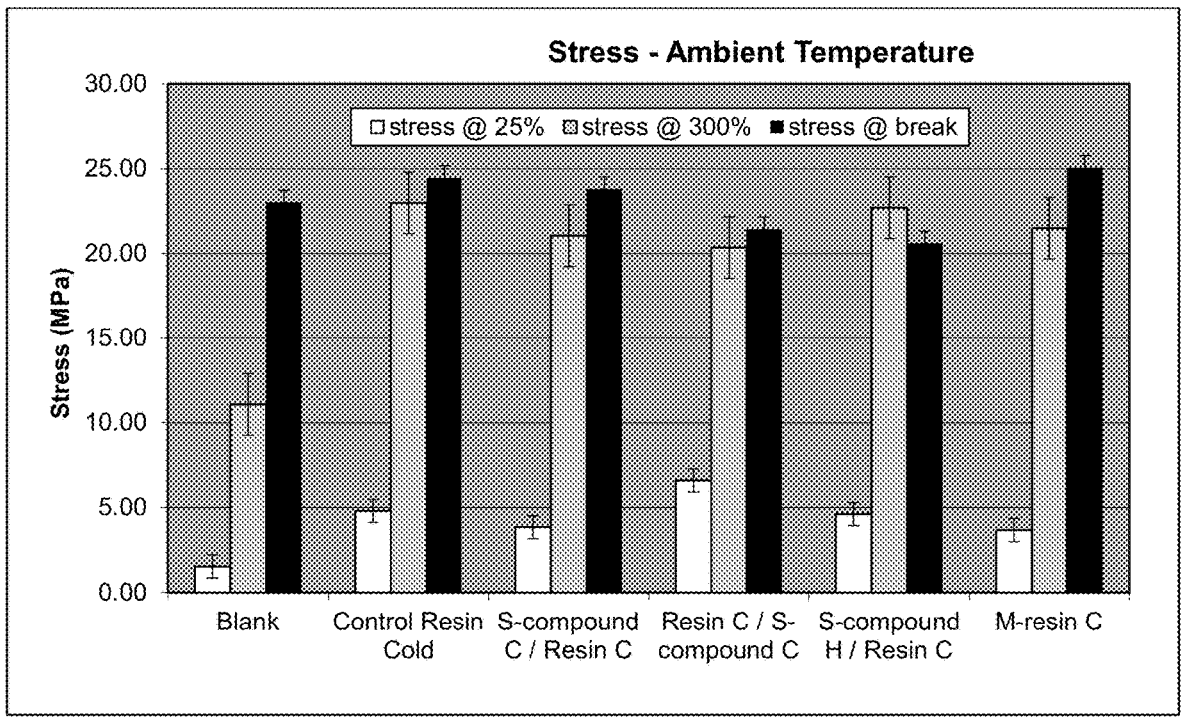
FIG. 9 shows the tensile stress at given strains for each rubber sample. The rubber samples are described in Table 5.

The results of the tensile stresses at given strains for the rubber samples are shown in FIG. 9. The tensile stresses of the various rubber samples were comparable at the test temperature, albeit minor differences between the samples.

Figure 10:
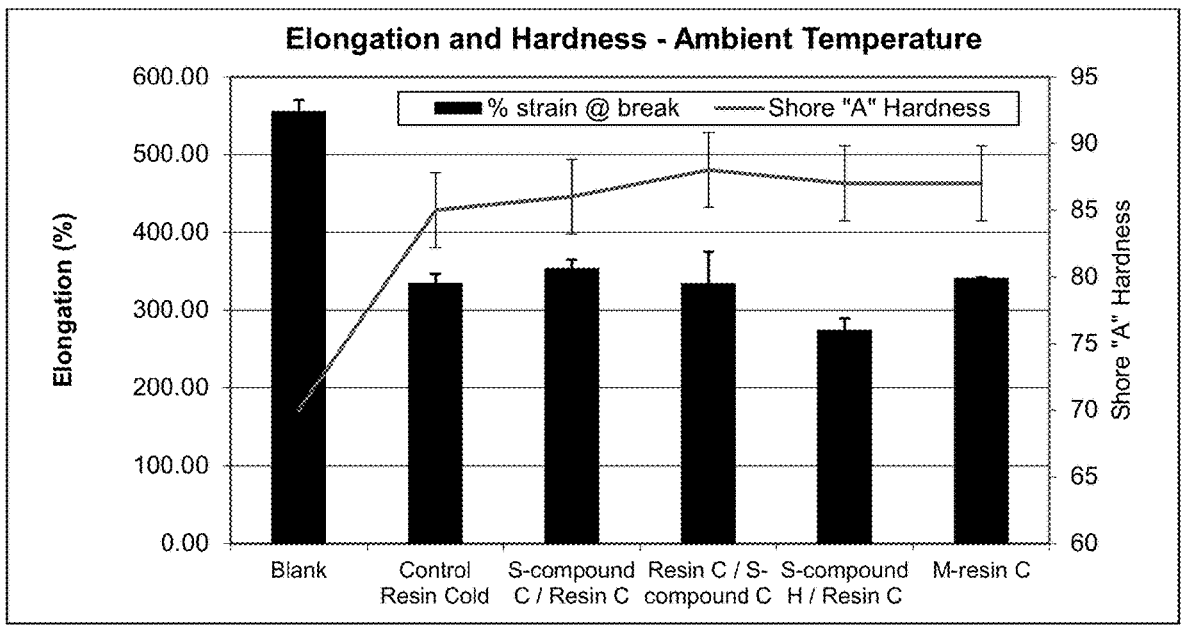
FIG. 10 shows the tensile elongation for each rubber sample. The rubber samples are described in Table 5.

The results of the tensile elongations for the rubber samples are shown in FIG. 10. The elongations of the various rubber samples were comparable at the test temperature, albeit minor differences for the rubber samples containing the functionalized organosulfur compound.

Dynamic Properties

Testing for dynamic properties of the rubber samples was performed on a rubber process analyzer (RPA) at 100-110° C. and 10 Hz after cure. The samples were subjected to 4 strain sweeps as described in section 3.3 above. Samples produced G' elastic response modulus, G" viscous response modulus, and the ratio of elastic modulus over viscous modulus to arrive at the Tan D values. The results summarized in FIGS. 11A-1C were produced from the $3^{rd}$ strain sweep.

Figure 11A:
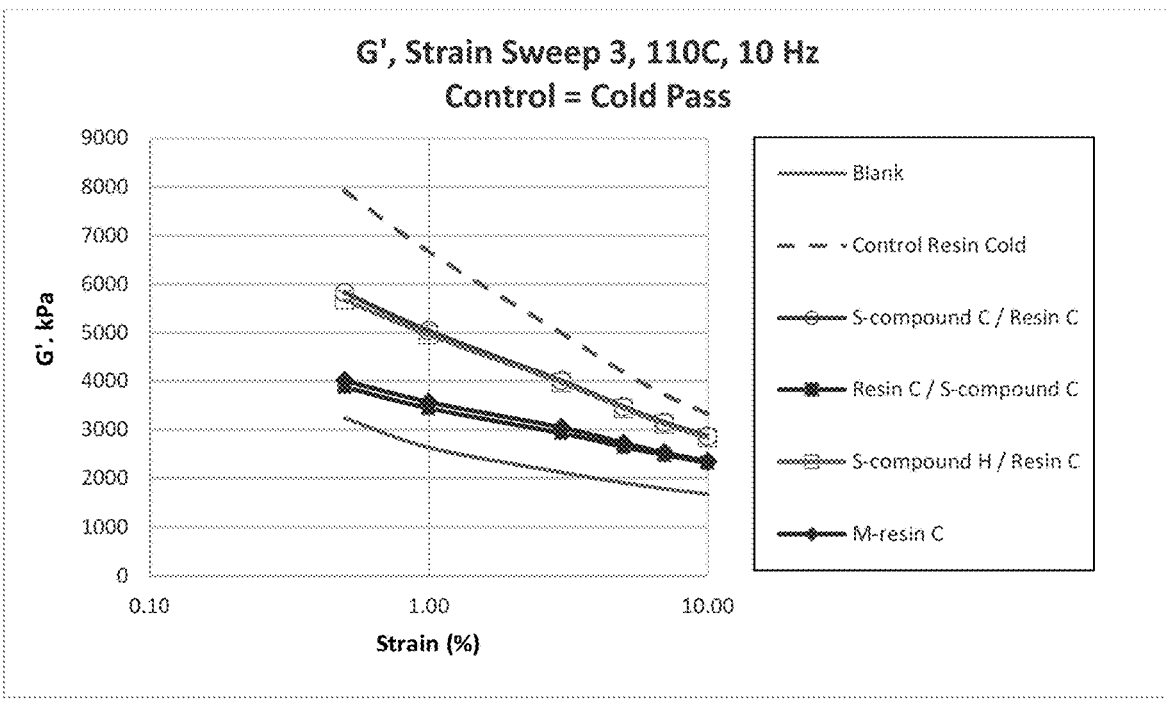
Figure 11B:
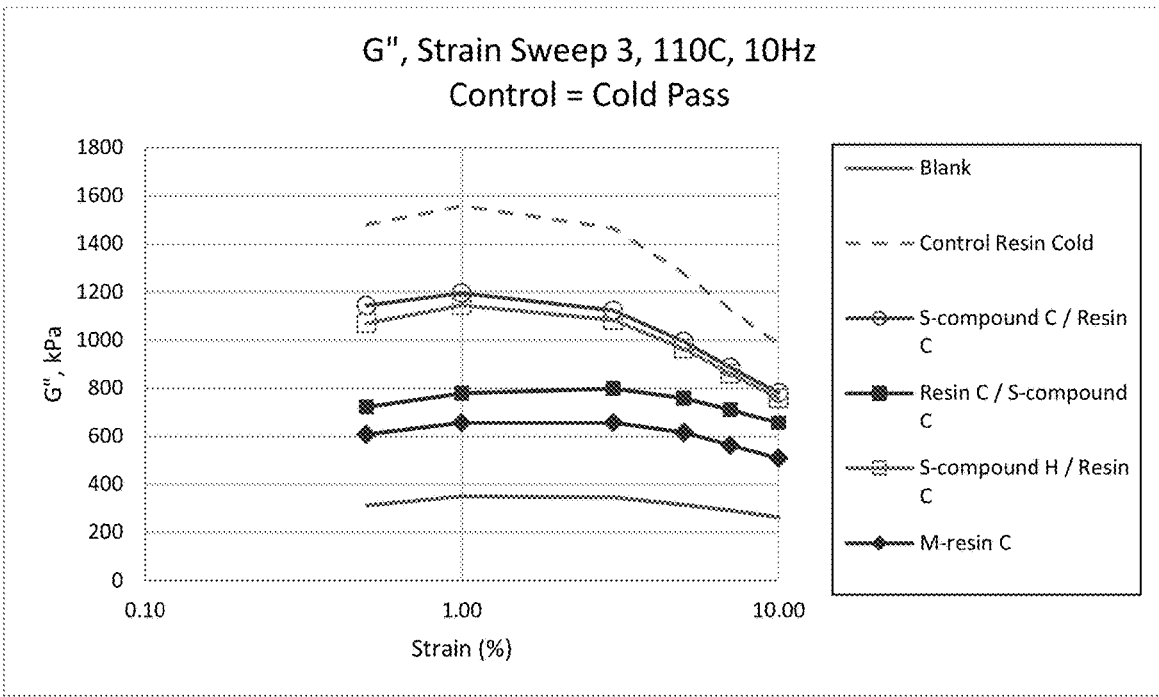
FIG. 11B shows the viscous modulus (G") for each rubber sample.
Figure 11C:
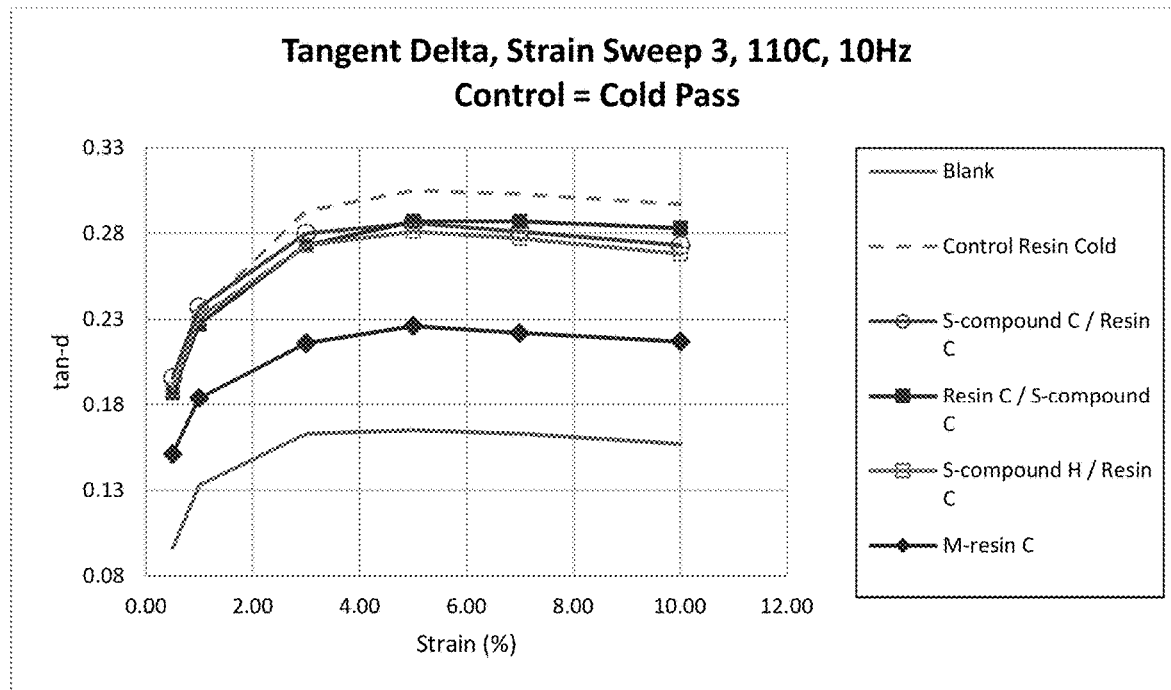
FIG. 11C shows the ratio of elastic modulus over viscous modulus (Tan D) for each rubber sample. The rubber samples are described in Table 5.

FIG. 11C shows the Tan D measurements for the rubber samples containing unmodified phenol novolac resin (Control Resin Cold Pass), the modified phenol novolac resins (M-resin C), and functionalized organosulfur compound (S-compound) and the resin separately mixed in Banbury mixer (Resin C). For the rubber samples where the modified phenol novolac resin was added during cold pass mixing, the Tan D values are reduced between 4 and 26% at 3% strain compared to the control resin (Control Resin Cold Pass).

FIG. 11A shows the elastic modulus (G') of the rubber samples containing the functionalized organosulfur compounds, including the samples containing the modified phenol novolac resin (M-resin C) and those where the functionalized organosulfur compound and the resin were separately mixed in Banbury mixer (S-compound H/Resin C, S-compound C/Resin C, and Resin C/S-compound C). FIG. 11A includes all of the samples where the unmodified phenol novolac resin or the modified phenol novolac resin was added in the cold pass. In the case of the samples where the modified phenol novolac resin was added during the cold pass of mixing, all compounds that incorporated a functionalized organosulfur compound showed a decrease in G' between, approximately, 21% and 41% at a strain of 3% over the rubber sample containing only the unmodified phenol novolac resin (Control Resin Cold Pass).

As shown in FIG. 11B, the rubber samples containing the functionalized organosulfur compound, including the modified phenol novolac resins (M-resin C) and those where the functionalized organosulfur compound and the resin were separately mixed in the Banbury mixer (S-compound H/Resin C, S-compound C/Resin C, and Resin C/S-compound C), all showed a drop in the viscous modulus, G", of approximately 23-55%, as compared to that of the rubber sample containing only the unmodified phenol novolac resin (Control Resin Cold Pass).

Heat Build-Up Properties as Measured by a Flexometer

The rubber sheet was re-milled and a rectangular sheet was used to make flexometer ASTM D623 samples. Samples for testing were made using a CCSI die approximately 25 mm in height and a CCSI tri-plate 8 cavity mold with cavities 25 mm in height, 17 mm in diameter. The samples were pressed in a heated hydraulic press according to T90+10 min specifications. Before placing samples in the mold, the heated press was heated to 160° C., and the CCSI mold was preheated to 160° C. After coming off the mill the sample rubber sheet was approximately 300 mm in width and 350 mm in length. The sheet was folded in half four times, and the die was then used to punch three separate punches from the folded rubber sheet to fill the 25 mm cavity in the tri-plate mold. Each of the three individual punches were packed into the mold cavity, a piece of foil was placed on top, and the top of the tri-plate was assembled to the mold. The samples were then cured for a time of T90+10 minutes. The mold was then removed from the press, and the samples were removed from the mold cavities and allowed to cool to room temperature.

Samples for heat generation were tested based on ASTM D623 with some slight modifications, as noted below. The test was run on EKT-2002GF (Ektron). The weight of 160N and a frequency of 33 Hz were used. The permanent (flex fatigue) set calculations were also based on ASTM D623 specifications, using a micrometer.

Figure 12:
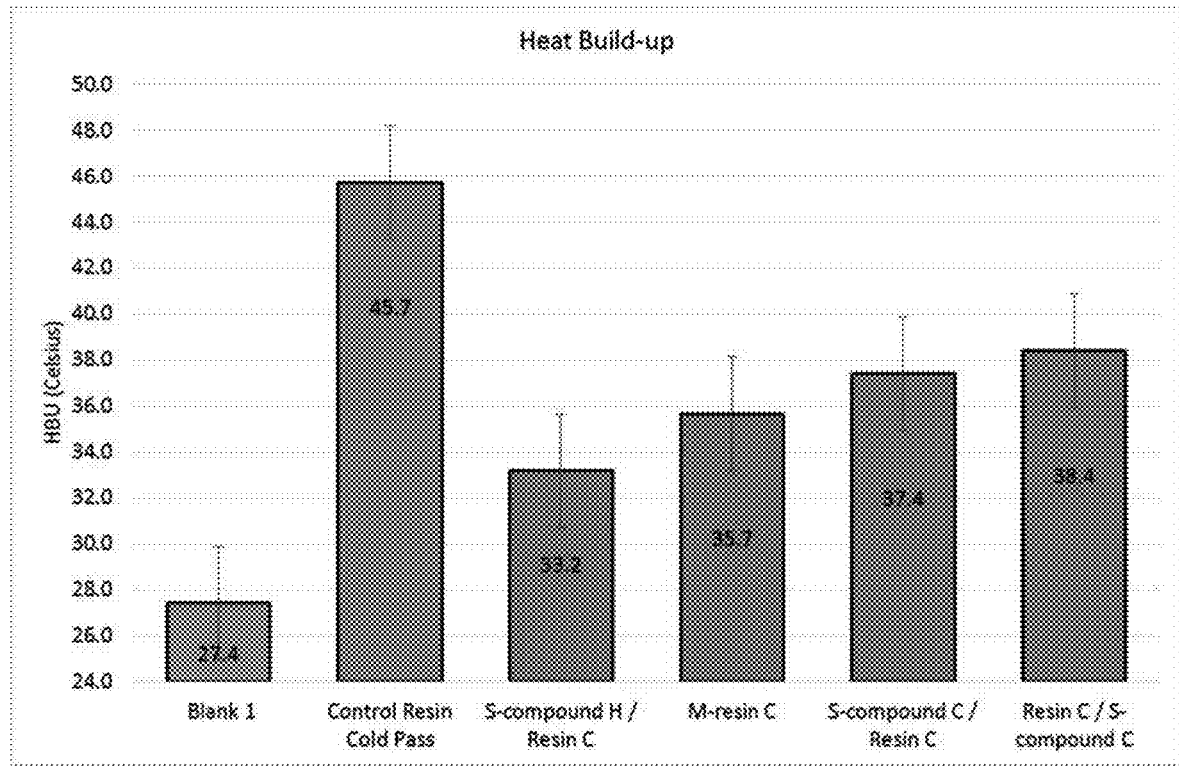
FIG. 12 shows the heat build-up, measured by a flexometer, for each rubber sample. The rubber samples are described in Table 5.

The results of heat build-up (HBU) from a series of 3 runs were averaged and summarized in FIG. 12.

As shown in FIG. 12, the rubber samples containing the functionalized organosulfur compound, including the one having the modified phenol novolac resin (M-resin C) and those where the functionalized organosulfur compound and the resin were separately mixed in Banbury mixer (S-compound H/Resin C, S-compound C/Resin C, and Resin C/S-compound C), all showed a significant improvement in the HBU, as compared to that of the rubber sample containing only the unmodified phenol novolac resin (Control Resin Cold Pass). Additionally, the rubber sample where the functionalized organosulfur compound and the resin were separately mixed in during Banbury mixing and where the functionalized organosulfur compound was added during the first pass of mixing and the phenol novolac resin was added during the second pass of mixing (S-compound H/Resin C) showed an equivalent or slightly improved HBU than the rubber sample where the resin was pre-mixed with the functionalized organosulfur compound (M-resin C).

Example 13: Preparation of a Rubber Compound for Bonding Applications

A rubber compound was prepared according to the formulation shown in Table 6 below for wire-bonding applications in a tire. The compound uses a phenolic novolac resin modified by the functionalized organosulfur compound shown in Example 1A. The steel wire belt, located in a ply between the tread and carcass, requires reinforcement for stiffness and a lowered hysteresis would aid in improving the wear on the tire and rolling resistance of the vehicle.

TABLE 6

| Rubber formulation for wire-bonding application | |
|---|---|
| Ingredient | Loading (phr) |
| Pass 1 | |
| SMR 20 (Smoked Malaysian Rubber) | 100.00 |
| Silica | 15.00 |
| Zinc Oxide | 6.00 |
| Stearic acid | 2.00 |
| Wingstay 100 | 1.00 |
| Cobalt(II) naphthenate | 0.75 |
| Carbon black, N326 | 55.00 |
| Paraffinic oil | 4.00 |
| Elaztobond ® A250 | 4.00 |
| Functionalized organosulfur compound (S-compound) | 0.50 |
| TOTAL: | 128.75 |
| Pass 2 | |
| Insoluble sulfur | 1.72 |
| TBBS accelerator | 2.15 |
| HMMM | 2.50 |

Rubber mixing was performed as a two-pass mix. For individual bonding formulation samples, a phenolic novolac resin and the functionalized organosulfur compound (S-compound), as prepared in Example 1A, were mixed into the master batch at 4.00 and 0.50 phr, respectively. During the second pass of mixing, the cure package, which includes insoluble sulfur (1.72 phr), N-tert-butyl-benzothiazole sulfonamide (TBBS) sulfur accelerator (2.15 phr), and hexakis (methoxymethyl)-melamine (HMMM) crosslinker (2.50 phr) were added.

Sample Preparation

Compounding of the rubber formula outlined above was completed in a BR1600HF internal mixer (Farrel Pomini, CT) with automated mixing functionality having a 1.5 L volume capacity and a fill factor of 70% generated to produce 1256 g of compound. The rubber was cut into squares approximately 75 mm×75 mm until the fill factor weight of 1256 g was obtained. By multiplying 70% fill factor by 4 phr of the phenolic resin composition, 0.5 phr of the functionalized organosulfur compound (S-compound), 1.72 phr sulfur, 2.15 phr TBBS, and 2.5 phr HMM, the gram weight of each of the additives being compounded was obtained. Once the total amount of rubber samples were cut and weighed (including the cure package and resin additives), samples were ready to be compounded.

Compounding

For compounding, the rotor speed was 50 rpm and the initial temperature was 60° C. The natural rubber that was cut and weighed approximately 670 g was added and the ram was dropped. The mixing was carried out for 30 seconds from the drop of the ram. The ram was raised to add the silica and the ram was dropped again and allowed to mix at 50 rpm for 3 minutes. The ram was then raised to add the zinc oxide, stearic acid, Wingstay 100, Elaztobond® A250, cobalt(II) naphthenate, carbon black, and paraffinic oil. The ram was lowered and the rpms were held constant at 50, and the batch temperature increased from the friction of the natural rubber, additives, and resin in the mixer. The mixing time was 3 minutes. After this 3-minute cycle, the ram was raised to add the functionalized organosulfur compound from Example 1A. The ram was once again lowered and the batch was allowed to mix for 1 minute at 50 rpm. The batch was then expelled into the collection bin. The rubber was then put on the mill to be calendared and rest overnight.

The following day, the second pass of mixing was performed. For compounding, the rotor speed was 50 rpm and the initial temperature was 60° C. During this mixing step, the rubber compound from pass one was cut into approximately 75×75 mm squares which were fed into the BR1600HF internal mixer and the ram was lowered. Mixing time was 30 seconds. The ram was raised to add the insoluble sulfur, TBBS accelerator, and HMMM crosslinker. The ram was then lowered and the curatives were mixed for 4 minutes at 50 rpm. The batch was then expelled into the collection bin and the rubber was put on the mill to be calendared.

Roll Mill

After each pass of mixing, the rubber that was dropped was immediately milled. The Reliable two roll mill was preheated to approximately 43-45° C., and the dials that control thickness were set to 0 mm for the initial cross-blending. The rubber was banded, and then each side of the rubber was cut, pulled, and allowed to bind with the adjacent side. Each side was cut 3 times for a total of 6 cut and pulls. This process was done for a total of 4 minutes. The sample was then removed from the mill, and cut into two separate sheets.

RPA Sample Prep

To obtain cure data, square samples (approximately 5 g and 50 mm×50 mm) were run on the RPA 2000 (Alpha Technologies). No pre-cure testing was required.

RPA: MDR 160 C Test Procedure

Samples were placed between two mylar film sheets, and then placed on the bottom RPA 2000 die. 160 C test process was followed to determine cure time and torque. The sample was run for 30 minutes and was heated to 160° C. at 1.7 Hz, 6.98% strain to yield cure data, such as T90, which was used to cure samples for other tests.

RPA Passenger Tire Test

Samples were subjected to pre-cure viscosity sweep composed of three strains: Strain 1-100° C., 0.1 Hz for 17 minutes. Strain 2-100° C., 20 Hz for 0.008 minute, and Strain 3-100° C., 1.0 Hz, for 0.167 minute to obtain the pre-cure viscosity data. Samples were then cured at 160° C. for 30 minutes at 1.7 Hz, 6.98% strain. After the cure, the samples were subjected to 4 strain sweeps. The $1^{st}$ strain sweep: 0.5-10% strain, 100° C., and 1.0 Hz; the $2^{nd}$ strain sweep: 0.5-10% strain, 100° C., and 1.0 Hz; and the $3^{rd}$ strain sweep: 0.5-10% strain, 110° C., and 1.0 Hz. Another strain sweep at 110° C., 10.0 Hz, and 1.00% strain angle occurred before a fourth test sweep. The $4^h$ test sweep was performed from 0.5-10% strain, 110° C., and 10.0 Hz. Samples produced G' elastic response modulus, G" viscous response modulus, and the ratio of elastic modulus over viscous modulus to arrive at the Tan D values.

Flexometer Heat Build and Permanent Set Sample Prep

The second of two rubber sheets were remilled and a rectangular sheet was used to make flexometer ASTM D623 samples. Samples for testing were made using a CCSI die approximately 25 mm in height and a CCSI triplate 8 cavity mold with cavities 25 mm in height, 17 mm in diameter. The samples were pressed in a heated hydraulic press according to T90+10 min specifications. Before placing samples in the mold, the heated press was heated to 160° C., and the CCSI mold was preheated to 160° C. After coming off the mill the sample rubber sheet was approximately 300 mm in width and 350 mm in length. The sheet was folded in half four times, and the die was then used to punch three separate punches from the folded rubber sheet to fill the 25 mm cavity in the tri plate mold. Each of the three individual punches were packed into the mold cavity, a piece of foil was placed on top, and the top of the triplate was assembled to the mold. The samples were then cured for a time of T90+10 minutes. The mold was then removed from the press, and the samples were removed from the mold cavities and allowed to cool to room temperature.

Flexometer Heat Buildup and Permanent Set Testing

Samples for heat generation were tested based on ASTM D623 with some slight modifications, as noted below. The test was run on EKT-2002GF (Ektron). The weight of 160N and a frequency of 33 Hz were used. The permanent (flex fatigue) set calculations were also based on ASTM D623 specifications, using a micrometer.

Tensile Strength Properties of Rubber Sample Prep

The first of the two sheets was remilled to make ASTM D412 tensile bars, with the dials rotated 40 degrees counter clockwise to 60 mm. The sample was run back through and milled into a 2 mm rectangular sheet. An ASTM D412 die was used to cut the plaque that eventually became tensile bars. The cut samples were placed in 150 mm×150 mm square cavities. Samples were cured based on T90+4 minutes. After samples were removed, the tensile bars were cut using a die.

Tensile Strength Properties of Rubber

Samples were tested using ASTM D412 method A and an Instron model 5965 universal tensile testing machine (Instron). The video extensimeter (AVE model 2663-901) for recording stress/strain data from the marked cross sectional was calibrated prior to testing. The specimen were marked with two white dots 5 mm apart using a jig. These two small dots represent the test cross section area tested. Samples were then placed in 1 kN pneumatic grips, using a 5 kN load cell to displace the samples for stress/strain calculations.

Durometer Hardness

Hardness of cured rubber samples was determined by using a Rex durometer (Rex Gauge Company Inc.). To determine the hardness of the flexometer samples, the sample was placed flat side down and the anvil was dropped on the top, flat side. To determine the hardness of the Tensile samples, two samples were placed on top of each other and the anvil was dropped on the middle of the cross-sectional area.

Property Comparisons Between the Rubber Samples

The rubber samples prepared according to the above procedures were tested according to the above testing protocols, and the results are summarized in Table 7.

TABLE 7

The property comparisons between the rubber samples

| Sample | Stress @ 25% Strain (MPa) | Elongation @ break (%) | G'[d] (kPa) | Permanent Set(%)[e] | Tan-D[f] | Heat Rise[g] (° C.) |
|---|---|---|---|---|---|---|
| Blank[a] | 1.18 | 685.6 | 1457.2 | 96 | 0.096 | 17.57 |
| Control (a commercial phenol novolac resin) [b] | 1.52 | 758.6 | 1741.5 | 90 | 0.134 | 22.80 |
| Mixing a functionalized organosulfur compound prepared in Example 1A with a resin [c] | 1.77 | 749.2 | 1957.0 | 92 | 0.130 | 17.93 |

[a] Rubber compound prepared according to Table 6 (but without a phenol novolac resin, without a functionalized organosulfur compound, and without a crosslinker)
[b] Rubber compound prepared according to Table 6 (but without a functionalized organosulfur compound)
[c] Rubber compound prepared according to Table 6: samples were mixed into a natural rubber compound for wire-bonding applications at a loading of 0.5 phr a functionalized organosulfur compound and 4.00 phr a commercial phenol novolac resin for
[d] G' was measured by RPA during Strain Sweep 3 at 7% strain, 110° C., and 1 Hz.
[e] Permanent set was a ratio of final sample height divided by initial sample height measured before and after flexometer testing.
[f] Tan D was measured by RPA for strain sweep 3 at 7% strain, 110° C., 1 Hz.
[g] Heat rise was measured by flexometry.

The blank rubber compound sample consisted of all ingredients in the rubber compound for bonding shown in Table 6, except without a phenol novolac resin, a functionalized organosulfur compound, and crosslinker (HMMM). The blank sample exhibited the highest height retention after flexometry as noted by its permanent set value of 0.96. The blank sample also had the lowest Tan D and dynamic heat build-up, because it did not contain any phenolic resin which would contribute to the hysteresis of the rubber compound. The blank sample also displayed the lowest stress at 25% strain and elongation at break.

The control rubber sample used for comparison contain all ingredients in the rubber compound for bonding shown in Table 6, except without a functionalized organosulfur compound. The resin used was a commercial reinforcing resin (SI Group Elaztobond® A250). Like the sample containing the functionalized organosulfur compound, the control sample included the use of the HMMM crosslinker during rubber compounding. HMMM provided crosslinking between phenolic moieties, resulting in the formation of a resin-HMMM network that interpenetrates the rubber network and provides a reinforcing capability to that rubber compound. The control sample exhibited lower permanent sets (0.90) than the blank samples due to the break-down of the interpenetrating network during the cyclical strain of the material during flexometer testing. Addition of a resin to the rubber compound also resulted in a much higher Tan D and dynamic heat build-up when compared to the blank. The ability of the resin and resin-HMMM crosslinked network to move and flow within the rubber matrix and was illustrated by the Tan D value (0.134 v. 0.096) and heat rise (22.80° C. v. 17.57° C.) when compared to the blank sample. The control sample also exhibited a much higher storage modulus (G') than the blank sample (1741.5 kPa v. 1457.2 kPa).

The mixing rubber sample contain all ingredients in the rubber compound for bonding shown in Table 6. Interaction between 2,2'-[dithiobis(2,1-ethanediylnitriloethylidyne)]bis-phenol (1.00 phr), Elaztobond® A250 (4.00 phr), and HMMM crosslinker (2.50 phr) within the rubber compound showed enhanced improvement in hysteretic drop for a tire bonding compound compared to the control sample. The mixing sample showed a greater than 20% drop in dynamic heat buildup while providing improved mechanical properties as compared to the control sample. The mixing sample also exhibited a higher permanent set after flexometry compared to the control sample, indicating a higher degree of the original sample dimensions were retained after flexometry cycling.

What is claimed is:

1. A phenolic resin composition comprising:
    a phenolic resin admixed with and/or modified by one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one heteroatom-containing divalent moiety selected from the group consisting of imine, amine, amide, imide, ether, and ester moiety.

2. The phenolic resin composition of claim 1, wherein the phenolic resin composition comprises the admixture of the phenolic resin and the functionalized organosulfur compounds.

3. The phenolic resin composition of claim 1, wherein the phenolic resin composition comprises the reaction product of:
    at least one phenolic compound,
    at least one aldehyde, and
    the one or more functionalized organosulfur compounds.

4. The phenolic resin composition of claim 1, wherein the phenolic resin is a monohydric- or dihydric-phenolic-aldehyde resin, optionally modified by a naturally-derived organic compound containing at least one unsaturated bond.

5. The phenolic resin composition of claim 1, wherein the phenolic resin is used as a bonding resin or a reinforcing resin.

6. The phenolic resin composition of claim 1, wherein the amount of the functionalized organosulfur compound ranges from about 0.1 to about 25 wt %.

7. The phenolic resin composition of claim 1, wherein organosulfur compound is a thiol, disulfide, or thioester compound, having at least one functionalization connected to the thiol, disulfide, or thioester moiety through a linking moiety and at least an imine, amine, ether, or ester moiety.

8. The phenolic resin composition of claim 1, wherein one or more organosulfur compounds have the structure of formula (B-1) or (B-2):

(B-1)

or

(B-2), wherein:
    X is $S_z$ or S—C(=O);
    z is an integer from 2 to 10;
    $R_1$ and $R_2$ each are independently a divalent form of $C_1$-$C_{30}$ alkane, divalent form of $C_3$-$C_{30}$ cycloalkane, divalent form of $C_3$-$C_{30}$ heterocycloalkane, divalent form of $C_2$-$C_{30}$ alkene, or combinations thereof; each optionally substituted by one or more alkyl, alkenyl, aryl, alkylaryl, arylalkyl, or halide groups;

R$_3$ and R$_4$ each are independently absent, or a divalent form of imine (—R'''—N=C(R')—R'''—), amine (—R'''—N(R')—R'''—), amide

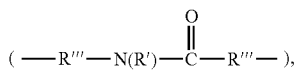

imide

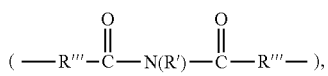

ether (—R'''—O—R'''—), or ester

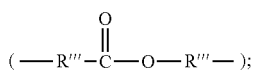

provided that at least one of R$_3$ and R$_4$ is present;

R$_5$ and R$_6$ each are independently H, alkyl, aryl, alkylaryl, arylalkyl, acetyl, benzoyl, thiol, sulfonyl, nitro, cyano, epoxide

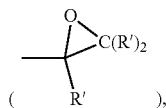

anhydride

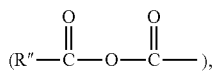

acyl halide

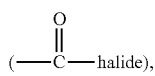

alkyl halide, alkenyl, or a phenolic moiety having one or more unsubstituted para- or ortho-positions; provided that at least one of R$_5$ and R$_6$ is a phenolic moiety having one or more unsubstituted para- or ortho-positions; and provided that when R$_3$ is —R'''—O—R'''—, R$_5$ is not H, and when R$_4$ is —R'''—O—R'''—, R$_6$ is not H; and each R' is independently H or alkyl, each R'' is independently alkyl, and each R''' is independently absent or divalent form of alkane.

9. A rubber composition, comprising:
(i) a rubber component comprising a natural rubber, a synthetic rubber, or a mixture thereof,
(ii) a phenolic resin component comprising one or more phenolic resins; and
(iii) an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one heteroatom-containing divalent moiety selected from the group consisting of imine, amine, amide, imide, ether, and ester moiety.

10. The rubber composition of claim 9, wherein component (ii) is pre-admixed with or pre-modified by component (iii).

11. The rubber composition of claim 9, further comprising one or more methylene donor agents.

12. The rubber composition of claim 9, wherein the interaction between the component (i) and the components (ii) and (iii) reduces the hysteresis increase or heat buildup compared to a rubber composition without the component (iii).

13. The rubber composition of claim 12, wherein the heat buildup, as measured by a flexometer, is reduced by at least about 1° C., compared to a rubber composition without the component (iii).

14. The rubber composition of claim 12, wherein the hysteresis increase, as measured by tan δ, is reduced by at least about 10%, compared to a rubber composition without the component (iii).

15. The rubber composition of claim 9, wherein the phenolic resin is a monohydric- or dihydric-phenolic-aldehyde resin, optionally modified by a naturally-derived organic compound containing at least one unsaturated bond.

16. The rubber composition of claim 9, wherein the organosulfur compound is a thiol, disulfide, or thioester compound, having at least one functionalization connected to the thiol, disulfide, or thioester moiety through a linking moiety and an imine or ester moiety.

17. The rubber composition of claim 9, wherein the amount of the components (ii) and (iii) in the rubber composition range from about 0.5 to about 50 parts per 100 parts rubber by weight.

18. A rubber product formed from the rubber composition of claim 9.

19. A process for preparing a rubber composition, comprising:
mixing (i) a rubber component comprising a natural rubber, a synthetic rubber, or a mixture thereof, (ii) a phenolic resin component comprising one or more phenolic resins, and (iii) an organosulfur component comprising one or more functionalized organosulfur compounds, wherein the organosulfur compound is a thiol, disulfide, polysulfide, or thioester compound, and wherein the functionalization of the organosulfur compound comprises one or more phenolic moieties having one or more unsubstituted para- or ortho-positions, at least one phenolic moiety being bonded to the thiol, disulfide, polysulfide, or thioester moiety through a linking moiety and at least one heteroatom-containing divalent moiety selected from the group consisting of imine, amine, amide, imide, ether, and ester moiety.

20. The process of claim 19, wherein the mixing further comprises:
pre-mixing or pre-modifying the component (ii) with component (iii).

21. The process of claim 19, further comprising:
adding one or more methylene donor agents to the rubber composition.

22. The process of claim 19, further comprising:
forming a rubber product from the rubber composition, wherein the rubber product is selected from the group consisting of a tire or tire component, a hose, a power belt, a conveyor belt, a printing roll, a rubber wringer, a ball mill liner, and combinations thereof.

23. The process of claim 19, wherein the phenolic resin is a monohydric- or dihydric-phenolic-aldehyde resin, optionally modified by a naturally-derived organic compound containing at least one unsaturated bond.

24. The process of claim 19, wherein the organosulfur compound is a thiol, disulfide, or thioester compound, having at least one functionalization connected to the thiol, disulfide, or thioester moiety through a linking moiety and an imine or ester moiety.

25. The process of claim 19, wherein the mixing results in an interaction between the component (i) and the components (ii) and (iii) to reduce the hysteresis increase, caused in the rubber composition when a phenolic resin is added to the rubber composition, compared to a rubber composition without the component (iii).

26. The process of claim 25, further comprising:
curing (vulcanizing) the rubber composition to further reduce the hysteresis increase.

* * * * *